(12) United States Patent
Narayanan

(10) Patent No.: US 10,473,658 B2
(45) Date of Patent: Nov. 12, 2019

(54) 4,4-DISUBSTITUTED CYCLOHEXYL BRIDGED HEPTAMETHINE CYANINE DYES AND USES THEREOF

(71) Applicant: VisEn Medical, Inc., Waltham, MA (US)

(72) Inventor: Narasimhachari Narayanan, Westford, MA (US)

(73) Assignee: VisEn Medical, Inc., Waltham, MA (US)

(*) Notice: Subject to any disclaimer, the term of this patent is extended or adjusted under 35 U.S.C. 154(b) by 0 days.

(21) Appl. No.: 15/890,646

(22) Filed: Feb. 7, 2018

(65) Prior Publication Data

US 2018/0164312 A1 Jun. 14, 2018

Related U.S. Application Data

(62) Division of application No. 14/215,930, filed on Mar. 17, 2014, now Pat. No. 9,897,604.

(60) Provisional application No. 61/798,562, filed on Mar. 15, 2013.

(51) Int. Cl.

| | | |
|---|---|---|
| A61B 10/00 | (2006.01) | |
| A61B 5/00 | (2006.01) | |
| A61B 8/00 | (2006.01) | |
| G01N 33/569 | (2006.01) | |
| C09B 23/01 | (2006.01) | |
| C09B 23/08 | (2006.01) | |
| G01N 33/58 | (2006.01) | |
| A61K 49/00 | (2006.01) | |
| A61K 51/04 | (2006.01) | |
| C07D 403/08 | (2006.01) | |
| C07D 403/14 | (2006.01) | |
| C07D 413/14 | (2006.01) | |
| C07D 417/14 | (2006.01) | |

(52) U.S. Cl.
CPC ... *G01N 33/56966* (2013.01); *A61K 49/0032* (2013.01); *A61K 49/0052* (2013.01); *A61K 49/0056* (2013.01); *A61K 51/0446* (2013.01); *C07D 403/08* (2013.01); *C07D 403/14* (2013.01); *C07D 413/14* (2013.01); *C07D 417/14* (2013.01); *C09B 23/0066* (2013.01); *C09B 23/086* (2013.01); *G01N 33/582* (2013.01); *C07B 2200/05* (2013.01)

(58) Field of Classification Search
CPC ............ A61K 49/00; A61K 49/0056; A61K 49/0052; A61K 49/0032; A61K 51/00; A61K 51/0446; A61K 2121/00; A61K 2123/00; G01N 33/56966; G01N 33/582; C07D 403/14; C07D 417/14; C07D 413/14; C07D 403/08; C09B 23/086; C09B 23/0066; C07B 2200/05

USPC ......... 424/1.11, 1.49, 1.65, 1.69, 1.81, 1.85, 424/1.89, 9.1, 9.2, 9.3, 9.4, 9.5, 9.6

See application file for complete search history.

(56) References Cited

U.S. PATENT DOCUMENTS

| | | | |
|---|---|---|---|
| 4,219,335 A | 8/1980 | Ebersole | |
| 5,164,297 A | 11/1992 | Josephson et al. | |
| 5,445,970 A | 8/1995 | Rohr | |
| 5,571,388 A * | 11/1996 | Patonay | C07D 209/60 204/461 |
| 5,593,658 A | 1/1997 | Bogdanov et al. | |
| 5,770,340 A | 6/1998 | Nakayama et al. | |
| 5,800,995 A * | 9/1998 | Patonay | C07D 209/60 204/452 |
| 5,876,915 A | 3/1999 | Deroover et al. | |
| 5,958,667 A * | 9/1999 | Deroover | G03C 1/28 430/584 |
| 6,027,709 A * | 2/2000 | Little | C07D 209/60 424/1.37 |
| 6,046,585 A | 4/2000 | Simmonds | |
| 6,048,982 A | 4/2000 | Waggoner | |
| 6,083,485 A | 7/2000 | Licha et al. | |
| 6,083,486 A | 7/2000 | Weissleder et al. | |
| 6,086,737 A * | 7/2000 | Patonay | C07D 209/12 204/452 |
| 6,136,612 A | 10/2000 | Della Ciana et al. | |
| 6,258,340 B1 | 7/2001 | Licha et al. | |
| 6,275,031 B1 | 8/2001 | Simmonds | |
| 6,448,008 B1 | 9/2002 | Caputo et al. | |
| 6,534,041 B1 | 3/2003 | Licha et al. | |
| 6,592,847 B1 | 7/2003 | Weissleder et al. | |

(Continued)

FOREIGN PATENT DOCUMENTS

| | | |
|---|---|---|
| EP | 0821266 A1 | 1/1998 |
| EP | 0821271 A1 | 1/1998 |

(Continued)

OTHER PUBLICATIONS

Abe S et al., "Correlation of in vivo Autofluorescence Endoscopy Images with Histopathologic Findings in Stomach Cancer", Endoscopy, Apr. 2000, 32(4):281-6.

(Continued)

*Primary Examiner* — D. L. Jones
(74) *Attorney, Agent, or Firm* — Goodwin Procter LLP

(57) ABSTRACT

The invention relates to a family of compounds that comprise fluorescent cyanine dyes. The compounds are near infrared absorbing heptamethine cyanine dyes with a 4,4-disubstituted cyclohexyl ring as part of the polymethine chromophore. The compounds are generally hydrophilic and can be chemically linked to biomolecules, such as proteins, nucleic acids, and therapeutic small molecules. The compounds can be used for imaging in a variety of medical, biological and diagnostic applications.

6 Claims, 2 Drawing Sheets

(56) References Cited

U.S. PATENT DOCUMENTS

| | | | |
|---|---|---|---|
| 6,593,148 B1* | 7/2003 | Narayanan | C07D 209/12 435/6.12 |
| 6,615,063 B1 | 9/2003 | Ntziachristos et al. | |
| 6,740,755 B2 | 5/2004 | Caputo et al. | |
| 6,747,159 B2 | 6/2004 | Caputo et al. | |
| 6,869,593 B2 | 3/2005 | Frangioni | |
| 6,913,743 B2 | 7/2005 | Licha et al. | |
| 6,926,885 B2 | 8/2005 | Licha et al. | |
| 6,974,873 B2 | 12/2005 | Leung et al. | |
| 6,995,274 B2* | 2/2006 | Lugade | C09B 23/0008 548/427 |
| 7,025,949 B2 | 4/2006 | Licha et al. | |
| 7,374,746 B2 | 5/2008 | Frangioni | |
| 7,383,076 B2 | 6/2008 | Ntziachristos et al. | |
| 7,445,767 B2 | 11/2008 | Licha et al. | |
| 7,504,089 B2* | 3/2009 | Lugade | C09B 23/0008 424/1.11 |
| 7,597,878 B2* | 10/2009 | Kovar | A61K 49/0032 424/1.11 |
| 7,647,091 B2 | 1/2010 | Ntziachristos et al. | |
| 7,655,217 B2 | 2/2010 | Licha et al. | |
| 7,947,256 B2 | 5/2011 | Rajopadhye et al. | |
| 7,962,200 B2 | 6/2011 | Ntziachristos et al. | |
| 8,170,651 B2 | 5/2012 | Ripoll Lorenzo et al. | |
| 8,173,819 B2* | 5/2012 | Rajopadhye | C07D 401/06 546/276.7 |
| 8,221,721 B2 | 7/2012 | Narayanan | |
| 8,303,936 B2* | 11/2012 | Draney | A61K 49/0032 424/1.11 |
| 8,420,055 B2 | 4/2013 | Gaw et al. | |
| 8,455,651 B2* | 6/2013 | Rajopadhye | C07D 401/06 546/276.7 |
| 8,486,373 B2 | 7/2013 | Weissleder et al. | |
| 8,685,370 B2 | 4/2014 | Rajopadhye et al. | |
| 8,771,646 B2* | 7/2014 | Rajopadhye | C07D 401/06 424/9.6 |
| 8,815,214 B2 | 8/2014 | Rajopadhye et al. | |
| 8,864,821 B2 | 10/2014 | Jaffer et al. | |
| 9,365,721 B2 | 6/2016 | Narayanan | |
| 9,371,362 B2 | 6/2016 | Ho | |
| 9,375,493 B2 | 6/2016 | Ho | |
| 9,427,481 B2 | 8/2016 | Rajopadhye et al. | |
| 9,574,085 B2* | 2/2017 | Narayanan | A61K 49/0032 |
| 9,649,389 B2 | 5/2017 | Groves et al. | |
| 9,791,450 B2 | 10/2017 | Mao et al. | |
| 9,897,604 B2* | 2/2018 | Narayanan | G01N 33/56966 |
| 9,913,917 B2 | 3/2018 | Groves et al. | |
| 9,999,687 B2 | 6/2018 | Rajopadhye et al. | |
| 10,092,188 B2 | 10/2018 | Jaffer et al. | |
| 10,221,159 B2 | 3/2019 | Groves et al. | |
| 2001/0055567 A1 | 12/2001 | Licha et al. | |
| 2002/0064794 A1 | 5/2002 | Leung et al. | |
| 2002/0065421 A1 | 5/2002 | Caputo et al. | |
| 2002/0156288 A1 | 10/2002 | Caputo et al. | |
| 2003/0026763 A1 | 2/2003 | Licha et al. | |
| 2003/0124194 A1 | 7/2003 | Gaw et al. | |
| 2003/0170179 A1 | 9/2003 | Licha et al. | |
| 2003/0219383 A1 | 11/2003 | Weissleder et al. | |
| 2004/0028611 A1 | 2/2004 | Frangioni | |
| 2005/0106106 A1 | 5/2005 | Licha et al. | |
| 2005/0169843 A1 | 8/2005 | Weissleder et al. | |
| 2005/0169844 A1 | 8/2005 | Licha et al. | |
| 2005/0171434 A1 | 8/2005 | Madden et al. | |
| 2005/0245734 A1 | 11/2005 | Caputo et al. | |
| 2006/0002857 A1 | 1/2006 | Frangioni | |
| 2006/0239916 A1 | 10/2006 | Licha et al. | |
| 2006/0275775 A1 | 12/2006 | Weissleder et al. | |
| 2006/0280688 A1* | 12/2006 | Kovar | A61K 49/0032 424/9.6 |
| 2007/0036724 A1 | 2/2007 | Frangioni | |
| 2007/0238957 A1 | 10/2007 | Yared | |
| 2008/0102036 A1 | 5/2008 | Poss et al. | |
| 2008/0226562 A1 | 9/2008 | Groves et al. | |
| 2008/0267883 A1 | 10/2008 | Rajopadhye et al. | |
| 2008/0286207 A1 | 11/2008 | Narayanan | |
| 2008/0317676 A1 | 12/2008 | Rajopadhye et al. | |
| 2009/0068115 A1 | 3/2009 | Gaw et al. | |
| 2009/0123383 A1 | 5/2009 | Frangioni | |
| 2009/0130024 A1 | 5/2009 | Narayanan et al. | |
| 2009/0220430 A1 | 9/2009 | Rajopadhye et al. | |
| 2009/0305410 A1 | 12/2009 | Mao et al. | |
| 2010/0074847 A1 | 3/2010 | Madden et al. | |
| 2010/0078576 A1 | 4/2010 | Ntziachristos et al. | |
| 2010/0166659 A1 | 7/2010 | Licha et al. | |
| 2010/0172841 A1 | 7/2010 | Peterson et al. | |
| 2010/0189657 A1 | 7/2010 | Weissleder et al. | |
| 2010/0268070 A1 | 10/2010 | Jaffer et al. | |
| 2011/0049384 A1 | 3/2011 | Yared et al. | |
| 2011/0060211 A1 | 3/2011 | Lorenzo et al. | |
| 2011/0071388 A1 | 3/2011 | Yared et al. | |
| 2011/0087111 A1 | 4/2011 | Ntziachristos | |
| 2011/0152501 A1 | 6/2011 | Weissleder et al. | |
| 2011/0165075 A1 | 7/2011 | Rajopadhye et al. | |
| 2011/0171136 A1 | 7/2011 | Poss et al. | |
| 2011/0184277 A1 | 7/2011 | Ripoll Lorenzo et al. | |
| 2011/0256065 A1 | 10/2011 | Frangioni | |
| 2012/0321562 A1 | 12/2012 | Rajopadhye et al. | |
| 2012/0321563 A1 | 12/2012 | Groves et al. | |
| 2013/0137873 A1 | 5/2013 | Narayanan | |
| 2013/0272967 A1 | 10/2013 | Rajopadhye et al. | |
| 2014/0050662 A1 | 2/2014 | Ho | |
| 2014/0314677 A1 | 10/2014 | Groves et al. | |
| 2014/0348746 A1 | 11/2014 | Narayanan | |
| 2015/0018517 A1 | 1/2015 | Rajopadhye et al. | |
| 2015/0133773 A1 | 5/2015 | Jaffer et al. | |

FOREIGN PATENT DOCUMENTS

| | | |
|---|---|---|
| EP | 0924724 A2 | 6/1999 |
| EP | 1213583 A1 | 6/2002 |
| EP | 1810998 A2 | 7/2007 |
| EP | 2204194 A2 | 7/2010 |
| JP | 61-248789 A | 11/1986 |
| JP | 62-050187 A | 3/1987 |
| JP | 62-103190 A | 5/1987 |
| JP | 62-103192 A | 5/1987 |
| JP | 62-124986 A | 6/1987 |
| JP | H02-190390 A | 7/1990 |
| JP | 2004-67816 A | 3/2004 |
| JP | 2004-83799 A | 3/2004 |
| JP | 2011506673 A | 3/2011 |
| WO | WO-2003/079015 A1 | 9/2003 |
| WO | WO-2003/102558 A1 | 12/2003 |
| WO | WO-2007/028163 A1 | 3/2007 |
| WO | WO-2014/065439 A1 | 5/2014 |
| WO | WO-2014/144702 A2 | 9/2014 |

OTHER PUBLICATIONS

Alexander W, "Lasers Investigated as Diagnostic Tools for Breast Cancer", J Clin Laser Med Surg, Dec. 1991, 9(6):416-8.

Alfano RR et al., "Advances in Optical Imaging of Biomedical Media", Ann NY Acad Sci, May 30, 1997, 820:248-70.

Boas DA et al., "Scattering of Diffuse Photon Density Waves by Spherical Inhomogeneities Within Turbid Media: Analytic Solution and Applications", Proc Natl Acad Sci USA, May 24, 1994, 91(11):4887-91.

Chance B, "Near-Infrared Images Using Continuous, Phase-Modulated, and Pulsed Light with Quantiation of Blood and Blood Oxygenation", Ann NY Acad Sci, Feb 9, 1998, 838:29-45.

Chemla YR et al., "Ultrasensitive Magnet Biosensor for Homogeneous Immunoassay", Proc Natl Acad Sci USA, Dec. 19, 2000, 97(26):14268-72.

Cheng X and Boas D, "Diffuse Optical Reflection Tomography Using Continuous Wave Illumination", Opt Express, Aug. 3, 1998, 3(3):118-23.

Citrin D and Camphausen K, "Optical Imaging of Mice in Oncologic Research", Expert Rev Anticancer Ther, Oct. 2004, 4(5):857-64.

Dellian M et al., "Vascular Permeability in a Human Tumor Xenograft: Molecular Charge Dependence", Br J Cancer, May 2000, 82(9):1513-8.

(56) References Cited

OTHER PUBLICATIONS

European Search Report for European Patent Application No. EP18211794 dated Mar. 8, 2019 (6 pages).
Fukumura D et al., "Tumor Induction of VEGF Promoter Activity in Stromal Cells", Cell, Sep. 18, 1998, 94(6):715-25.
Gahlen J et al., "Spectrometry Supports Fluorescence Staging Laparoscopy After Intraperitoneal Aminolaevulinic Acid Lavage for Gastrointestinal Tumors", J Photochem Photobiol B, Sep.-Oct., 1999, 52(1-3):131-5.
González S et al., "Characterization of Psoriasis in vivo Reflectance Confocal Microscopy", J Med, 1999 (1999), 30(5-6):337-56.
Graves EE et al., 'Fluorescence Molecular Imaging of Small Animal Tumor Models,' Curr Mol Med, Jun. 2004, 4(4):419-30.
Hamer FM, "Some Unsymmetrical Pentamethincyanine Dyes and their Tetramethin Intermediates", J Chem Soc, Jan. 1, 1949, 1949(7):32-7.
Hirsch FR et al., "Early Detection of Lung Cancer: Clinical Perspectives of Recent Advances in Biology and Radiology", Clin Cancer Res, Jan. 2001, 7(1):5-22.
International Searching Authority, International Preliminary Report on Patentability (Form PCT/ISA/237) for International Patent Application No. PCT/US2014/029224, (Butkowskyj-Wakiw T), completed on Oct. 28, 2014 (Oct. 28, 2014), dated Nov. 4, 2014 and issued on Sep. 15, 2015 (5 pages).
International Searching Authority, International Search Report (Form PCT/ISA/210) for International Patent Application No. PCT/US2014/029224, (Butkowskyj-Wakiw T), completed on Oct. 28, 2014 (Oct. 28, 2014) and dated Nov. 4, 2014 (4 pages).
Izuishi K et al., "Detection of Bile Duct Cancer by Autofluorescence Cholangioscopy: A Pilot Study", Hepatogastroenterology, Mar.-Apr. 1999, 46(26):804-7.
Koo V et al., "Non-Invasive in vivo Imaging in Small Animal Research", Cell Oncol, 2006 (2006), 28(4):127-39.
Korlach J et al., "Characterization of Lipid Bilayer Phases by Confocal Microscopy and Fluorescence Correlation Spectroscopy", Proc Natl Acad Sci USA, Jul. 20, 1999 (Jul. 20, 1999), 96(15):8461-6.
Kriegmair M et al., "5-Aminolevulinic Acid-Induced Fluorescence Endoscopy for the Detection of Lower Urinary Tract Tumors", Urol Int, 1999, 63(1):27-31.
Major AL et al., "In vivo Fluorescence Detection of Ovarian Cancer in the NuTu-19 Epithelial Ovarian Cancer Animal Model Using 5-aminolevulinic Acid (ALA)", Gynecol Oncol, Jul. 1997, 66(1):122-32.
Monsky WL et al., "Augmentation of Transvascular Transport of Macromolecules and Nanoparticles in Tumors Using Endothelial Growth Factor", Cancer Res, Aug. 15, 1999, 59(16):4129-35.
Mujumder RB et al., "Cyanine Dye Labelling Reagents: Sulfoindocyanine Succinimidyl Esters", Bioconj Chem, Mar.-Apr. 1993, 4(2):105-11.
Mycek MA et al., 'Colonic Polyp Differentiation Using Time-Resolved Autofluorescence Spectroscopy,' Gastrointest Endosc, Oct. 1998, 48(4):390-4.
Ntziachristos V et al., "Concurrent MRI and Diffuse Optical Tomography of Breast After Indocyanine Green Enhancement", Proc Natl Acad Sci USA, Mar. 14, 2000, 97(6):2767-72.
Ntziachristos V et al., "Fluorescence Imaging with Near-Infrared Light: New Technological Advances that Enable in vivo Molecular Imaging", Eur Radiol, Jul. 19, 2002 (ePub), 13(1):195-208.
Ntziachristos V et al., "Fluorescence Molecular Tomography Resolves Protease Activity in vivo", Nat Med, Jun. 24, 2002 (ePub), 8(7):757-60.
Ntziachristos V, "Fluorescence Molecular Imaging", Annu Rev Biomed Eng, 2006, 8:1-33.
Perez JM et al., "Magnetic Relaxation Switches Capable of Sensing Molecular Interactions", Nat Biotechnol, Jul. 22, 2002 (ePub), 20(8):816-20.
Rajadhyaksha M et al., "In vivo Confocal Scanning Laser Microscopy of Human Skin: Melanin Provides Strong Contrast", J Invest Dermatol, Jun. 1995, 104(6):946-52.
Rao J et al., "Fluorescence Imaging in vivo: Recent Advances", Curr Opin Biotechnol, Jan. 17, 2007 (ePub), 18(1):17-25.
Riedl CR et al., "Fluorescence Detection of Bladder Tumors with 5-amino-levulinic Acid", J Endourol, Dec. 1999, 13(10):755-9.
Siegel A et al., "Design and Evaluation of a Continuous-Wave Diffuse Optical Tomography System", Opt Express, Apr. 12, 1999, 4(8):287-98.
Stepp H et al., "Fluorescence Endoscopy of Gastrointestinal Diseases: Basic Principles, Techniques, and Clinical Experience", Endoscopy, May 1998, 30(4):379-86.
Tearney GJ et al., "Images in Cardiovascular Medicine, Catheter-Based Optical Imaging of a Human Coronary Artery", Circulation, Dec. 1, 1996, 94(11):3013.
Tearney GJ et al., "In vivo Endoscopic Optical Biopsy with Optical Coherence Tomography", Science, Jun. 27, 1997, 276(5321):2037-9.
Ward HA, 'New Laser Techniques for Diagnosis and Treatment of Deep-Seated Brain Lesions,' J Laser Appl, Oct. 1998, 10(5):224-8.
Weissleder R, "A Clearer Vision for in vivo Imaging", Nat Biotechnol, Apr. 2001 (Apr. 2001), 19(4):316-7.

* cited by examiner

4,4-DISUBSTITUTED CYCLOHEXYL BRIDGED HEPTAMETHINE CYANINE DYES AND USES THEREOF

CROSS REFERENCE TO RELATED APPLICATIONS

This application is a divisional of U.S. patent application Ser. No. 14/215,930, filed Mar. 17, 2014, which claims priority to and the benefit of U.S. Provisional Patent Application No. 61/798,562, filed on Mar. 15, 2013, the contents of each of which are incorporated herein by reference herein in their entireties.

FIELD OF THE INVENTION

The invention provides compositions and methods for new fluorescent dyes that represent a polymethine bridge comprising a 4,4-disubstituted cyclohexyl bridged moiety. The new compositions generally contain multiple sulfonic acid or sulfonate groups that render the dye with high hydrophilicity, which can be used in various medical, diagnostic and biological applications.

BACKGROUND

Optical imaging methods offer a number of advantages over other imaging methods. Such imaging typically uses light in the red and near-infrared (NIR) range (600-1200 nm) to maximize tissue penetration and minimize absorption from natural biological absorbers such as hemoglobin and water. Optical imaging may provide high sensitivity, does not require exposure of test subjects or laboratory personnel to ionizing radiation, can allow for simultaneous use of multiple, distinguishable probes (which may be important in molecular imaging), and offers high temporal and spatial resolution, which is important in functional imaging and in vivo microscopy, respectively.

In fluorescence imaging, filtered light or a laser with a defined bandwidth is used as a source of excitation light. The excitation light travels through body tissue, and when the excitation light encounters a reporter molecule (for example, a contrast agent or imaging probe), the light is absorbed. The reporter molecule then emits light that has detectably different properties from the excitation light. The resulting emitted light then can be used to construct an image. Most optical imaging techniques have relied on the use of organic and inorganic fluorescent dyes as the reporter molecule.

Fluorescent dyes are generally known and used for fluorescence labeling and detection of various biological and non-biological materials by procedures such as fluorescence microscopy, fluorescence immunoassay, and flow cytometry. A typical method for labeling such materials with fluorescent dyes is to create a fluorescent complex by means of bonding between suitable groups on the dye molecule and compatible groups on the material to be labeled. In this way, materials such as cells, tissues, amino acids, proteins, antibodies, drugs, hormones, nucleotides, nucleic acids, lipids and polysaccharides and the like may be chemically labeled and detected or quantified, or may be used as fluorescent probes which can bind specifically to target materials and detected by fluorescence detection methods. Brightly fluorescent dyes permit detection or localization of the attached materials with great sensitivity.

There is a need for detectable labels for biological and biomedical research. Dyes that work well for quenched probes for use in vivo are not always effective at in vitro applications. In some cases, the presence of more than one of these fluorophores on a protein or biomolecule results in significant quenching which interferes with detection. There is a need for dyes that will allow for both in vitro and in vivo uses and not over-quench the molecule. Highly soluble, hydrophilic fluorescent dyes would also enable tracking the movement and function of labeled cells, proteins, and other biomolecules of interest. A new class of dyes that do not over-quench in vivo or in vitro would increase the tools available for biological research.

Notwithstanding, there is an ongoing need for new dyes that can be used in various medical, diagnostic and biological applications.

SUMMARY OF THE INVENTION

The invention is based, in part, upon the discovery that it is possible to produce new fluorescent dyes with a polymethine bridge comprising a 4,4-disubstituted cyclohexyl bridged moiety. These dyes can be used in a variety of in vitro and in vivo imaging applications.

In certain embodiments, compounds of the invention can be represented by the Formula (II)

$$Z^1\text{-(PMB)-}Z^2 \qquad \text{(II), and salts thereof,}$$

wherein, $Z^1$ and $Z^2$ each independently can be selected from a substituted or unsubstituted indolinium or a benzindolinium ring and PMB represents a polymethine bridge comprising a 4,4-disubstituted cyclohexyl bridged moiety. In other embodiments, the compounds have an absorption and emission wavelengths in the range from about 500 nm to about 1100 nm, preferably in the range from about 600 nm to about 900 nm. In certain embodiments, the dyes absorb and/or emit light having a wavelength in the range from about 600 nm to about 850 nm, from about 650 nm to about 900 nm, or from about 650 nm to about 850 nm.

In one aspect, the invention provides a family of fluorochrome compounds that can be generally represented by Formula I,

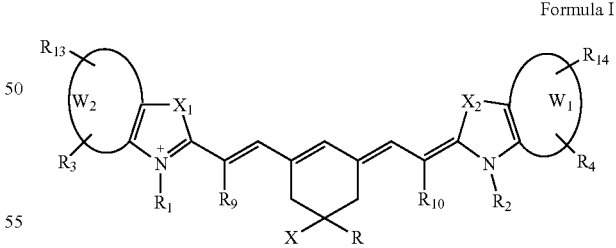

Formula I

In certain embodiments, the invention is a biocompatible fluorescent molecule represented by the formula III: $[BM]_n\text{-}F_m$, wherein BM is a biomolecule, and F is a fluorophore as described previously. In other embodiments, the invention is a biocompatible fluorescent biomolecule represented by any one of the following structural formulae IVa-IVd, wherein BM is a biomolecule Biomolecule attached fluorophores

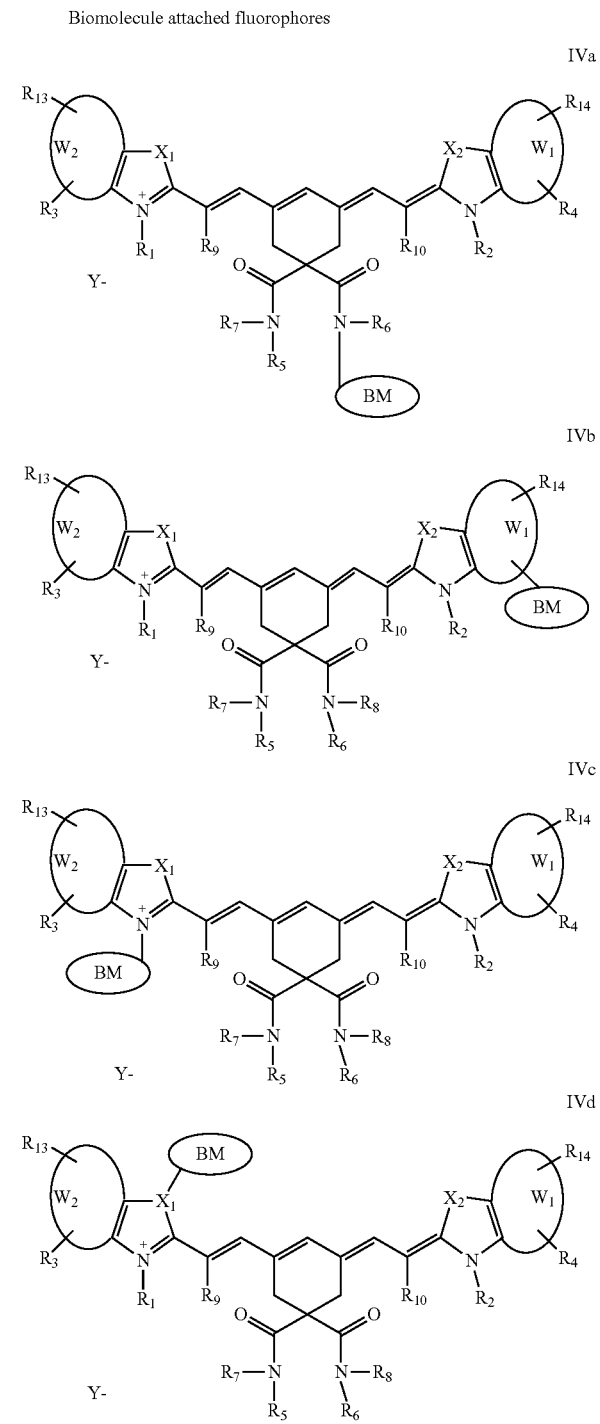

In another aspect, the invention provides an in vivo optical imaging method. The method comprises the steps of (a) administering to a subject, such as an animal or human, a fluorochrome compound of the invention, (b) allowing the fluorochrome compound to distribute within the subject or to contact or interact with a biological target, (c) exposing the subject to electromagnetic radiation, for example, light, of a wavelength absorbable by the fluorochrome compound, and (d) detecting an optical signal emitted by the fluorochrome compound, for example, with an endoscope, catheter, tomographic system, a planar or reflectance system, hand-held optical imaging system, or intraoperative systems and microscope. The signal emitted by the compound can be used to construct an image, for example, a tomographic image, of a region or structure to be imaged. It is understood that the fluorochrome compound can comprise a fluorochrome dye chemically linked to a biomolecule.

The foregoing steps may be repeated at predetermined intervals thereby permitting the evaluation of the emitted signals of the fluorescent compound in the subject over time. In certain embodiments two or more compounds whose signal properties are distinguishable can be administered to the subject and their emission properties can be used to image two or more features in the subject.

The disclosed methods can be used to detect and/or monitor a disease, for example, bone disease, cancer, cardiovascular disease, dermatological disease, environmental disease, immunologic disease, infectious disease, inflammation, inherited disease, metabolic disease, neurodegenerative disease, ophthalmic disease, and respiratory disease.

In certain embodiments, cells are labeled with a fluorochrome compound described herein and the resulting labeled cells administered to the subject. The signal emitted by the fluorochrome compound can be used to monitor transport and localization of the cells or to evaluate the efficacy of a cell therapy.

In another aspect, the invention provides an in vitro optical imaging method. The method comprises the steps of (a) contacting a sample, for example, a biological sample, with the fluorochrome compound of the invention, (b) allowing the fluorochrome compound to become activated by or to bind to a biological target; (c) optionally, removing unbound fluorochrome compound; (d) exposing the sample to electromagnetic radiation, for example, light, of a wavelength absorbable by the fluorochrome compound; and (e) detecting signal emitted from the fluorochrome compound thereby to determine whether the fluorochrome compound has been activated by or bound to the biological target.

BRIEF DESCRIPTION OF THE DRAWINGS

FIG. 1A is a graph of fluorescence emitted by the BSA-conjugate of Compound 1b. FIG. 1B depicts fluorescence absorbance of BSA-conjugate of Compound 1b conjugated to BSA.

DETAILED DESCRIPTION OF THE INVENTION

Figure 1A:
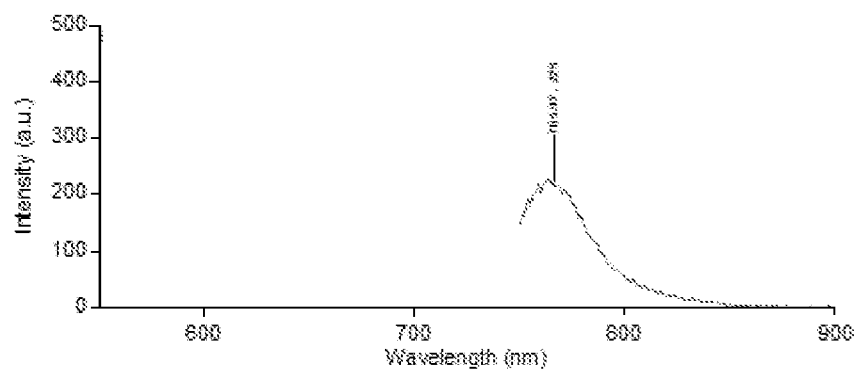
FIGS. 1A and 1B depict the fluorescence and absorbance spectra for Bovine Serum Albumin (BSA)-conjugated dyes of the present invention.

The present invention provides a family of fluorochrome compounds (dyes) that absorb and/or emit light having a wavelength in the range from about 500 nm to about 1100 nm, more preferably in the range from about 600 nm to about 900 nm. In certain embodiments, the dyes absorb and/or emit light having a wavelength in the range from about 600 nm to about 850 nm, from about 650 nm to about 900 nm, or from about 650 nm to about 850 nm. The fluorochrome compounds are particularly useful in a variety of in vitro and in vivo imaging applications.

In certain embodiments, the fluorochrome compounds of the invention can be represented by the formula $Z^1$—PMB-$Z^2$, and salts thereof, wherein $Z^1$ and $Z^2$ each independently represent the same or different polycyclic groups containing a heterocyclic moiety, and PMB represents a polymethine bridge comprising a 4,4-disubstituted cyclohexyl bridged moiety. The fluorochrome compounds will be discussed in more detail herein below. However, before further description of the present invention, certain terms employed in the specification, examples and appended claims are collected together in the following section.

I. Definitions

The definitions listed herein should be read in light of the remainder of the disclosure and understood as by a person of skill in the art. Unless defined otherwise, all technical and scientific terms used herein have the same meaning as commonly understood by a person of ordinary skill in the art to which this invention belongs.

"Chemically linked" means connected by an attractive force between atoms strong enough to allow the combined aggregate to function as a unit. This includes, but is not limited to, chemical bonds such as covalent bonds, non-covalent bonds such as ionic bonds, metallic bonds, and bridge bonds, hydrophobic interactions, hydrogen bonds, and van der Waals interactions. This also includes cross-linking or caging.

The term "alkyl" is art-recognized, and includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., $C_1$-$C_{30}$ for straight chain, $C_3$-$C_{30}$ for branched chain), and alternatively, about 20 or fewer. Likewise, cycloalkyls have from about 3 to about 10 carbon atoms in their ring structure, and alternatively about 5, 6 or 7 carbons in the ring structure. The term "alkyl" also includes halosubstituted alkyls.

Moreover, the term "alkyl" includes "substituted alkyls", which refers to alkyl moieties having substituents replacing a hydrogen on one or more carbons of the hydrocarbon backbone. Such substituents may include, for example, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain may themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —CN and the like. Exemplary substituted alkyls are described below. Cycloalkyls may be further substituted with alkyls, alkenyls, alkoxys, alkylthios, aminoalkyls, carbonyl-substituted alkyls, —CN, and the like. In certain embodiments, the alkyl is unsubstituted. In certain embodiments, the alkyl is a straight or branched chain alkyl group that is unsubstituted.

The term "haloalkyl" refers to an alkyl group as defined above except that one or more hydrogen atoms have been replaced with a halogen.

The term "alkylene" refers to a diradical of a straight or branched chain alkyl group that is unsubstituted.

The terms "aralkyl" and "alkylaryl" are art-recognized and refer to an alkyl group substituted with an aryl group (e.g., an aromatic or heteroaromatic group).

The terms "alkenyl" and "alkynyl" are art-recognized and refer to unsaturated aliphatic groups analogous in length and possible substitution to the alkyls described above, but that contain at least one double or triple bond, respectively.

The term "heteroatom" is art-recognized and refers to an atom of any element other than carbon or hydrogen. Illustrative heteroatoms include boron, nitrogen, oxygen, phosphorus, sulfur and selenium.

The term "aryl" is art-recognized and refers to 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "heteroaryl" or "heteroaromatics." The aromatic ring may be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, aryls and/or heterocyclyls.

The terms "heterocyclyl," "heterocyclic group" or "heterocyclic moiety" are art-recognized and refer to 3- to about 10-membered ring structures, alternatively 3- to about 7-membered rings, whose ring structures include one to four heteroatoms. Heterocycles may also be polycycles. Heterocyclyl groups include, for example, thiophene, thianthrene, furan, pyran, isobenzofuran, chromene, xanthene, phenoxanthene, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring may be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The terms "polycyclyl," "polycyclic group" or "polycyclo moiety" are art-recognized and refer to two or more rings (e.g., cycloalkyls, cycloalkenyls, cycloalkynyls, aryls and/or heterocyclyls) in which two or more carbons are common to two adjoining rings, e.g., the rings are "fused rings." Rings that are joined through non-adjacent atoms are termed "bridged" rings. Each of the rings of the polycycle may be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The term "nitro" is art-recognized and refers to —NO$_2$; the term "halogen" is art-recognized and refers to —F, —Cl, —Br or —I; the term "sulfhydryl" is art-recognized and refers to —SH; the term "hydroxyl" means —OH; and the term "sulfonyl" is art-recognized and refers to —SO$_2^-$. "Halide" designates the corresponding anion of the halogens, and "pseudohalide" has the definition set forth in "*Advanced Inorganic Chemistry*" by Cotton and Wilkinson.

The terms "amine" and "amino" are art-recognized and refer to both unsubstituted and substituted amines, e.g., a moiety that may be represented by the general formulas:

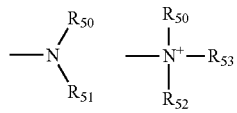

wherein $R_{50}$, $R_{51}$, $R_{52}$ and $R_{53}$ each independently represent a hydrogen, an alkyl, an alkenyl, —(CH$_2$)$_m$—R$_{61}$, or $R_{50}$ and $R_{51}$, taken together with the N atom to which they are attached complete a heterocycle having from 4 to 8 atoms in the ring structure; $R_{61}$ represents an aryl, a cycloalkyl, a cycloalkenyl, a heterocycle or a polycycle; and m is zero or an integer in the range of 1 to 8. In certain embodiments, only one of $R_{50}$ or $R_{51}$ may be a carbonyl, e.g., $R_{50}$, $R_{51}$ and the nitrogen together do not form an imide. In other embodiments, $R_{50}$ and $R_{51}$ (and optionally $R_{52}$) each independently represent a hydrogen, an alkyl, an alkenyl, or —(CH$_2$)$_m$—R$_{61}$. Thus, the term "alkylamine" includes an amine group, as defined above, having a substituted or unsubstituted alkyl attached thereto, i.e., at least one of $R_{50}$ and $R_{51}$ is an alkyl group.

The term "acylamino" is art-recognized and refers to a moiety that may be represented by the general formula:

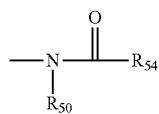

wherein $R_{50}$ is as defined above, and $R_{54}$ represents a hydrogen, an alkyl, an alkenyl or —(CH$_2$)$_m$—R$_{61}$, where m and $R_{61}$ are as defined above.

The term "amido" is art recognized as an amino-substituted carbonyl and includes a moiety that may be represented by the general formula:

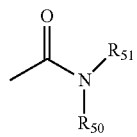

wherein $R_{50}$ and $R_{51}$ are as defined above. Certain embodiments of the amide in the present invention will not include imides which may be unstable.

The term "alkylthio" refers to an alkyl group, as defined above, having a sulfur radical attached thereto. In certain embodiments, the "alkylthio" moiety is represented by one of —S-alkyl, —S-alkenyl, —S-alkynyl, and —S—(CH$_2$)$_m$—R$_{61}$, wherein m and $R_{61}$ are defined above. Representative alkylthio groups include methylthio, ethylthio, and the like.

The term "carbonyl" is art recognized and includes such moieties as may be represented by the general formulas:

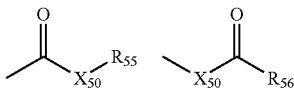

wherein $X_{50}$ is a bond or represents an oxygen or a sulfur, and $R_{55}$ and $R_{56}$ represents a hydrogen, an alkyl, an alkenyl, —(CH$_2$)$_m$—R$_{61}$ or a pharmaceutically acceptable salt, $R_{56}$ represents a hydrogen, an alkyl, an alkenyl or —(CH$_2$)$_m$—R$_{61}$, where m and $R_{61}$ are defined above. Where $X_{50}$ is an oxygen and $R_{55}$ or $R_{56}$ is not hydrogen, the formula represents an "ester." Where $X_{50}$ is an oxygen, and $R_{55}$ is as defined above, the moiety is referred to herein as a carboxyl group, and particularly when $R_{55}$ is a hydrogen, the formula represents a "carboxylic acid." Where $X_{50}$ is an oxygen, and $R_{56}$ is hydrogen, the formula represents a "formate." In general, where the oxygen atom of the above formula is replaced by sulfur, the formula represents a "thiolcarbonyl" group. Where $X_{50}$ is a sulfur and $R_{55}$ or $R_{56}$ is not hydrogen, the formula represents a "thiolester." Where $X_{50}$ is a sulfur and $R_{55}$ is hydrogen, the formula represents a "thiolcarboxylic acid." Where $X_{50}$ is a sulfur and $R_{56}$ is hydrogen, the formula represents a "thiolformate." On the other hand, where $X_{50}$ is a bond, and $R_{55}$ is not hydrogen, the above formula represents a "ketone" group. Where $X_{50}$ is a bond, and $R_{55}$ is hydrogen, the above formula represents an "aldehyde" group.

The terms "alkoxyl" or "alkoxy" are art-recognized and refer to an alkyl group, as defined above, having an oxygen attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, —O—(CH$_2$)$_m$—R$_{61}$, where m and $R_{61}$ are described above.

The term "sulfonate" is art recognized and refers to a moiety that may be represented by the general formula:

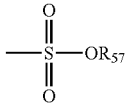

in which $R_{57}$ is an electron pair, hydrogen, alkyl, cycloalkyl, or aryl.

The term "sulfate" is art recognized and includes a moiety that may be represented by the general formula:

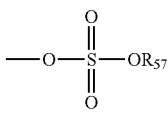

in which $R_{57}$ is as defined above.

The term "sulfonamido" is art recognized and includes a moiety that may be represented by the general formula:

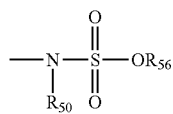

in which $R_{50}$ and $R_{56}$ are as defined above.

The term "sulfamoyl" is art-recognized and refers to a moiety that may be represented by the general formula:

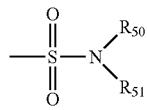

in which $R_{50}$ and $R_{51}$ are as defined above.

The term "sulfonyl" is art-recognized and refers to a moiety that may be represented by the general formula:

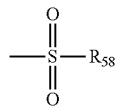

in which $R_{58}$ is one of the following: hydrogen, alkyl, alkenyl, alkynyl, cycloalkyl, heterocyclyl, aryl or heteroaryl.

The term "sulfoxido" is art-recognized and refers to a moiety that may be represented by the general formula:

in which $R_{58}$ is defined above.

The term "phosphoryl" is art-recognized and may in general be represented by the formula:

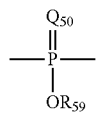

wherein $Q_{50}$ represents S or O, and $R_{59}$ represents hydrogen, a lower alkyl or an aryl. When used to substitute, e.g., an alkyl, the phosphoryl group of the phosphorylalkyl may be represented by the general formulas:

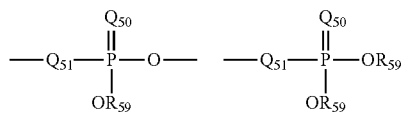

wherein $Q_{50}$ and $R_{59}$, each independently, are defined above, and $Q_{51}$ represents O, S or N. When $Q_{50}$ is S, the phosphoryl moiety is a "phosphorothioate".

The term "phosphoramidite" is art-recognized and may be represented in the general formulas:

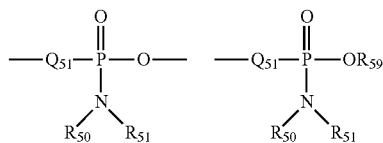

wherein $Q_{51}$, $R_{50}$, $R_{51}$ and $R_{59}$ are as defined above.

The term "phosphonamidite" is art-recognized and may be represented in the general formulas:

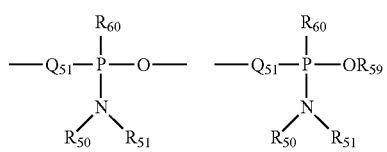

wherein $Q_{51}$, $R_{50}$, $R_{51}$ and $R_{59}$ are as defined above, and $R_{60}$ represents a lower alkyl or an aryl.

Analogous substitutions may be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

The definition of each expression, e.g., alkyl, m, n, and the like, when it occurs more than once in any structure, is intended to be independent of its definition elsewhere in the same structure.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, or other reaction.

The term "substituted" is also contemplated to include all permissible substituents of organic compounds. Exemplary substituents include, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, and the like. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The term "polymethine bridge" refers to a conjugated double bond methylene chain comprising an odd number of carbons. Such a bridge can include a ring structure as part of the conjugated double bond methylene chain.

The term "physiologically acceptable carrier" refers to a carrier in which one or more of the compounds of the invention are dispersed, dissolved, suspended, admixed and physiologically tolerable, i.e., can be administered to, in, or on the subject's body without undue discomfort, or irritation, or toxicity.

Throughout the description, where compositions are described as having, including, or comprising specific components, it is contemplated that compositions also consist essentially of, or consist of, the recited components. Similarly, where processes are described as having, including, or comprising specific process steps, the processes also consist essentially of, or consist of, the recited processing steps. Further, it should be understood that the order of steps or order for performing certain actions are immaterial so long as the invention remains operable. Moreover, two or more steps or actions may be conducted simultaneously.

II. Fluorochrome Compounds of the Invention

One aspect of the invention provides a fluorescent compound represented by Formula I-A:

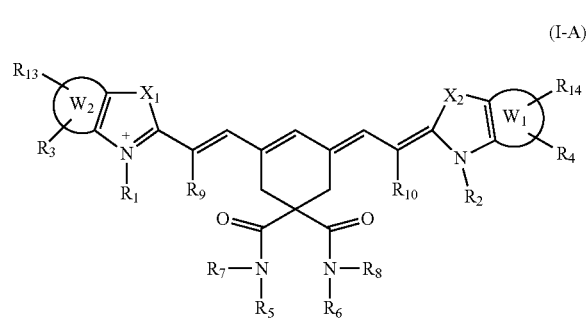

(I-A)

or a salt thereof, wherein:

$X_1$ and $X_2$ are each independently O, S, Se, or $C(C_{1-4}\text{ alkyl})_2$;

$W_1$ and $W_2$ are a benzo, naphtha, or pyridyl ring;

$R_1$ and $R_2$ are independently hydrogen or $-C_1\text{-}C_{10}$ alkyl optionally substituted with one or two substituents independently selected from the group consisting of halogen, $-SO_3H$, $-SO_3^-$, $-COOH$, $-CO_2^-$, and $-OH$;

$R_5$, $R_6$, $R_7$ and $R_8$ are each independently H or $-C_1\text{-}C_{22}$ alkylene-$X_3$;

$R_3$, $R_4$, $R_{13}$ and $R_{14}$ are each independently H, $-C_1\text{-}C_{22}$ alkylene-$X_3$, $-SO_3H$, $-SO_3^-$, $-SO_2N(R_{12})$-alkylene-$X_3$, halogen, or $-NO_2$;

$X_3$ represents independently for each occurrence H, halogen, $-CH_3$, $-SO_3H$, $-SO_3^-$, $-COOH$, $-CO_2^-$, $-NCS$, $-NCO$, N-hydroxysuccinimidyl ester, N-hydroxysulfosuccinimidyl ester, $-OH$, $-SH$, maleimide, phthalimide, $-NHCO-(CH_2)_m$-(halogen), $-CONHNH_2$, $-CN$, $-NH_2$, $-NO_2$, $-CON(H)R_{12}$, alkynyl, $-N_3$, a polyethyl glycol, optionally substituted aryl, or optionally substituted heterocyclyl;

$R_9$ and $R_{10}$ are hydrogen, halogen, or alkyl, or $R_1$ and $R_9$ or $R_2$ and $R_{10}$ are taken together with their interconnecting atoms to form a 5-, 6- or 7-membered ring;

$R_{12}$ represents independently for each occurrence hydrogen or alkyl;

m represents independently for each occurrence 0, 1, 2, 3, or 4; and n represents independently for each occurrence 1-10.

In certain embodiments, $X_1$ and $X_2$ are $C(CH_3)_2$. In certain embodiments, $W_1$ and $W_2$ are a benzo ring. In certain embodiments, $W_1$ and $W_2$ are a naptha ring. In certain embodiments, $R_1$ and $R_2$ are independently $-C_1\text{-}C_{10}$ alkyl optionally substituted with $-SO_3H$ or $-SO_3^-$. In certain embodiments, $R_1$ and $R_2$ are independently $C_1\text{-}C_6$ alkyl. In certain embodiments, $R_3$, $R_4$, $R_{13}$ and $R_{14}$ are each independently H, $-SO_3H$, or $-SO_3$. In certain embodiments, $R_7$ is hydrogen. In certain embodiments, $R_9$ and $R_{10}$ are hydrogen.

In certain embodiments, $R_5$ and $R_6$ are each independently $-C_1\text{-}C_{22}$ alkylene-$X_3$. In certain embodiments, $R_5$ and $R_6$ are each independently $-C_2\text{-}C_8$ alkylene-$X_3$. In certain embodiments, $R_5$ and $R_6$ are each independently $-C_2\text{-}C_8$ alkylene substituted by $-SO_3H$, $-SO_3^-$, or $-COOH$. In certain embodiments, $R_7$ and $R_8$ are hydrogen.

Another aspect of the invention provides a fluorescent compound represented by Formula I-B:

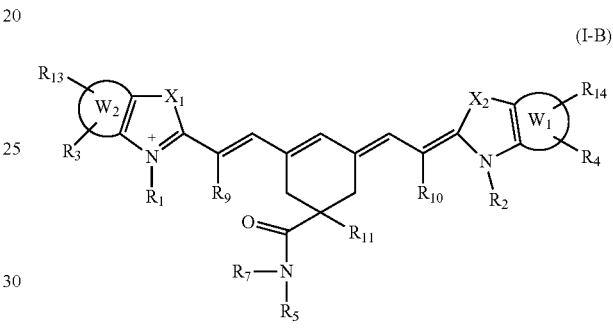

(I-B)

or a salt thereof, wherein:

$X_1$ and $X_2$ are each independently O, S, Se, or $C(C_{1-4}\text{ alkyl})_2$;

$W_1$ and $W_2$ are a benzo, naphtha, or pyridyl ring;

$R_1$ and $R_2$ are independently hydrogen or $-C_1\text{-}C_{10}$ alkyl optionally substituted with one or two substituents independently selected from the group consisting of halogen, $-SO_3H$, $-SO_3^-$, $-COOH$, $-CO_2^-$, and $-OH$;

$R_5$ and $R_7$ are each independently hydrogen or $-C_1\text{-}C_{22}$ alkylene-$X_3$;

$R_3$, $R_4$, $R_{13}$ and $R_{14}$ are each independently hydrogen, $-C_1\text{-}C_{22}$ alkylene-$X_3$, $-SO_3H$, $-SO_3^-$, $-SO_2N(R_{12})$-alkylene-$X_3$, halogen, or $-NO_2$;

$X_3$ represents independently for each occurrence H, halogen, $-CH_3$, $-SO_3H$, $-SO_3^-$, $-COOH$, $-CO_2^-$, $-NCS$, $-NCO$, N-hydroxysuccinimidyl ester, N-hydroxysulfosuccinimidyl ester, $-OH$, $-SH$, maleimide, phthalimide, $-NHCO-(CH_2)_m$-(halogen), $-CONHNH_2$, $-CN$, $-NH_2$, $-NO_2$, $-CON(H)R_{12}$, alkynyl, $-N_3$, a polyethyl glycol, optionally substituted aryl, or optionally substituted heterocyclyl;

$R_9$ and $R_{10}$ are H, halogen, or alkyl, or $R_1$ and $R_9$ or $R_2$ and $R_{10}$ are taken together with their interconnecting atoms to form a 5-, 6- or 7-membered ring;

$R_{11}$ is $-COOH$, $-CN$, halogen, $-NO_2$, $-C(O)$-haloalkyl, haloalkyl, $-COOR_{15}$, $-CON(H)R_{15}$, or $-CO(CH_2)_nR_{15}$;

$R_{12}$ represents independently for each occurrence hydrogen or alkyl;

$R_{15}$ is H, $-COOH$, $-SO_3H$, $-NH_2$, $-SH$, alkyl, or aryl optionally substituted with $X_3$ and/or a polyethylene glycol;

m represents independently for each occurrence 0, 1, 2, 3, or 4; and n represents independently for each occurrence 1-10.

In certain embodiments, $X_1$ and $X_2$ are $C(CH_3)_2$. In certain embodiments, $W_1$ and $W_2$ are a benzo ring. In certain embodiments, $W_1$ and $W_2$ are a naptha ring. In certain embodiments, $R_1$ and $R_2$ are independently —$C_1$-$C_{10}$ alkyl optionally substituted with —$SO_3H$ or —$SO_3^-$. In certain embodiments, $R_1$ and $R_2$ are independently $C_1$-$C_6$ alkyl. In certain embodiments, $R_3$, $R_4$, $R_{13}$ and $R_{14}$ are each independently H, —$SO_3H$, or —$SO_3$. In certain embodiments, $R_7$ is hydrogen. In certain embodiments, $R_9$ and $R_{10}$ are hydrogen.

In certain embodiments, $R_5$ is —$C_1$-$C_{22}$ alkylene-$X_3$, and $R_7$ is hydrogen. In certain embodiments, $R_5$ is —$C_2$-$C_8$ alkylene-$X_3$, and $R_7$ is hydrogen. In certain embodiments, $R_5$ is —$C_2$-$C_8$ alkylene substituted by —$SO_3H$, —$SO_3^-$, or —COOH, and $R_7$ is hydrogen.

Another aspect of the invention provides a fluorescent compound represented by Formula I-C:

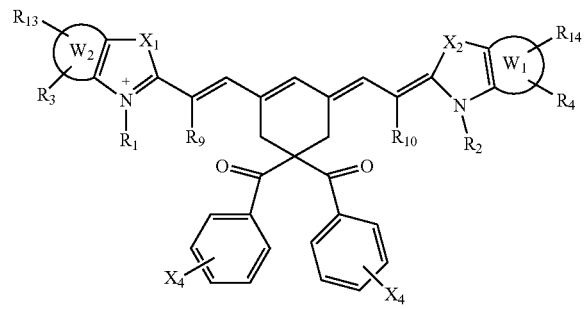

(I-C)

or a salt thereof, wherein:

$X_1$ and $X_2$ are each independently O, S, Se, or $C(C_{1-4}$ alkyl$)_2$;

$R_1$ and $R_2$ are independently hydrogen or —$C_1$-$C_{10}$ alkyl optionally substituted with one or two substituents independently selected from the group consisting of halogen, —$SO_3H$, —$SO_3^-$, —COOH, —$CO_2^-$, and —OH;

$R_3$, $R_4$, $R_{13}$ and $R_{14}$ are each independently hydrogen, —$C_1$-$C_{22}$ alkylene-$X_3$, —$SO_3H$, —$SO_3^-$, —$SO_2N(R_{12})$-alkylene-$X_3$, halogen, or —$NO_2$;

$X_3$ represents independently for each occurrence H, halogen, —$CH_3$, —$SO_3H$, —$SO_3^-$, —COOH, —$CO_2^-$, —NCS, —NCO, N-hydroxysuccinimidyl ester, N-hydroxysulfosuccinimidyl ester, —OH, —SH, maleimide, phthalimide, —NHCO—$(CH_2)_m$-(halogen), —$CONHNH_2$, —CN, —$NH_2$, —$NO_2$, —$CON(H)R_{12}$, alkynyl, —$N_3$, a polyethyl glycol, optionally substituted aryl, or optionally substituted heterocyclyl;

$X_4$ represents independently for each occurrence hydrogen, halogen, —$SO_3H$, —$SO_3^-$, —COOH, or —$CO_2^-$;

$R_9$ and $R_{10}$ are H, halogen, or alkyl, or $R_1$ and $R_9$ or $R_2$ and $R_{10}$ are taken together with their interconnecting atoms form a 5-, 6- or 7-membered ring;

$R_{12}$ represents independently for each occurrence hydrogen or alkyl;

m represents independently for each occurrence 0, 1, 2, 3, or 4; and n represents independently for each occurrence 1-10.

In certain embodiments, $X_1$ and $X_2$ are $C(CH_3)_2$. In certain embodiments, $W_1$ and $W_2$ are a benzo ring. In certain embodiments, $W_1$ and $W_2$ are a naptha ring. In certain embodiments, $R_1$ and $R_2$ are independently —$C_1$-$C_{10}$ alkyl optionally substituted with —$SO_3H$ or —$SO_3^-$. In certain embodiments, $R_1$ and $R_2$ are independently $C_1$-$C_6$ alkyl. In certain embodiments, $R_3$, $R_4$, $R_{13}$ and $R_{14}$ are each independently H, —$SO_3H$, or —$SO_3$. In certain embodiments, $R_7$ is hydrogen. In certain embodiments, $R_9$ and $R_{10}$ are hydrogen.

Another aspect of the invention provides a fluorescent compound represented by Formula I-D:

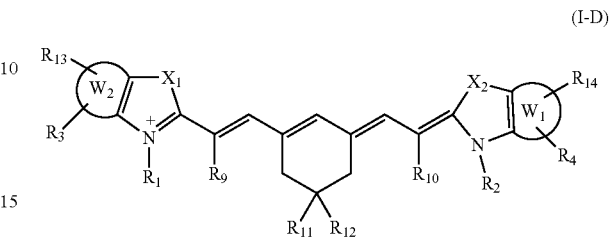

(I-D)

or a salt thereof, wherein:

$X_1$ and $X_2$ are each independently O, S, Se, or $C(C_{1-4}$ alkyl$)_2$;

$W_1$ and $W_2$ are a benzo, naphtha, or pyridyl ring;

$R_1$ and $R_2$ are independently hydrogen or —$C_1$-$C_{10}$ alkyl optionally substituted with one or two substituents independently selected from the group consisting of halogen, —$SO_3H$, —COOH, —$CO_2^-$, and —OH;

$R_3$, $R_4$, $R_{13}$ and $R_{14}$ are each independently H, —$C_1$-$C_{22}$ alkylene-$X_3$, —$SO_3H$, —$SO_2N(R_{12})$-alkylene-$X_3$, halogen, or —$NO_2$;

$X_3$ represents independently for each occurrence H, halogen, —$CH_3$, —$SO_3H$, —$SO_3^-$, —COOH, —$CO_2^-$, —NCS, —NCO, N-hydroxysuccinimidyl ester, N-hydroxysulfosuccinimidyl ester, —OH, —SH, maleimide, phthalimide, —NHCO—$(CH_2)_m$-(halogen), —$CONHNH_2$, —CN, —$NH_2$, —$NO_2$, —$CON(H)R_{13}$, alkynyl, —$N_3$, a polyethyl glycol, optionally substituted aryl, or optionally substituted heterocyclyl;

$R_9$ and $R_{10}$ are hydrogen, halogen, or alkyl, or $R_1$ and $R_9$ or $R_2$ and $R_{10}$ are taken together with their interconnecting atoms to form a 5-, 6- or 7-membered ring;

$R_{11}$ and $R_{12}$ are each independently alkyl, haloalkyl, aryl, aralkyl, cyano, halogen, nitro, —COOH, —C(O)-haloalkyl, —C(O)-aryl, —$C(O)OR_{15}$, —$CON(H)R_{15}$, —$(CH_2)_nC(O)OR_{15}$, —$(CH_2)_nCONHR_{15}$, —$CO(CH_2)_nR_{15}$, —$(CH_2)_nSO_3H$, or —$(CH_2)_nSO_3^-$, $R_{13}$ represents independently for each occurrence hydrogen or alkyl;

$R_{15}$ represents independently for each occurrence H, —COOH, —$SO_3H$, —$NH_2$, —SH, alkyl, a polyethylene glycol, or aryl which may be optionally substituted with $X_3$ and/or a polyethylene glycol;

m represents independently for each occurrence 0, 1, 2, 3, or 4; and n represents independently for each occurrence 1-10.

In certain embodiments, $X_1$ and $X_2$ are $C(CH_3)_2$. In certain embodiments, $W_1$ and $W_2$ are a benzo ring. In certain embodiments, $W_1$ and $W_2$ are a naptha ring. In certain embodiments, $R_1$ and $R_2$ are independently —$C_1$-$C_{10}$ alkyl optionally substituted with —$SO_3H$ or —$SO_3^-$. In certain embodiments, $R_1$ and $R_2$ are independently $C_1$-$C_6$ alkyl. In certain embodiments, $R_3$, $R_4$, $R_{13}$ and $R_{14}$ are each independently H, —$SO_3H$ or —$SO_3$. In certain embodiments, $R_7$ is hydrogen. In certain embodiments, $R_9$ and $R_{10}$ are hydrogen.

Another aspect of the invention provides a fluorescent compound represented by Formula II:

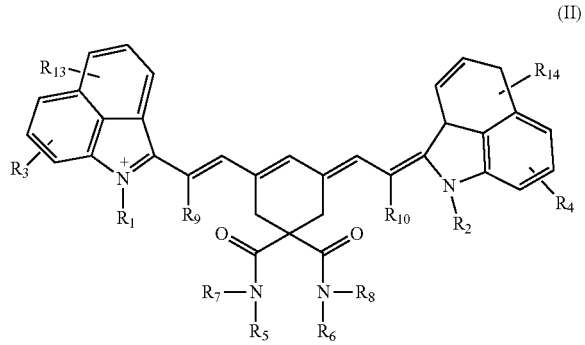
(II)

or a salt thereof, wherein:

$R_1$ and $R_2$ are independently hydrogen or —$C_1$-$C_{10}$ alkyl optionally substituted with one or two substituents independently selected from the group consisting of halogen, —$SO_3H$, —$SO_3^-$, —COOH, —$CO_2^-$, and —OH;

$R_5$, $R_6$, $R_7$ and $R_8$ are each independently H or —$C_1$-$C_{22}$ alkylene-$X_3$;

$R_3$, $R_4$, $R_{13}$ and $R_{14}$ are each independently H, —$C_1$-$C_{22}$ alkylene-$X_3$, —$SO_3H$, —$SO_3^-$, —$SO_2N(R_{12})$-alkylene-$X_3$, halogen, or —$NO_2$;

$X_3$ represents independently for each occurrence H, halogen, —$CH_3$, —$SO_3H$, —$SO_3^-$, —COOH, —$CO_2^-$, —NCS, —NCO, N-hydroxysuccinimidyl ester, N-hydroxysulfosuccinimidyl ester, —OH, —SH, maleimide, phthalimide, —NHCO—$(CH_2)_m$-(halogen), —$CONHNH_2$, —CN, —$NH_2$, —$NO_2$, —CON(H)$R_{12}$, alkynyl, —$N_3$, a polyethyl glycol, optionally substituted aryl, or optionally substituted heterocyclyl;

$R_9$ and $R_{10}$ are hydrogen, halogen, or alkyl, or $R_1$ and $R_9$ or $R_2$ and $R_{10}$ are taken together with their interconnecting atoms to form a 5-, 6- or 7-membered ring;

$R_{12}$ represents independently for each occurrence hydrogen or alkyl;

m represents independently for each occurrence 0, 1, 2, 3, or 4; and n represents independently for each occurrence 1-10.

In certain embodiments, $R_1$ and $R_2$ are independently —$C_1$-$C_{10}$ alkyl optionally substituted with —$SO_3H$ or —$SO_3^-$. In certain embodiments, $R_1$ and $R_2$ are independently —$C_2$-$C_6$ alkyl optionally substituted with —$SO_3H$ or —$SO_3$. In certain embodiments, $R_1$ and $R_2$ are independently $C_1$-$C_6$ alkyl. In certain embodiments, $R_5$ and $R_6$ are each independently —$C_1$-$C_{22}$ alkylene-$X_3$. In certain embodiments, $R_5$ and $R_6$ are each independently —$C_2$-$C_8$ alkylene-$X_3$. In certain embodiments, $R_5$ and $R_6$ are each independently —$C_2$-$C_8$ alkylene substituted by —$SO_3H$, —$SO_3^-$, or —COOH. In certain embodiments, $R_7$ and $R_8$ are hydrogen. In certain embodiments, $R_9$ and $R_{10}$ are hydrogen.

Another aspect of the invention provides compounds represented by the Formula (II)

$Z^1$ and $Z^2$ each independently represent a polycyclic group comprising a heterocyclic moiety. For example, $Z^1$ and $Z^2$ each independently can be selected from a substituted or unsubstituted indolinium or a benzindolinium ring. PMB represents a polymethine bridge comprising a 4,4-disubstituted cyclohexyl bridged moiety. The compounds have an absorption and emission wavelengths in the range from about 500 nm to about 1100 nm, preferably in the range from about 600 nm to about 900 nm. In certain embodiments, the dyes absorb and/or emit light having a wavelength in the range from about 600 nm to about 850 nm, from about 650 nm to about 900 nm, or from about 650 nm to about 850 nm.

$Z^1$, $Z^2$, and/or PMB optionally can include a linker moiety capable of forming a covalent bond, and/or chemical linkage to a biomolecule. Such a linker moiety can include a reactive group that is capable of chemically reacting with a functional group on a different compound to form a covalent linkage, or a functional group that is capable of chemically reacting with a reactive group on different compound to form a covalent linkage. Such a reactive group can include, for example, an electrophile or nucleophile that can form a covalent linkage via exposure to a corresponding functional group that is a nucleophile or electrophile, respectively. Alternatively, the reactive group is a photoactivatable group, and becomes chemically reactive only after illumination with light of an appropriate wavelength. A reaction between the compound of the invention and the biomolecule to be linked can result in one or more atoms of a reactive group incorporated into a new linkage attaching a compound of the invention to the conjugated substance.

Biomolecules contemplated herein include, but are not limited to, proteins (for example, enzymes, hormones, antibodies and antigen binding fragments thereof, and single chain antibodies), peptides, amino acids, glycoproteins, ligands for cell receptors, polysaccharides, carbohydrates, nucleic acids (for example, DNA and RNA), nucleosides, nucleotides, aptamers, peptidyl nucleic acids, cell receptors, enzyme substrates, enzyme cofactors, biotin, hormones, neurotransmitters, growth factors, cytokines, lymphokines, lectins, selectins, lipids, lipid assemblies (for example, micelles or vesicles), and toxins. Other biomolecules can be used, such as those involved in targeting and delivery such as folate-mediated targeting (Leamon & Low, *Drug Discovery Today*, 6:44-51, 2001), transferrin, vitamins, carbohydrates and ligands that target internalizing receptors, including, but not limited to, asialoglycoprotein receptor, somatostatin, nerve growth factor, oxytocin, bombesin, calcitonin, arginine vasopressin, angiotensin II, atrial natriuretic peptide, insulin, glucagons, prolactin, gonadotropin, various opioids and urokinase-type plasminogen activator. Also contemplated are membrane, transmembrane, and nuclear translocation signal sequences, which can be derived from a number of sources including, without limitation, viruses and bacteria. Biomolecules can also include organic molecules, polymers, dendrimers, cells (for example, mammalian cells, non mammalian cells, plant cells, insect cells, embryonic cells), bacteria, bacteriophage, viruses, organisms, particles, microparticles, or nanoparticles. Biomolecules can also include therapeutic drug molecules including but not limited to phototherapy or radiotherapy molecules.

The fluorochrome compounds of the present invention can be used to create one or more of the following types of imaging agents or probes: a molecular probe, an activatable probe, an enzyme-activatable probe, a quantum dot-based imaging probe, a nanoparticle-based imaging probe, a probe targeted to a biomolecule, a wavelength shifting beacon, a multicolor probe, a probe with high binding affinity to a target, a non-specific imaging probe, cell based probe, a dual modality agent, an optical/CT dual modality agent (e.g., an optical agent physically or chemically bound to a CT agent), an optical/MR dual modality agent (e.g., an optical agent physically or chemically bound to an MR agent), an optical/nuclear dual modality agent (e.g., an optical agent physically or chemically bound or with a radioactive atom) and/or any combination thereof.

Compounds of the invention that include a chemically linked biomolecule may have enhanced fluorescence as compared to the compound that is not chemically linked to a biomolecule. In certain embodiments, the fluorescence is enhanced by about 10%, about 25% or about 50% when compared with the unlinked compound. Biomolecules chemically linked to the compounds of the invention may alter or enhance accumulation, biodistribution, elimination, targeting, binding, and/or recognition of the molecules in vivo and/or in vitro.

One or more biomolecules may be chemically linked to $Z^1$, PMB, and/or $Z^2$ via multivalent linkages or linkers containing several reactive functional groups to form a biocompatible fluorescent molecule of the structure $(Z^1\text{-}(PMB)\text{-}Z^2)\text{-}((L)_v(BM)_r)_t$, wherein L is a linker or spacer or multivalent spacer or linker, BM is a biomolecule, $Z^1$, $Z^2$ and PMB are as previously defined, and t=1-6, v=1-500 and r=1-500. $(L)_v$, when v is greater than 1, represents copies of the same linker or a combination of different linkers.

Examples of appropriate linker moieties for compounds of the present invention have been previously described in the literature (see, U.S. Patent Appl. 2002/0064794 (2002); U.S. Pat. Nos. 6,086,737; 6,048,982; 6,747,159; and 6,448,008).

It is understood that more than one fluorochrome compound of the present invention can be chemically linked to a single biomolecule. An example of such a structure can be represented as: $[Z^1\text{-}(PMB)\text{-}Z^2]_u\text{-}BM$, wherein u=1-500 and $Z^1$, $Z^2$, PMB and BM are as defined above.

Salts of the disclosed compounds are also contemplated, and include both base and acid addition salts. The compounds of the present invention can have one or more sufficiently acidic proton that can react with a suitable organic or inorganic base to form a base addition salt. Base addition salts include those derived from inorganic bases, such as ammonium or alkali or alkaline earth metal hydroxides, carbonates, bicarbonates, and the like, and organic bases such as alkoxides, alkyl amides, alkyl and aryl amines, and the like. Such bases useful in preparing the salts of this invention thus include sodium hydroxide, potassium hydroxide, ammonium hydroxide, potassium carbonate, and the like.

The compounds of the present invention having a sufficiently basic group, such as an amine can react with an organic or inorganic acid to form an acid addition salt. Acids commonly employed to form acid addition salts from compounds with basic groups are inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromophenyl-sulfonic acid, carbonic acid, succinic acid, citric acid, benzoic acid, acetic acid, and the like. Examples of such salts include the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycolate, tartrate, methanesulfonate, propanesulfonate, naphthalene-1-sulfonate, naphthalene-2-sulfonate, mandelate, and the like.

For example, compounds of Formula I can be represented by formulae Ia, Ib and Ic

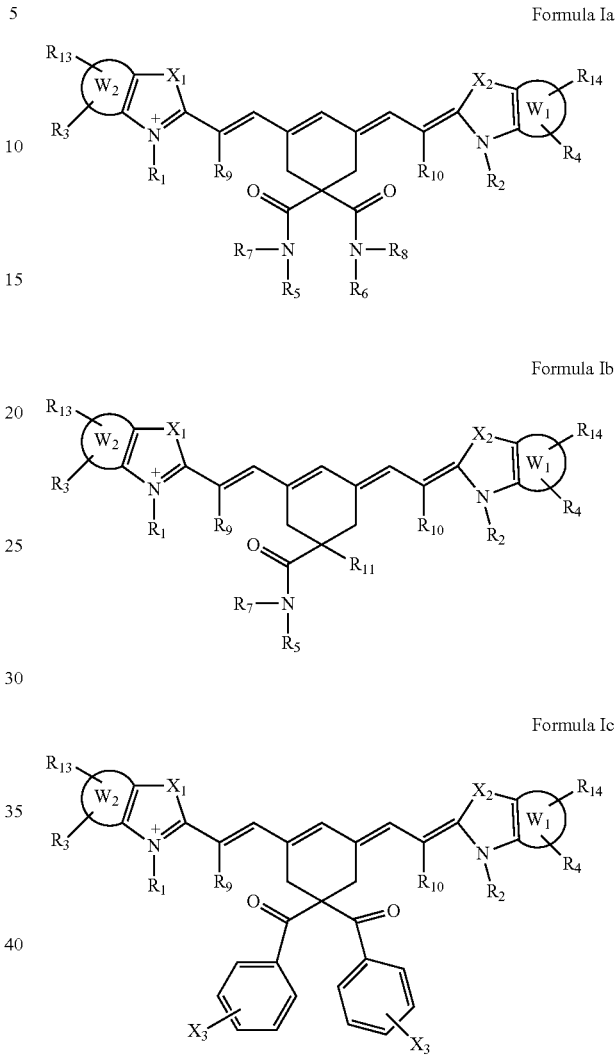

Formula Ia

Formula Ib

Formula Ic or a salt thereof, wherein:
Wherein $X_1$ and $X_2$ are independently chosen from O, S, Se, $C(CH_2R_3CH_2R_4)$; $R_1$, $R_2$, $R_5$, $R_6$, $R_7$ and $R_8$ are each independently chosen from: H, $(CH_2)_nX_3$, wherein n=1-20; $R_3$, $R_4$, $R_{13}$ and $R_{14}$ are each independently chosen from: H, $(CH_2)_nX_3$, wherein n=0-20; $X_3$ is independently chosen from: H, halogen, $CH_3$, $SO_3H$, $SO_3$—, COOH, NCS (isothiocyanate), NCO (iscocyanate), N-hydroxy succinimidyl (NHS) ester, N-hydroxysulfosuccinimidyl (NHSS) ester, hydroxy (OH), thiol (SH), maleimide, phthalimide, iodoacetamide, CN, $NH_2$, CONHR, alkyne, azide ($N_3$), $SO_2NX_3R_7$, aryl that is optionally further substituted with $X_3$; $R_9$ and $R_{10}$ are H or halogen or alkyl group; $R_1$ and $R_9$ or $R_2$ and $R_{10}$ optionally taken together form a 5 or 6 or 7 membered ring; $W_1$ and $W_2$ are the atoms necessary to form aryl rings including benzo or naphtho or pyridyl; $R_{11}$ is independently chosen from: COOH, CN, F, $NO_2$, $COCF_3$, $CF_3$, COOR, CONHR, $CO(CH_2)_nR$, wherein R is H or COOH or $SO_3H$, or $NH_2$ or SH or alkyl or aryl which is optionally further substituted with $X_3$, or polyethylene glycol (PEG) units

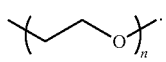

In certain embodiments, X₃ is selected from the group consisting of —NH₂, —OH, —SH, —SO₃H, carboxyl, —COCl, —(CO)O(CO)R₁₆, —CONHNH₂, substituted and unsubstituted N-hydroxysuccinimido esters, substituted and unsubstituted N-hydroxysulfosuccinimido esters, nitro- or fluoro-phenol esters, azide, —NCS, —CHO, azide, —COCH₂I, phosphoramidite, phthalamido, and maleimide, wherein $R_{16}$ is selected from the group consisting of H, alkyl and aryl.

In other embodiments, $X_1$ and $X_2$ are —C(CH₃)₂.

It is understood that $W_1$ and $W_2$ may be the same or different. For example, $W_1$ and $W_2$ can be selected from the group consisting of:

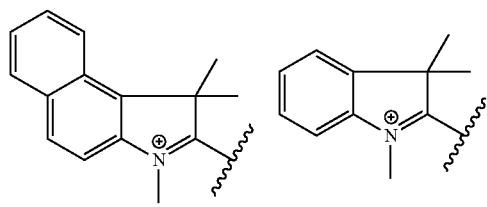

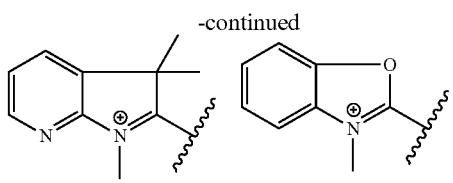

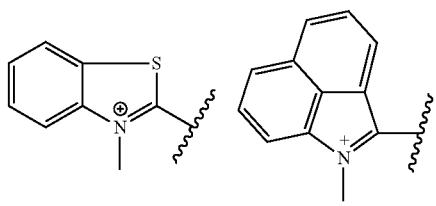

Incorporation of one or more non-hydrogen substituents on the fused rings can be used to tune the absorption and emission spectrum of the resulting dye.

In certain embodiments, the compounds is one of the following or a salt thereof:

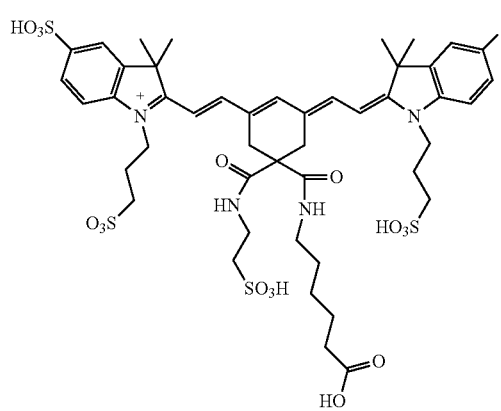

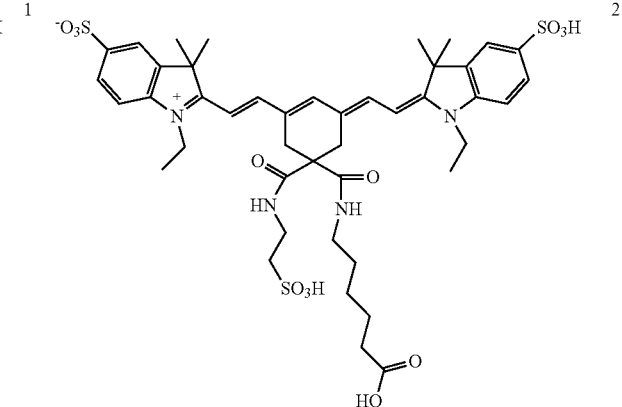

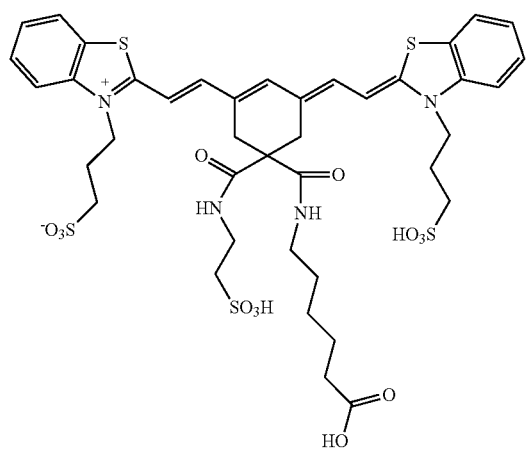

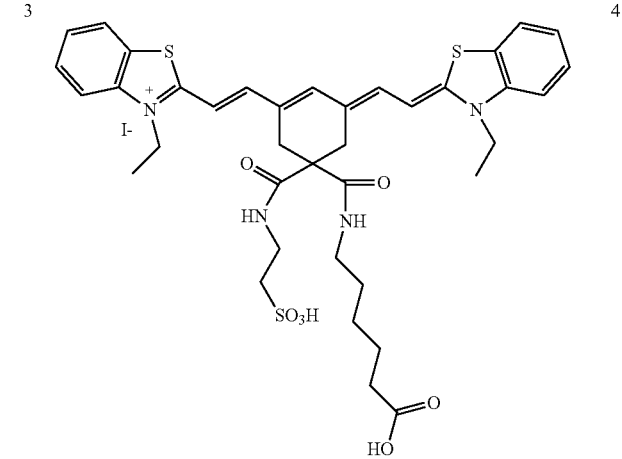

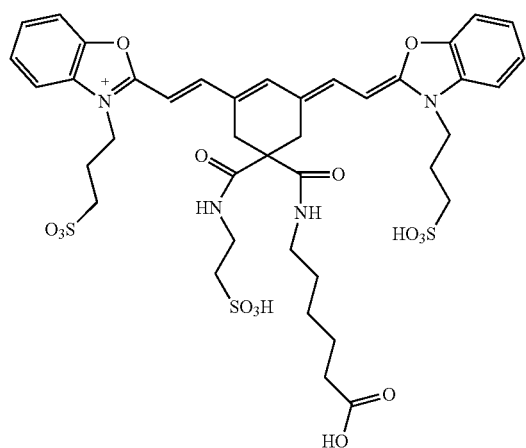
5
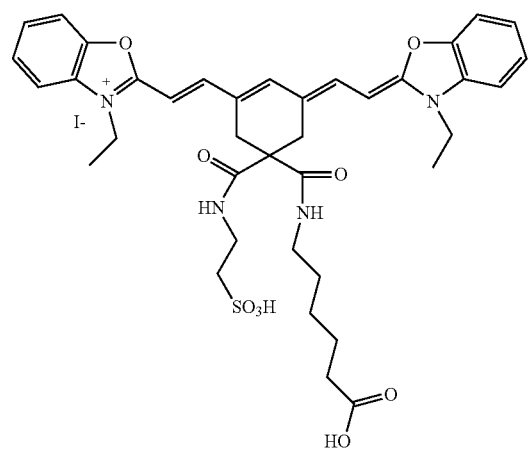
6
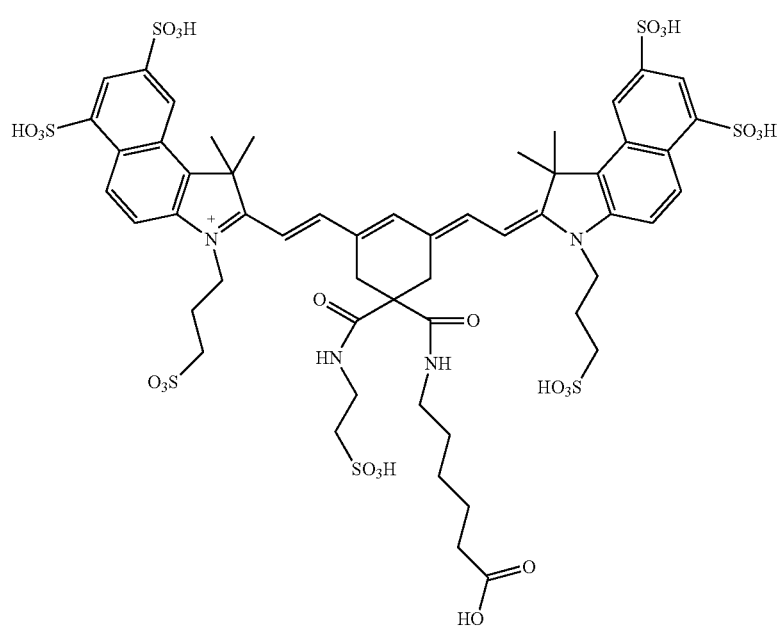
7

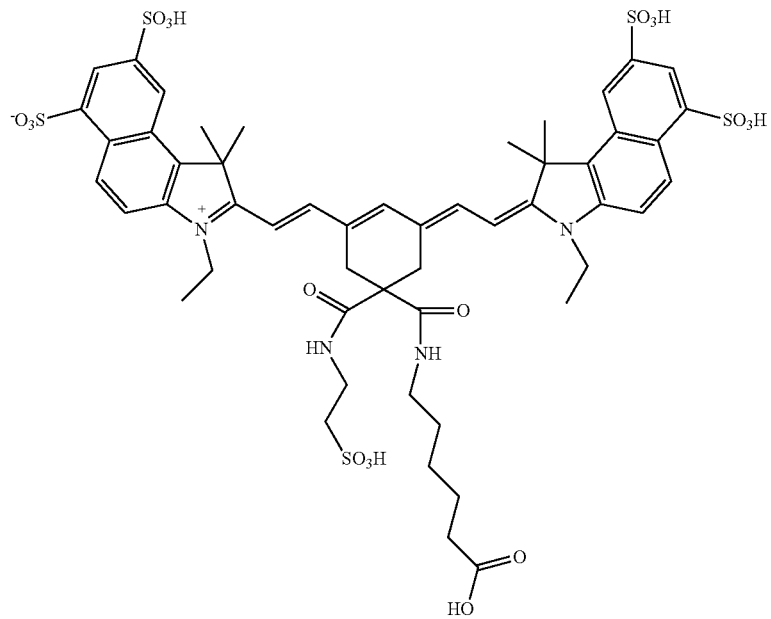
8
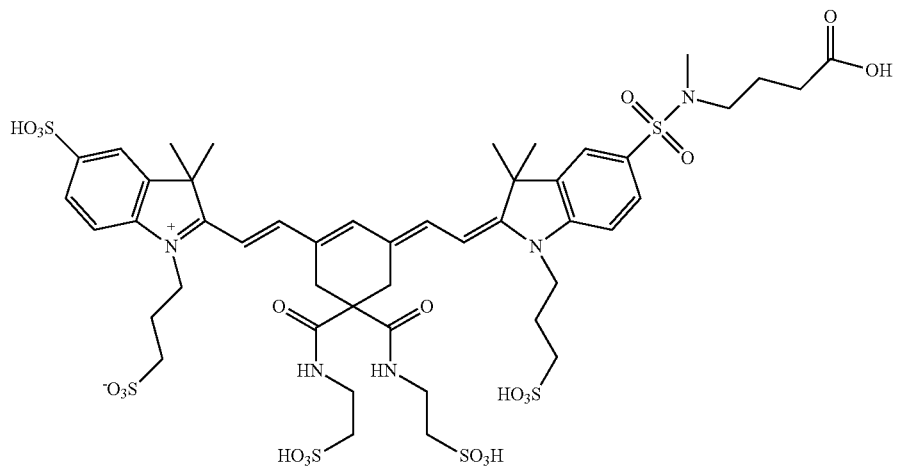
9
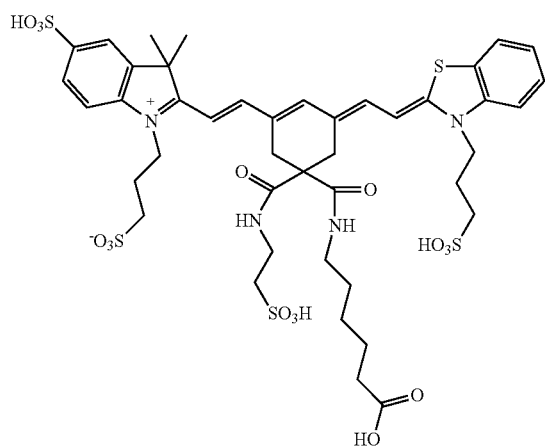
10
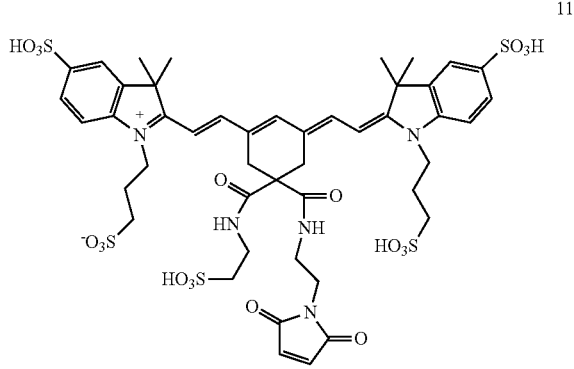
11

12
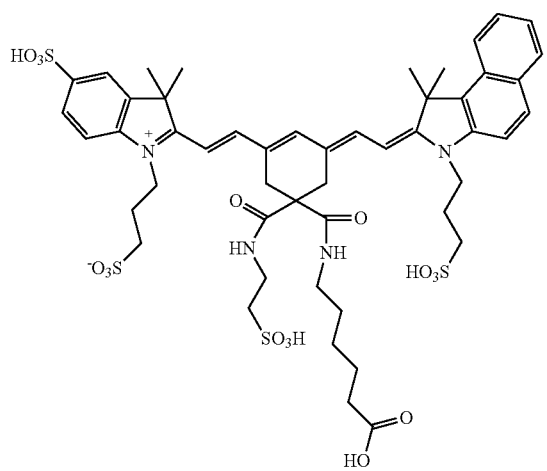
13
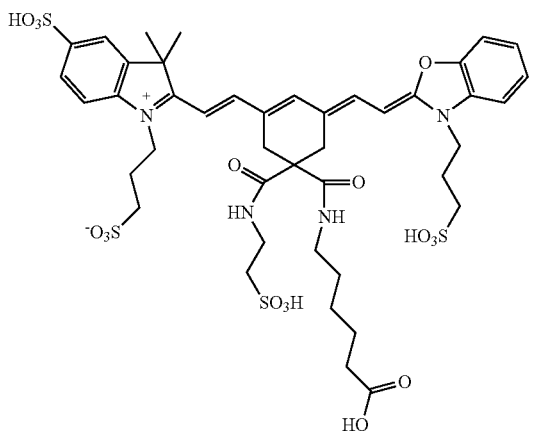
14
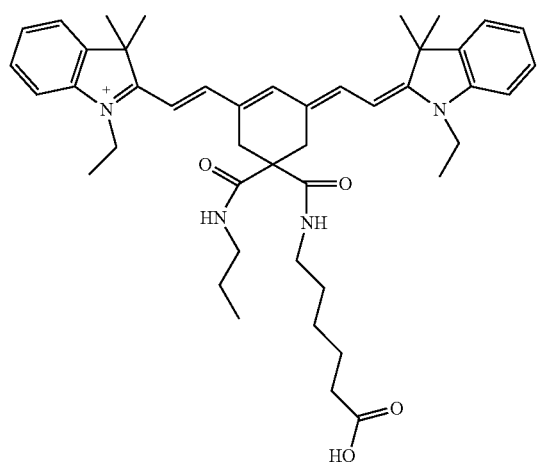
15
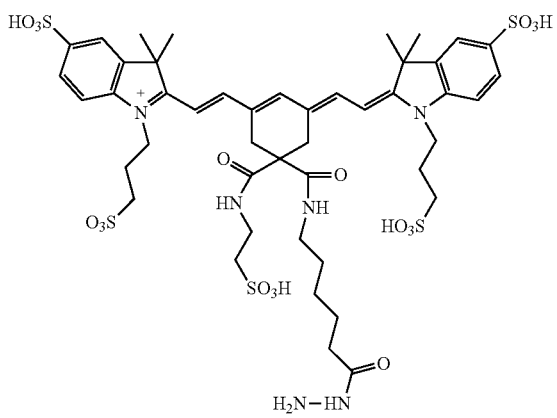
16
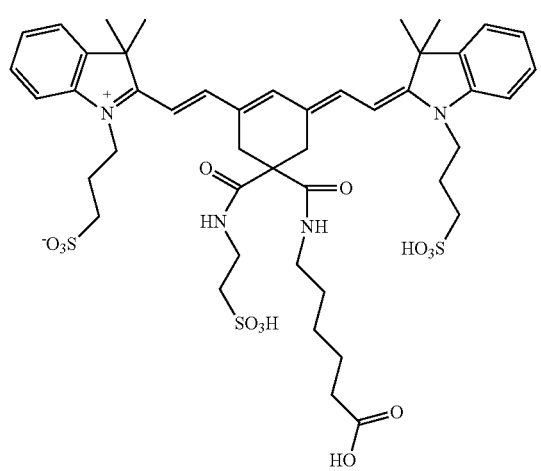
17
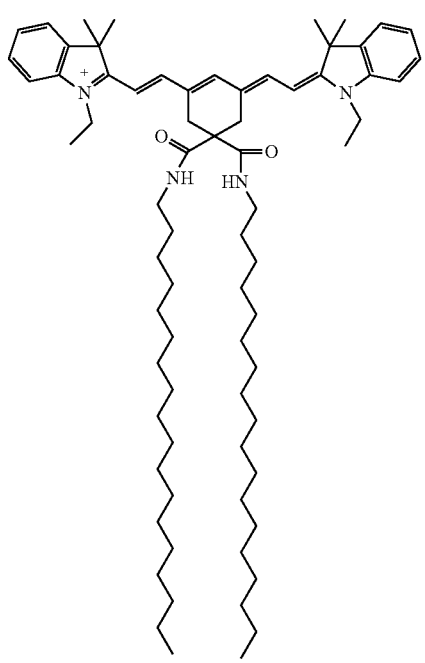

-continued
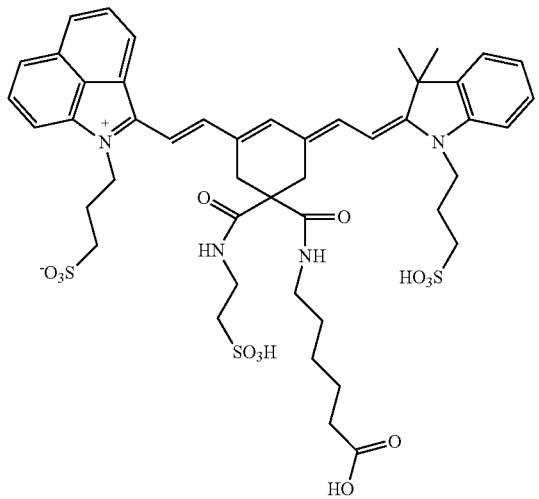
18
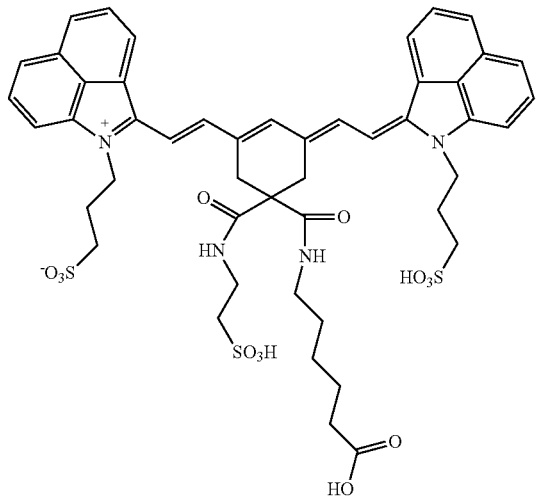
19
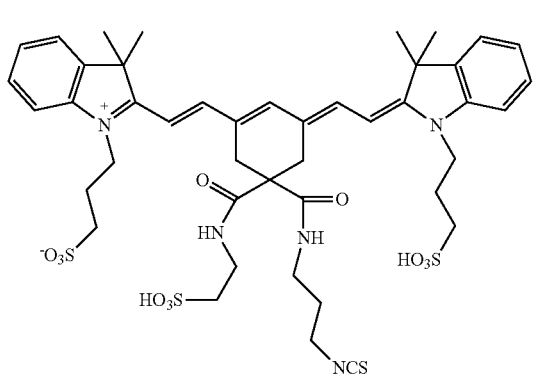
20
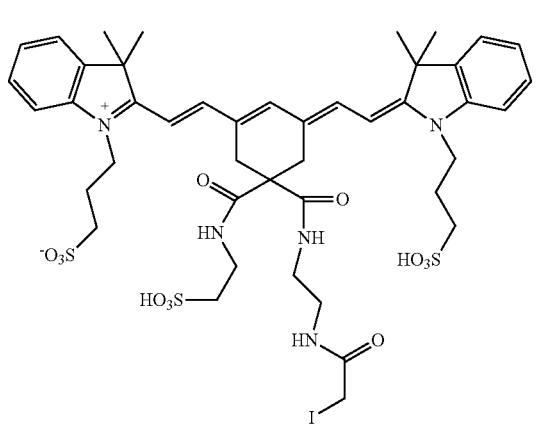
21
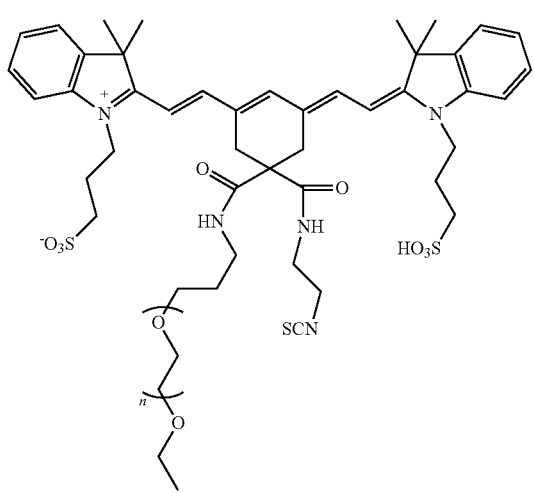
22
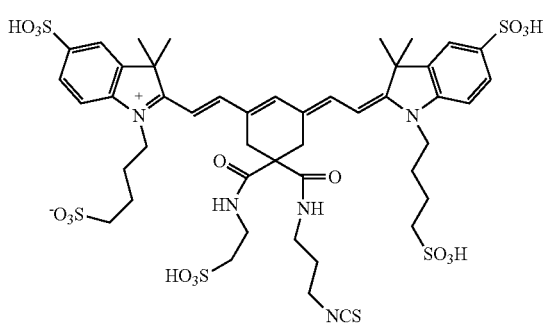
23

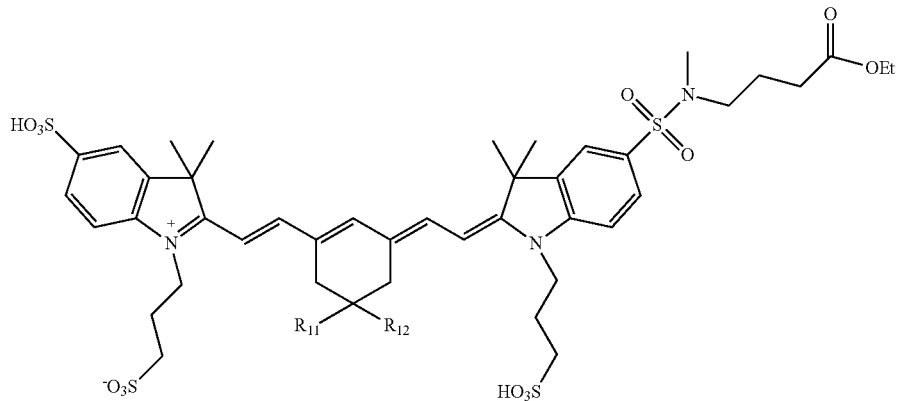
24
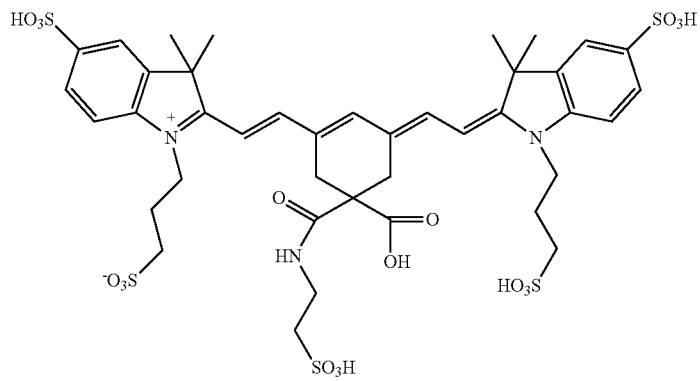
27
$R_{11}$ and $R_{12}$ are independently: COOH, CONHR, CN, O=C-Phenyl, COCH$_2$R where R=H or
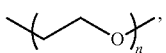
$(CH_2)_nCOOR'$ or $(CH_2)_nCH_3$ or $(CH_2)_nSO_3H$ or $(CH_2)_nSO_3^-$, where R'=alkyl or aryl
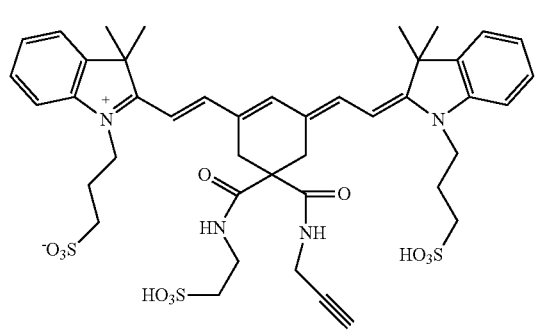
25
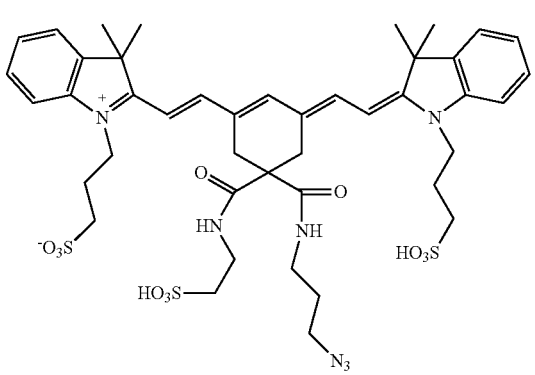
26

28
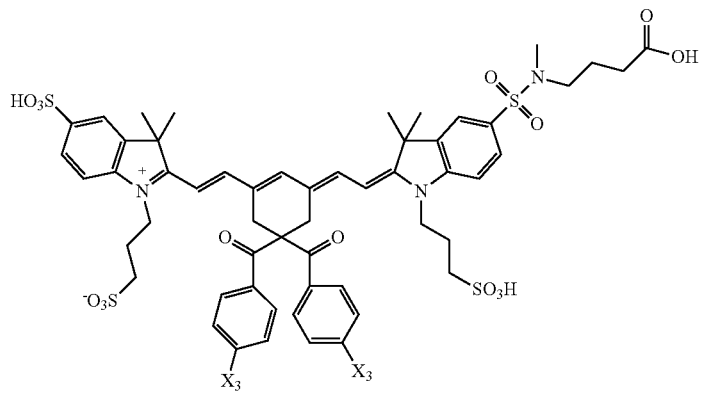
| X3 AND/OR X4 | | |
|---|---|---|
| 28A | H | 29A |
| 28B | Cl | 29B |
| 28C | Br | 29C |
| 28D | F | 29D |
| 28E | I | 29E |
| 28F | SO3H | 29F |
| 28G | COOH | 29G |
29
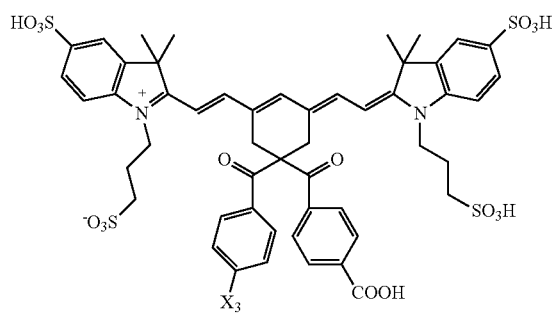
30
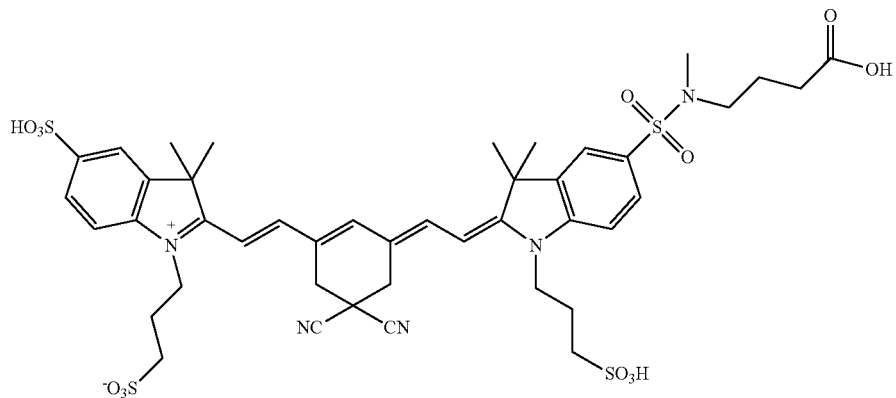
31
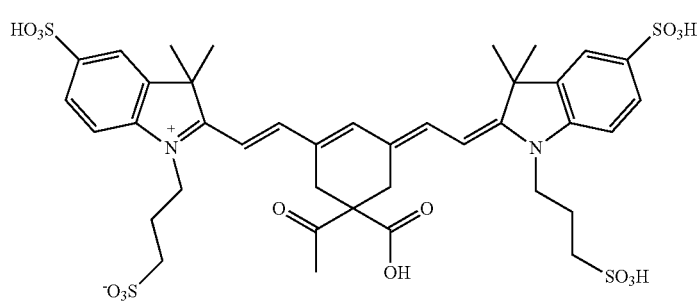

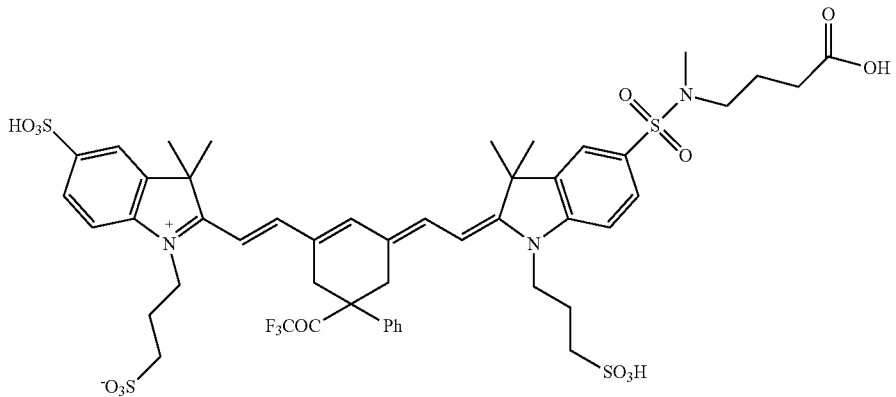
32
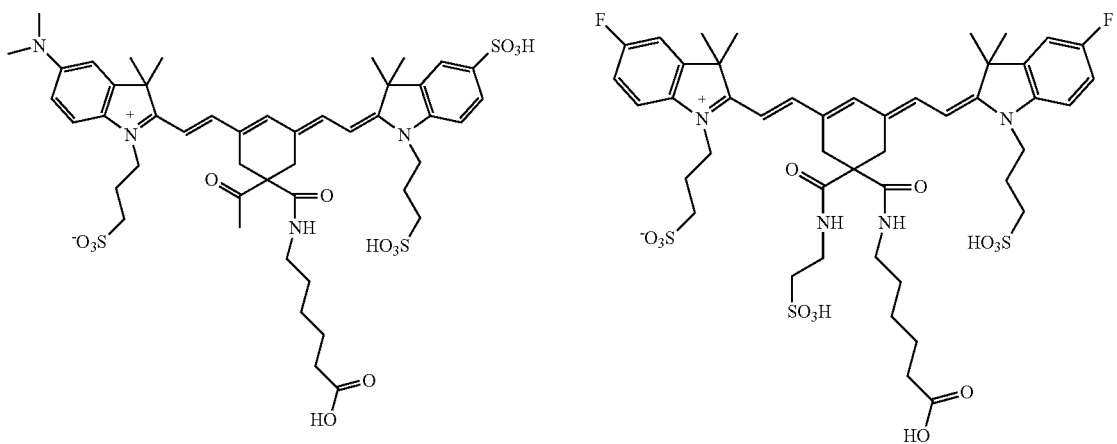
33
34
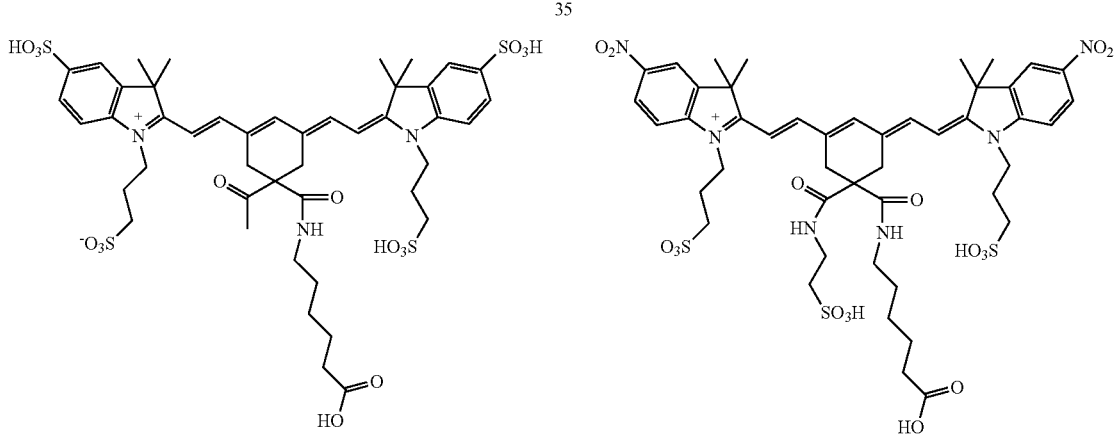
35
38

-continued
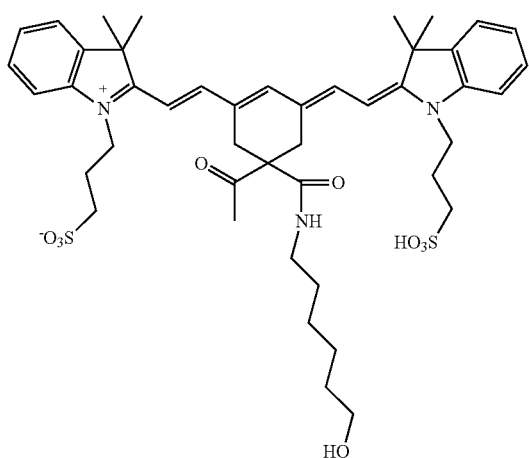
36
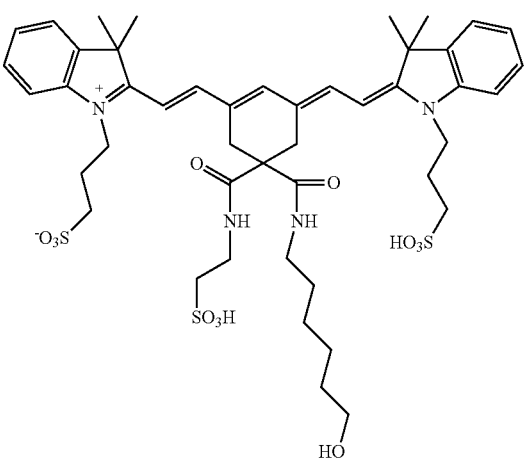
37
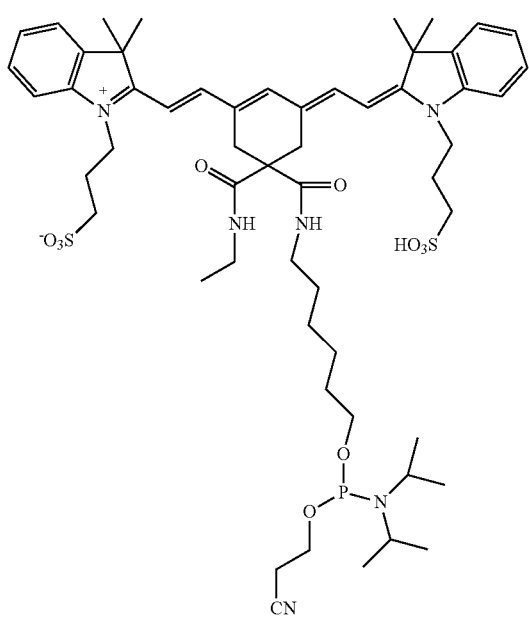
39
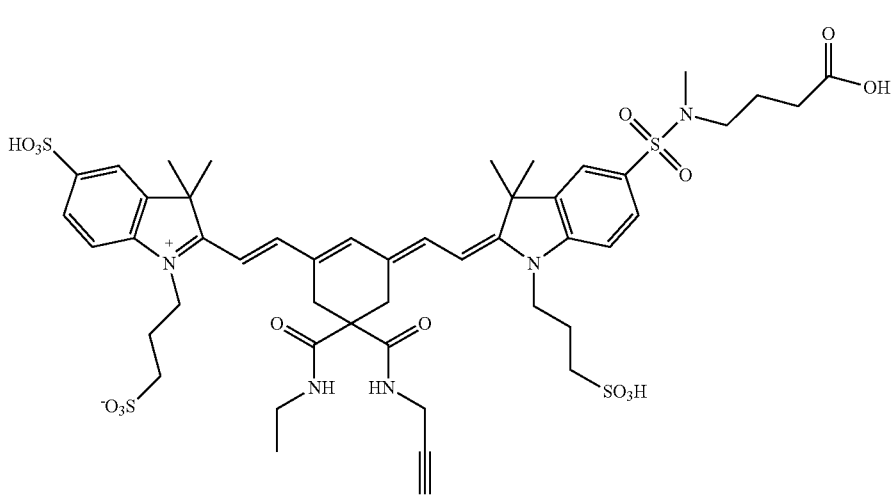
40

41
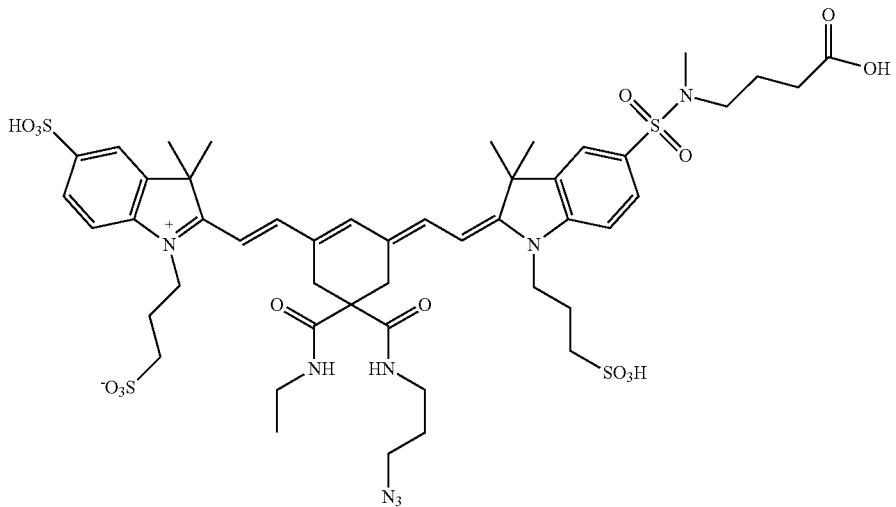
42
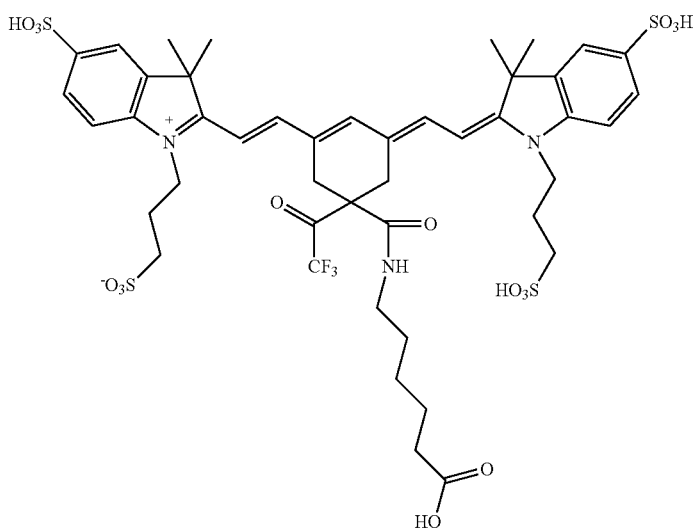
43
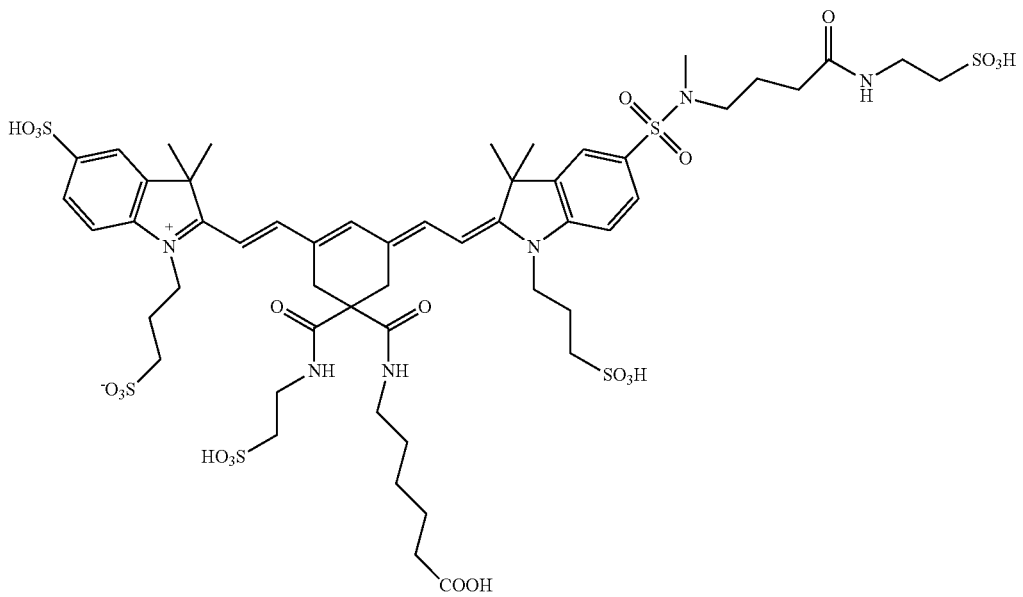

When a compound of the invention is depicted herein by structure indicating the positions of the double bonds in the rings and polymethine bridge, it is to be understood that the structure also encompasses any resonance structures as shown, for example, in the figure below:

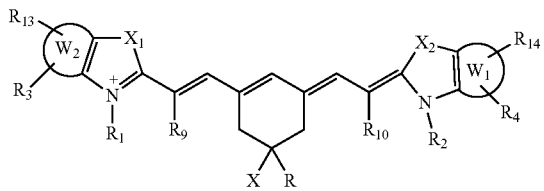

Formula I

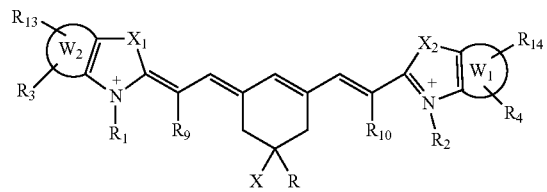

Formula I' wherein, in each of the foregoing structures, $R_1$, $R_2$, $R_3$, $R_4$, $R_5$, $R_6$, $R_7$, $R_8$, $R_9$, $R_{10}$, $R_{13}$, $R_{14}$, $W_1$, $W_2$, $X_1$, $X_2$, and $X_3$ are as defined herein.

Generally, the compounds disclosed herein can be synthesized as follows. First, a quaternized heterocycle, $Z^1$, is prepared. Then, the heterocyclic base is reacted with a polymethine bridge (PMB) that is an electrophilic reagent, such as PhNH-PMB-CH=NHPh.HCl, or RO-PMB—CH(OR)$_2$, where PMB consists of a conjugated double bond chain (CH=CH)$_n$— that includes a 4,4-disubstituted cyclohexyl bridged moiety as part of such chain, and where Ph is a phenyl ring and R a methyl or ethyl group, to obtain hemicyanines such as $Z^1$—PMB-CH=NHPh or $Z^1$—PMB-CH=NAcPh (where Ac is the acetyl radical) or $Z^1$—(CH=CH)$_n$—OR. These intermediates then are reacted with a different quaternary heterocycle, $Z^2$. The functionalized side arm is attached either to the first ($Z^1$) or to the second ($Z^2$) quaternized heterocycle. The final result is a non-symmetric polymethine labeling reagent, $Z^1$-PMB-$Z^2$. Examples of hemicyanine intermediates are described in F. M. Hamer, "Some Unsymmetrical Pentamethincyanine Dyes and their Tetramethin Intermediates", J. Chem. Soc., 32 (1949) and R. B. Mujumdar, L. A. Ernst, Swati R. Mujumdar, C. J. Lewis, and A. S. Waggoner, "Cyanine Dye Labelling Reagents: Sulfoindocyanine Succinimidyl Esters", Bioconjugate Chemistry, 4, 105, (1993).

In another aspect, the invention provides compounds of general structural formula V

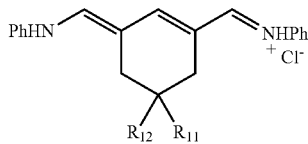

Formula V wherein $R_{11}$ and $R_{12}$ are independently: COOH, CONHR, CF$_3$, halogen, CN, O=C-Phenyl, COCH$_2$R where R=H or

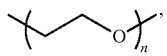

(CH$_2$)$_n$COOR' or (CH$_2$)nCH$_3$ or (CH$_2$)$_n$SO$_3$H or (CH$_2$)$_n$SO$_3^-$, where R'=alkyl or aryl; Ph is phenyl group, which is optionally substituted with one of: F, Cl, Br, I, OMe, NMe$_2$, NO$_2$, CN, CF$_3$, alkyl.

The certain other embodiments, following structure represented by formula 45a and 45b are contemplated, wherein R' is alkyl or aryl

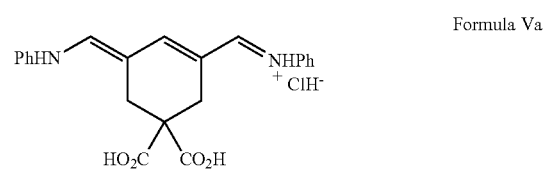

Formula Va

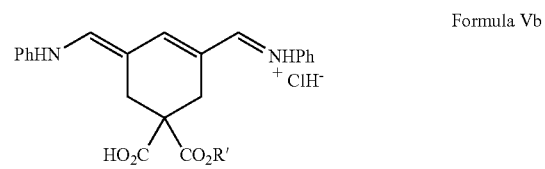

Formula Vb

In certain embodiments, the compounds of the invention can be chemically linked to a biological molecule or biomolecule (BM) as represented by formula III—[BM]$_n$-F$_m$, wherein BM is a biomolecule, F is a fluorophore represented by formulae 1a, 1b or 1c (as described above), and n=1 to 4; m=1 to 100. The resulting compound-biomolecule conjugate can have a high binding affinity to a target, for example, due to an interaction between the biological molecule and the target, for example, via a receptor-ligand interaction, enzyme-substrate interaction, an antibody-antigen interaction, or the like. In other embodiments, such chemically linked compounds, of the general form [Z$^1$-(PMB)-Z$^2$]-BM, can be represented, for example, as:

Biomolecule attached fluorophores

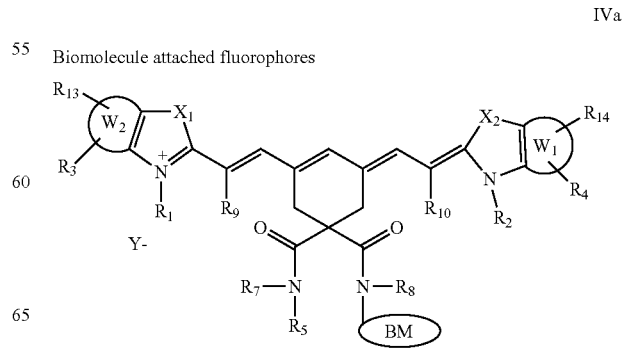

IVa

-continued

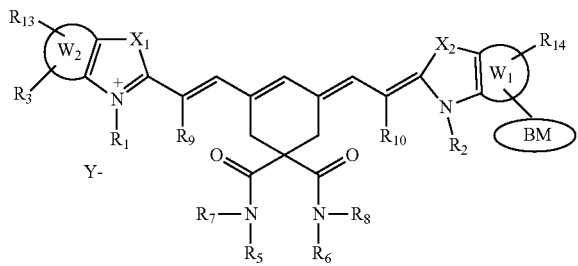

IVb

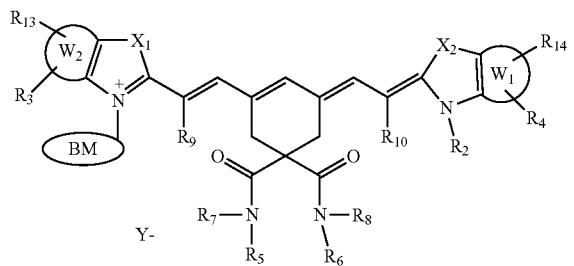

IVc

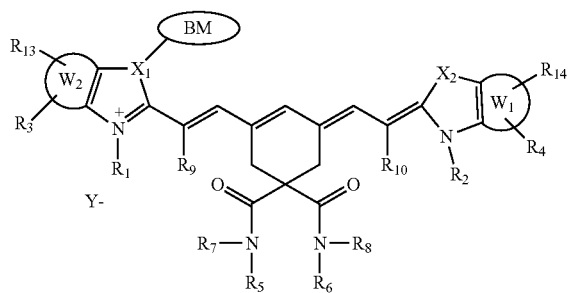

IVd wherein, in each of the foregoing structures, $R_1$, $R_2$, $R_3$, $R_4$, $R_5$, $R_6$, $R_7$, $R_8$, $R_9$, $R_{10}$, $R_{13}$, $R_{14}$, $W_1$, $W_2$, $X_1$, $X_2$, and $X_3$ are as defined herein, $Y^-$ is a counterion, and BM is a biomolecule. The foregoing structures are exemplary and it is understood that a biomolecule (BM) can be chemically linked to such compound via any one or more of the groups identified as $R_1$, $R_2$, $R_3$, $R_4$, $R_5$, $R_6$, $R_7$, $R_8$, $R_9$, $R_{10}$, $R_{13}$, $R_{14}$, $W_1$, $W_2$, $X_1$, $X_2$, and $X_3$ Another aspect of the invention provides a conjugate compound formed by reaction of a biological molecule with a compound a compound described herein, such as a compound of Formula I-A, I—B, I—C, I-D, or II.

Another aspect of the invention provides a conjugate compound that is a compound described herein (such as a compound of Formula I-A, I-B, I-C, I-D, or II) further substituted with 1, 2, or 3 groups defined by -L-BM; wherein L is a bond or a linker, and -BM is a radical of a biological molecule.

The compounds can be labeled with a biomolecules or cells as follows. The compounds (fluorochromes) of the present invention are incubated with one or more biomolecules at various concentrations for about 5 minutes to 24 hours or more at a temperature from about 4° C. to about 37° C. After the incubation, the free fluorochrome or the fluorochrome that has not been chemically linked to the biomolecule can be removed using methods known to those skilled in art, such as for example, chromatography or ultrafiltration methods.

Cells can be centrifuged after incubation to create a cell pellet from which the supernatant is removed. Cells can be re-suspended in culture media or physiologic saline to wash away residual, unbound or free fluorochrome. This can be repeated several times. In this manner, cells can be labeled either by direct conjugation to internal or external cellular molecules or by non-specific cell uptake into various intracellular compartments, including but not limited to cytosol, endosomes, nucleus, golgi apparatus, and other intracellular organelles.

The disclosed compounds and/or compositions can be packaged as a kit, which may optionally include instructions for using the compounds. Non-limiting examples include kits that contain, for example, a composition in a powder or lyophilized form, and instructions for using, including reconstituting, dosage information, and storage information for in vivo and/or in vitro applications. Kits may optionally contain containers of a composition in a liquid form ready for use, or requiring further mixing with solutions for administration, such as vials for reconstituting powder forms, syringes for injection, customized IV delivery systems, inhalers, etc. Such containers may contain single or multiple subject doses. Additionally, a kit can contain components that aid in the detection of the compositions in vivo or in vitro, for example, specialized endoscopes, light filters.

Compounds disclosed herein, including those compounds chemically linked to a biomolecule, can be formulated in a pharmaceutical composition suitable for administration to a subject, for example, an animal or human subject. Accordingly, the formulations include the compounds together with a physiologically acceptable carrier suitable for the desired form and/or dose of administration. Physiologically acceptable carriers can include water, saline, and may further include agents such as buffers, and other agents such as preservatives that are compatible for use in pharmaceutical formulations. The preferred carrier is a fluid, preferably a liquid, more preferably an aqueous solution; however, carriers for solid formulations, topical formulations, inhaled formulations, ophthalmic formulations, and transdermal formulations are also contemplated as within the scope of the invention.

In addition, the pharmaceutical compositions can include one or more stabilizers in a physiologically acceptable carrier. Suitable example of stabilizers for use in such compositions include, for example, low molecular weight carbohydrates, for example a linear polyalcohol, such as sorbitol, and glycerol. Other low molecular weight carbohydrates, such as inositol, may also be used.

It is contemplated that the compounds of the invention can be administered orally or parenterally. For parenteral administration, the compounds can be administered intravenously, intramuscularly, cutaneously, percutaneously, subcutaneously, rectally, nasally, vaginally, and ocularly. Thus, the composition may be in the form of, e.g., solid tablets, capsules, pills, powders including lyophilized powders, colloidal suspensions, microspheres, liposomes granulates, suspensions, emulsions, solutions, gels, including hydrogels, pastes, ointments, creams, plasters, irrigation solutions, drenches, osmotic delivery devices, suppositories, enemas, injectables, implants, sprays, or aerosols. The pharmaceutical compositions can be formulated according to conventional pharmaceutical practice (see, for example, Remington: The Science and Practice of Pharmacy, 20th edition, 2000, ed. A. R. Germaro, Lippincott Williams & Wilkins, Philadelphia, and Encyclopedia of Pharmaceutical Technology, eds. J. Swarbrick and J. C. Boylan, 1988-1999, Marcel Dekker, New York).

III Applications of the Fluorochrome Compounds of the Invention

The compounds of the invention can be used in a variety of in vivo and in vitro applications. These applications are discussed in the following sections.

(a) In Vivo Applications

The invention provides novel fluorescent compounds that can be used in a variety of imaging applications, for example, optical imaging applications. For a review of optical imaging techniques, see, e.g., Alfano et al., *Ann. NY Acad. Sci.* 820:248-270, 1997; Weissleder, Nature Biotechnology 19, 316-317 (2001); Ntziachristos et al., Eur. Radiol. 13:195-208 (2003); Graves et al., Curr. Mol. Med. 4:419-430 (2004); Citrin et al., Expert Rev. Anticancer Ther. 4:857-864 (2004); Ntziachristos, Ann. Rev. Biomed. Eng. 8:1-33 (2006); Koo et al., Cell Oncol. 28:127-139 (2006); and Rao et al., Curr. Opin. Biotechnol. 18:17-25 (2007).

An imaging system useful in the practice of this invention typically includes three basic components: (1) an appropriate light source for exciting the fluorochrome compounds of the invention, (2) a system for separating or distinguishing emissions from light used for inducing fluorochrome excitation, and (3) a detection system. This detection system can be hand-held or incorporated into other useful imaging devices such as endoscopes, catheters, intraoperative microscopes and/or viewers.

Preferably, the light source provides monochromatic (or substantially monochromatic) light. The light source can be a suitably filtered white light, i.e., bandpass light from a broadband source. For example, light from a 150-watt halogen lamp can be passed through a suitable bandpass filter commercially available from Omega Optical (Brattleboro, Vt.). Depending upon the system, the light source can be a laser. See, e.g., Boas et al., *Proc. Natl. Acad. Sci.* USA 91:4887-4891, 1994; Ntziachristos et al., *Proc. Natl. Acad. Sci.* USA 97:2767-2772, 2000; and Alexander, *J. Clin. Laser Med. Surg.* 9:416-418, 1991. Information on lasers for imaging can be found, for example, at Imaging Diagnostic Systems, Inc., Plantation, Fla. and various other sources. A high pass or bandpass filter can be used to separate optical emissions from excitation light. A suitable high pass or bandpass filter is commercially available from Omega Optical, Burlington, Vt.

In general, the light detection system can be viewed as including a light gathering/image forming component and a light detection/image recording component. Although the light detection system can be a single integrated device that incorporates both components, the light gathering/image forming component and light detection/image recording component are discussed separately.

A particularly useful light gathering/image forming component is an endoscope. Endoscopic devices and techniques which have been used for in vivo optical imaging of numerous tissues and organs, including peritoneum (Gahlen et al., *J. Photochem. Photobiol.* B 52:131-135, 1999), ovarian cancer (Major et al., *Gynecol. Oncol.* 66:122-132, 1997), colon and rectum (Mycek et al., *Gastrointest. Endosc.* 48:390-394, 1998; and Stepp et al., *Endoscopy* 30:379-386, 1998), bile ducts (Izuishi et al., *Hepatogastroenterology* 46:804-807, 1999), stomach (Abe et al., *Endoscopy* 32:281-286, 2000), bladder (Kriegmair et al., *Urol. Int.* 63:27-31, 1999; and Riedl et al., *J. Endourol.* 13:755-759, 1999), lung (Hirsch et al., *Clin Cancer Res* 7:5-220, 2001), brain (Ward, *J. Laser Appl.* 10:224-228, 1998), esophagus, and head and neck regions can be employed in the practice of the present invention.

Other types of light gathering components are catheter-based devices, including fiber optics devices. Such devices are particularly suitable for intravascular imaging. See, for example, Tearney et al., *Science* 276: 2037-2039, 1997; and *Circulation* 94: 3013, 1996.

Still other imaging technologies, including phased array technology (Boas et al., *Proc. Natl. Acad. Sci.* USA 91:4887-4891, 1994; Chance, *Ann. NY Acad. Sci.* 838:29-45, 1998), optical tomography (Cheng et al., *Optics Express* 3:118-123, 1998; and Siegel et al., *Optics Express* 4:287-298, 1999), intravital microscopy (Dellian et al., *Br. J. Cancer* 82:1513-1518, 2000; Monsky et al, *Cancer Res.* 59:4129-4135, 1999; and Fukumura et al., *Cell* 94:715-725, 1998), confocal imaging (Korlach et al., *Proc. Natl. Acad. Sci.* USA 96:8461-8466, 1999; Rajadhyaksha et al., *J. Invest. Dermatol.* 104: 946-952, 1995; and Gonzalez et al., *J. Med.* 30:337-356, 1999) and fluorescence molecular tomography (FMT) (Nziachristos et al., *Nature Medicine* 8:757-760, 2002; U.S. Pat. No. 6,615,063, PCT Application No. WO 03/102558, and PCT US/03/07579) can be used with the fluorochrome compounds of the invention. Similarly, the fluorochrome compounds can be used in a variety of imaging systems, for example, [1] the IVIS® Imaging Systems: 100 Series, 200 Series (Xenogen, Alameda, Calif.), [2] SPECTRUM and LUMINA (Xenogen, Alameda, Calif.), [3] the SoftScan® or the eXplore Optix™ (GE Healthcare, United Kingdom), [4] Maestro™ and Nuance™-2 Systems (CRi, Woburn, Mass.), [5] Image Station In-Vivo FX from Carestream Molecular Imaging, Rochester, N.Y. (formerly Kodak Molecular Imaging Systems), [6] OV100, IV100 (Olympus Corporation, Japan), [7] Cellvizio Mauna Kea Technologies, France) [8] NanoSPECT/CT or HiSPECT (Bioscan, Washington, D.C.), [9] CTLM® or LILA™ (Imaging Diagnostic Systems, Plantation, Fla.), [10] DYNOT™ (NIRx Medical Technologies, Glen Head, N.Y.) and [11] NightOWL Imaging Systems by Berthold Technologies, Germany.

A variety of light detection/image recording components, e.g., charge coupled device (CCD) systems or photographic film, can be used in such systems. The choice of light detection/image recording depends on factors including the type of light gathering/image forming component being used. It is understood, however, that the selection of suitable components, assembling them into an optical imaging system, and operating the system is within ordinary skill in the art.

Optical imaging and measurement techniques include, but are not limited to, fluorescence imaging, luminescence imaging; endoscopy; fluorescence endoscopy; optical coherence tomography; transmittance imaging; time resolved transmittance imaging; confocal imaging; nonlinear microscopy; photoacoustic imaging; acousto-optical imaging; spectroscopy; reflectance spectroscopy; intravital imaging; two photon imaging; interferometry; coherence interferometry; diffuse optical tomography and fluorescence molecular tomography.

It is contemplated that the fluorochrome compounds of the injection can be coupled to or incorporated within a solid support, for example, a particle. Accordingly, it is understood that the fluorochrome compounds can be coupled to metal oxide nanoparticles that have magnetic properties to produce particles that are also fluorescent. Accordingly, the resulting particles can also be used in MRI imaging using techniques known in the art. For a review of MRI techniques see Westbrook, Handbook of MRI Technique, $2^{nd}$ Edition, 1999, Blackwell Science. It is possible that images obtained, for example, by fluorescent molecular tomography and by magnetic resonance imaging can be co-registered or fused with one another to provide additional information about the item being imaged. Furthermore, multi-modality imaging systems (i.e., combined optical and MR imaging systems) can be used to create combined optical MR images.

In addition, the compositions and methods of the present invention can be used in combination with other imaging compositions and methods. For example, the fluorochrome compounds of the invention can be used to image regions of interest via optical imaging protocols either alone or in combination with other traditional imaging modalities, such as, X-ray, computed tomography (CT), MR imaging, ultrasound, positron emission tomography (PET), and single photon computerized tomography (SPECT). For instance, the compositions and methods of the present invention can be used in combination with CT or MR imaging to obtain both anatomical and molecular information simultaneously, for example, by co-registration of an image generated by another imaging modality. The compositions and methods of the present invention can also be used in combination with X-ray, CT, PET, ultrasound, SPECT, MR and other optical contrast agents or alternatively, the fluorochrome compounds of the present invention may also contain imaging agents, such as iodine, gadolinium atoms and radioactive isotopes, which can be detected using CT, PET, SPECT, and MR imaging modalities in combination with optical imaging.

An exemplary method of in vivo optical imaging comprises the steps of (a) administering to a subject, for example, a human or an animal, a fluorescent compound of the present invention; (b) allowing sufficient time for the fluorochrome compound to distribute within the subject or to contact or interact with a biological target; (c) exposing the subject to electromagnetic radiation, for example, light of a wavelength absorbable by the fluorochrome compound; and (d) detecting an optical signal emitted by the fluorochrome compound.

It is understood that the subject may be a vertebrate animal, for example, a mammal, including a human. The animal may also be non-vertebrate, (e.g., *C. elegans, drosophila*, or other model research organisms, etc.). The biological target can include, without limitation, cells, cell culture, tissues, tissue sections, organs, organ sections, cytospin samples, proteins, nucleic acids, carbohydrates, lipids, or the like.

The foregoing steps, including, for example, steps (a)-(d), can be repeated at predetermined time intervals thereby to permit evaluation of the emitted signals of the fluorochrome compounds in the subject over time. The illuminating and detecting steps (steps (c) and (d), respectively) can be performed using a planar imaging system, endoscope, catheter, tomographic system, hand-held optical imaging system, goggles, or an intraoperative microscope. The signal emitted by the fluorochrome compound can be used to construct an image, for example, a tomographic image.

Before or during these steps, a detection system can be positioned around or in the vicinity of a subject (for example, an animal or a human) to detect optical and/or other signals (e.g., MR, nuclear, X-ray) emitted from the subject. The emitted optical and/or other signals can be processed to construct an image, for example, a tomographic or planar image. In addition, the processed signals can be displayed as images either alone or as fused (combined) images.

In addition, it is possible to practice an in vivo imaging method that selectively detects and images one or more imaging agents simultaneously. In such an approach, for example, in step (a) noted above, two or more imaging agents whose signal properties are distinguishable from one another are administered to the subject, either at the same time or sequentially, wherein at least one of the imaging agents contains a fluorochrome compound of the invention. The use of multiple agents permits the recording of multiple biological processes, functions or targets.

The invention also features an in vivo imaging method where labeled cells are administered to the subject. The cells can be labeled with the fluorochrome compound ex vivo. The cells can be derived directly from a subject or from another source (e.g., from another subject, cell culture, etc.). The fluorochrome compound can be mixed with the cells to effectively label the cells and the resulting labeled cells administered into a subject in step (a). Steps (b)-(d) then are followed as described above. This method can be used for monitoring trafficking and localization of certain cell types, including T-cells, tumor cells, immune cells and stem cells, and other cell types. In particular, this method may be used to monitor cell-based therapies.

It is understood that the formulation of the fluorochrome compounds, the choice of mode of administration, the dosages of fluorochrome compounds administered to the subject, and the timing between administration of the fluorochrome compounds and their exposure of to light (and also other forms of electromagnetic radiation if appropriate under the circumstances) is within the level of skill in the art.

The methods of the invention can be used to determine a number of indicia, including tracking the localization of the fluorochrome compounds in the subject over time or assessing changes or alterations in the metabolism and/or excretion of the fluorochrome compounds in the subject over time. The methods can also be used to follow therapy for such diseases by imaging molecular events and biological pathways modulated by such therapy, including but not limited to determining efficacy, optimal timing, optimal dosing levels (including for individual patients or test subjects), and synergistic effects of combinations of therapy.

The methods and compositions of the invention can also be used to help a physician or surgeon to identify and characterize areas of disease, such as arthritis, cancers and specifically colon polyps, or vulnerable or unstable plaque, to distinguish diseased and normal tissue, such as detecting tumor margins that are difficult to detect using an ordinary operating microscope, e.g., in brain surgery, to help dictate a therapeutic or surgical intervention, for example, by determining whether a lesion is cancerous and should be removed or non-cancerous and left alone, or in surgically staging a disease, e.g., intraoperative lymph node staging, sentinel lymph node mapping, or assessing intraoperative bleeding or to delineate tumor margins.

The methods and compositions of the invention can also be used in the detection, characterization and/or determination of the localization of a disease, especially early disease, the severity of a disease or a disease-associated condition, the staging of a disease, and/or monitoring a disease. The presence, absence, or level of an emitted signal can be indicative of a disease state. The methods and compositions of the invention can also be used to monitor and/or guide various therapeutic interventions, such as surgical procedures, and monitoring drug therapy, including cell based therapies. The methods of the invention can also be used in prognosis of a disease or disease condition.

With respect to each of the foregoing, examples of such disease or disease conditions that can be detected or monitored (before, during or after therapy) include, for example, inflammation (e.g., inflammation caused by arthritis, for example, rheumatoid arthritis), cancer (e.g., colorectal, ovarian, lung, breast, prostate, cervical, testicular, skin, brain, gastrointestinal, pancreatic, liver, kidney, bladder, stomach, leukemia, mouth, esophageal, bone), cardiovascular disease (e.g., atherosclerosis and inflammatory conditions of blood vessels, ischemia, stroke, thrombosis, disseminated intravascular coagulation), dermatologic disease (e.g., Kaposi's Sarcoma, psoriasis, allergic dermatitis), ophthalmic disease (e.g., macular degeneration, diabetic retinopathy), infectious disease (e.g., bacterial, viral, fungal and parasitic infections, including Acquired Immunodeficiency Syndrome, malaria, Chagas disease, schistosomiasis), immunologic disease (e.g., an autoimmune disorder, lymphoma, multiple sclerosis, rheumatoid arthritis, diabetes mellitus, lupus erythematosis, myasthenia gravis, Graves disease), central nervous system disease (e.g., a neurodegenerative disease, such as Parkinson's disease, Alzheimer's disease, Huntington's disease, amyotrophic lateral sclerosis, prion disease), inherited diseases, metabolic diseases, environmental diseases (e.g., lead, mercury and radioactive poisoning, skin cancer), bone-related disease (e.g., osteoporosis, primary and metastatic bone tumors, osteoarthritis), neurodegenerative disease, and surgery-related complications (such as graft rejection, organ rejection, alterations in wound healing, fibrosis, or other complications related to surgical implants).

The methods and compositions of the invention, therefore, can be used, for example, to determine the presence and/or localization of tumor cells, the presence and/or localization of inflammation, including the presence of activated macrophages, for instance in atherosclerosis or arthritis, the presence and in localization of vascular disease including areas at risk for acute occlusion (i.e., vulnerable plaques) in coronary and peripheral arteries, regions of expanding aneurysms, unstable plaque in carotid arteries, and ischemic areas. The disclosed methods of the invention can be used, for example, in identification and evaluation of apoptosis, necrosis, hypoxia and angiogenesis. Alternatively, the disclosed methods may also be used to assess the effect of a therapeutic compound or therapy on a specified molecular target by, for example, imaging a subject prior to and after treatment with the therapeutic compound or therapy, and comparing corresponding images.

(b) In Vitro Applications

In addition, it is appreciated that the fluorochrome compounds can also be used in a variety of in vitro assays, for example, binding experiments, and in vitro imaging experiments. It is understood that the imaging technologies discussed in the previous section are also applicable to in vitro imaging experiments.

An exemplary in vitro imaging method comprises: (a) contacting a sample with a probe comprising a fluorochrome compound of the invention; (b) allowing the fluorochrome compound to (i) become activated by and/or (ii) bind to a biological target; (c) optionally removing unactivated or unbound fluorochrome compound; (d) exposing the sample to electromagnetic radiation, for example, light, of a wavelength absorbable by the fluorochrome compound; and (e) detecting signal emitted from the fluorochrome compounds thereby to determine whether the probes have been activated or bound by the biological target.

The sample can be a liquid or solid sample containing, for example, primary cells, cell cultures, or tissue. The biological target can be, for example, a cell, an aggregation of cells, a tissue or tissue sample, a structure (both on the macrocellular level (for example, bone or tissue) or on a subcellular level (for example, a mitochondria or nucleus)), and a cellular component, for example, a protein (for example, an enzyme or structural protein), lipid, nucleic acid or polysaccharide.

The fluorochrome compounds can be used in a variety of in vitro ligand binding assays such, when incorporated into magnetic particles, can be used in magnetic detection based assays (see, U.S. Pat. Nos. 6,046,585 and 6,275,031, 5,445, 970; 4,219,335, Chemla, et. al. (2000) *Proc Natl Acad. Sci USA* 97, 14268-72). They can also be used in magnetic resonance based ligand binding assays such as those described in U.S. Pat. No. 5,164,297 and Perez et al. Nature Biotechnol. 2002, 20(8):816-20. The fluorochrome compounds can also be used for cell sorting and counting applications.

The fluorochrome compounds can also be used as reporter groups in a nucleic acid-based assays. For example, the fluorochrome compounds can be coupled to nucleic acids, for example, DNA or RNA, modified nucleic acids, PNAs, molecular beacons, or other nucleic acid binding molecules (for example, small interfering RNA or siRNA) for use in hybridization assays, for example, in situ hybridization assays, sequencing reactions, amplification reactions, for example, real-time polymerase chain reaction amplification reactions. For example, for detecting a single stranded nucleic acid (i.e., mRNA, cDNA or denatured double-stranded DNA) in a sample via nucleic acid hybridization principles, a fluorochrome compound of the invention is chemically linked to a single-stranded nucleic acid (probe) and contacted with a sample suspected of containing one or more single stranded nucleic acids (target nucleic acids), optionally immobilized on a solid support. The probe is incubated with the sample under conditions to permit the probe to hybridize to target nucleic acid in the sample to form a duplex. Unbound probe can be removed by washing, and the bound probe can be detected, wherein the presence or level of fluorescence emitted by the fluorochrome compound in the probe is indicative of the presence or amount of the target nucleic acid in the sample.

(c) Ex Vivo Applications

In addition, it is appreciated that the fluorochrome compounds can be used in a variety of ex vivo assays, for example, binding experiments, and ex vivo imaging experiments. It is understood that the imaging technologies discussed in the previous sections are also applicable to ex vivo imaging experiments.

An exemplary ex vivo imaging method comprises: (a) contacting a sample with a probe comprising a fluorochrome compound of the invention; (b) allowing the fluorochrome compound to (i) become activated by and/or (ii) bind to a biological target; (c) optionally removing unactivated or unbound fluorochrome compound; (d) exposing the sample to electromagnetic radiation, for example, light, of a wavelength absorbable by the fluorochrome compound; and (e) detecting signal emitted from the fluorochrome compounds thereby to determine whether the probes have been activated or bound by the biological target.

The sample can be a liquid or solid sample containing, for example, primary cells, cell cultures, or tissue. The biological target can be, for example, a cell, an aggregation of cells, a tissue or tissue sample, a structure (both on the macrocellular level (for example, bone organ or tissue) or on a subcellular level (for example, a mitochondria or nucleus)), and a cellular component, for example, a protein (for example, an enzyme or structural protein), lipid, nucleic acid or polysaccharide.

The invention will now be illustrated by means of the following examples, which are given for the purpose of illustration only and without any intention to limit the scope of the present invention.

EXAMPLES

Representative materials and methods that may be used in preparing the compounds of the invention are described further below. All commercially available chemicals and solvents (reagent grade) are used as supplied without further purification in general. Analytical and preparative HPLC methods include:

A Column: Agilent Zorbax 80 Å, Extend C18, 4.6×250 mm (5 μm).

Mobile phase: Acetonitrile, 25 mM triethylammonium acetate.

B Column: Varian Dynamax, 100 Å, C18, 41.4×250 mm.

Mobile phase: Acetonitrile, 25 mM triethylammonium acetate.

C Column: Phenomenex Jupiter, 300 Å, C18 Mobile phase: Acetonitrile, 25 mM triethylammonium acetate.

Example 1—Synthesis of Compound 1g

Synthesis of Compound 1g as the reactive N-hydroxy succinimidyl ester (NHSE) of formula 1 was accomplished through multi step synthetic procedures as depicted in the scheme 3A below.

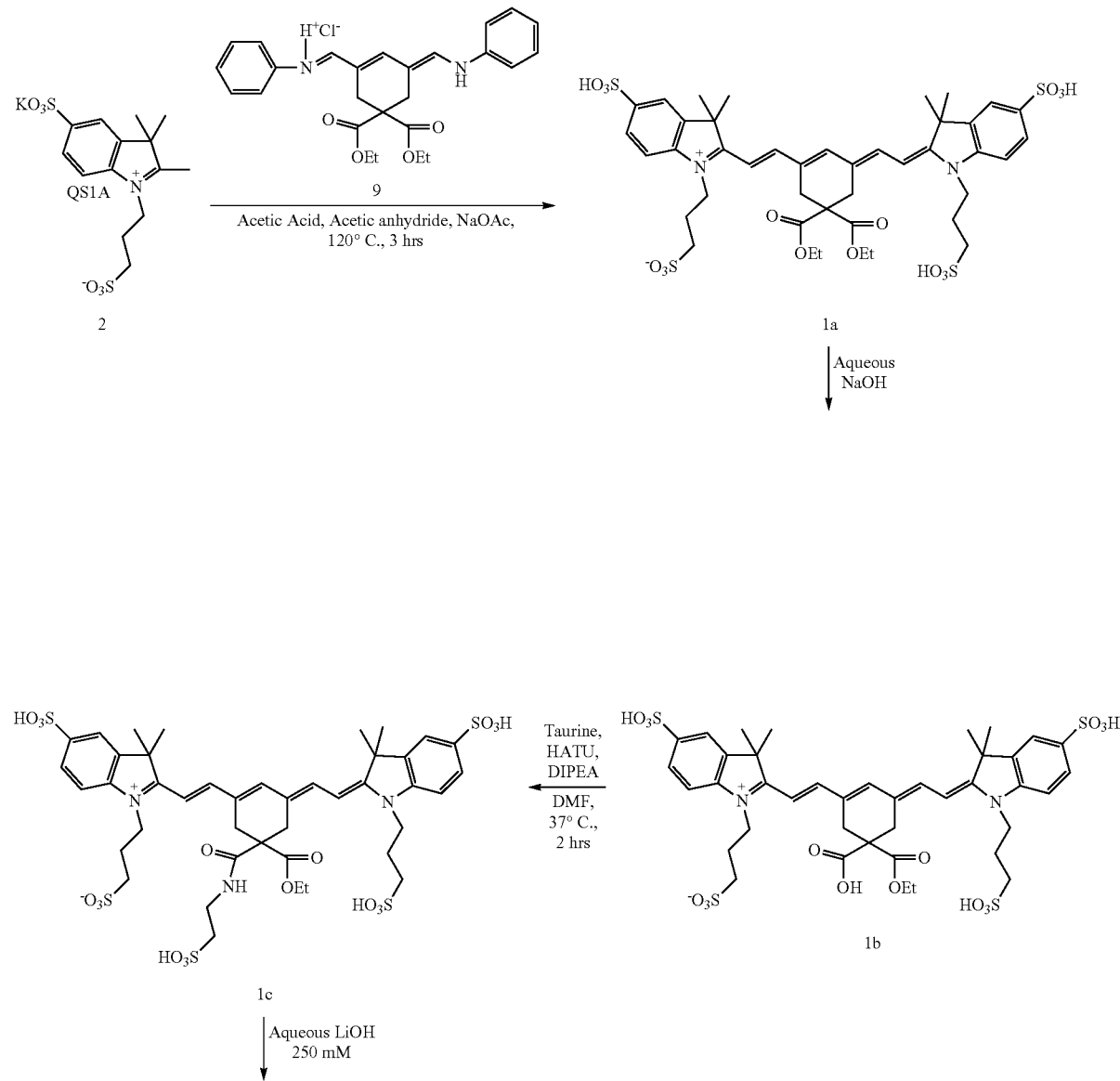

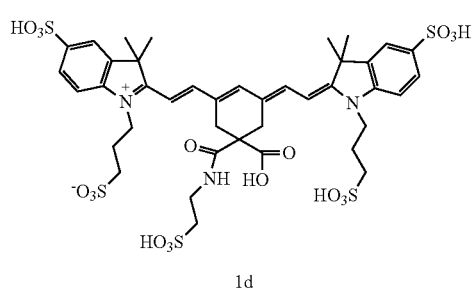

1d

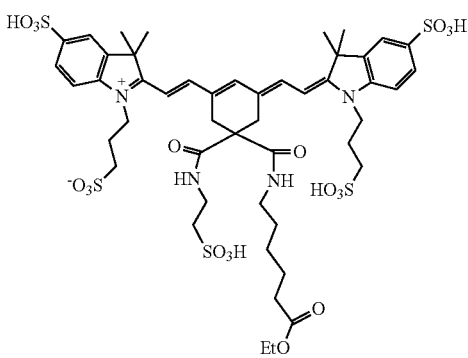

1e

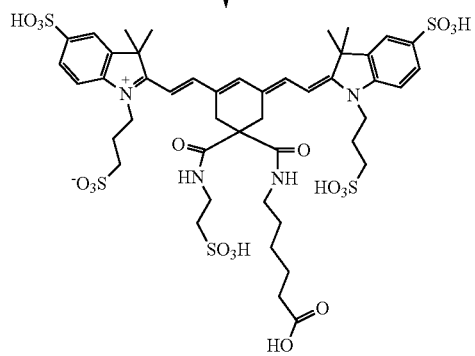

1f

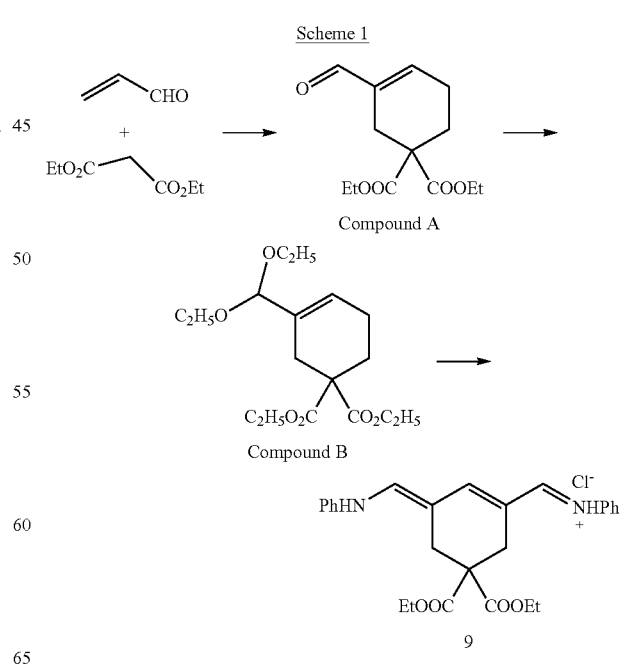

Scheme 1

1g

Preparation of QS1A:

5-sulfo-2,3,3-trimethyl indolinine as potassium salt (1) was obtained from Syntharo Fine Chemicals, Germany. 10 g of the indolinine (compound 1), dried in an oven at 110° C. for a minimum of 3 hrs was reacted with 1.5 equivalent of 1,3-propane sultone (TCI America), in 10 mL of N-methyl pyrrolidinone (Aldrich) by heating in a 100 mL round bottom flask for 8 hrs on an oil bath at 120° C. with constant stirring magnetically. Yellow reaction mixture turned dark purple and the product precipitated out of the solution. After cooling to room temp, ethyl acetate was added to the reaction mixture (RM) and sonicated for 5 min. The precipitate was filtered, washed three times with ~100 mL of 90%-10% mixture of ethylacetate (EA)-methanol, and then dried under vacuum for 4 hrs. The quaternary salt QS1A obtained in 90% yield was characterized by LCMS (m/e calculated: 361 (as free sulfonic acid); found: 361 (M+1)).

Preparation of Bisanil 9:

Compound 9 was prepared in three steps as shown in the scheme below by following the procedure of Deroover et. al described in the U.S. Pat. No. 5,876,915 (dated Mar. 2, 1999). The intermediates A and B were isolated by distillation in 13 g and 10 g respectively. Compound B was converted to compound 9 by Vilsmeier reaction, and the product was isolated as dark red solid by filtration and drying under vac for an overnight.

Preparation of Compound 1a:

Compound 9 (100 mg, 0.214 mmol) and compound QS1A (171 mg, 0.418 mmol) were mixed in 2.5 mL acetic acid and 7.5 mL of acetic anhydride. After sonicating for two minutes, 35 mg of sodium acetate was added, and the mixture was heated at 120° C. with stirring for 4 hrs. Ethyl acetate (25 mL) was added, and the solid centrifuged, which was washed with an additional 5 mL of EA, centrifuged, and the solid dried on speed vac for 30 minutes. The crude dye was purified by HPLC on reversed phase (RP) C18 column, using 10-50% triethyl ammonium bicarbonate (TEAB)-acetonitrile (ACN) system. The purified product was characterized by LCMS. Mass calculated: 968.2 (as free sulfonic acid); Mass found: 969.2 (M+1); Yield: 50%.

Preparation of 1b:

To 50 mg of purified compound 1a dissolved in 0.8 mL of distilled water was added 0.8 mL of 1M sodium hydroxide, and the reaction mixture was rotated at room temp in dark. After 90 minutes, 1 mL of 50% aqueous acetic acid was added. Pale yellow reaction mixture turned greenish blue upon acidification. It was purified on RPC18 column, using 10-50% TEAB-ACN system. The pure product was identified to be the mono acid ester by LCMS. Mass calculated: 940.2 (as free sulfonic acid); Mass found: 941.1 (M+1); Abs 749 nm; Em 771 nm; ε 240,000 (1×PBS); Yield 80%.

Preparation of 1c:

40 mg of dried compound 1b was dissolved in 0.5 mL of dry DMF in a 2 mL polypropylene centrifuge tube. 25 mg HATU, 25 mg 2-aminoethanesulfonic acid (Taurine) and 25 uL of N,N-disopropyl ethylamine (DIPEA) were added and allowed to react at 37° C. for 1 hr. The completion of the reaction was indicated by LCMS. The crude reaction mixture was diluted with 2 mL of 25% aqueous acetic acid and purified on RPC18 column using 10-40% Triethyl ammonium acetate (TEAAc, pH 6.6)-ACN system. Mass calculated: 1047.2 (as free sulfonic acid); Mass found: 1048.1 (M+1). Abs. max: 749 nm in water. Yield: 70%.

Preparation of 1d:

30 mg of compound 1c was treated with 250 mM lithium hydroxide solution at room temp. The saponification was complete in 2 hrs. The resulting acid product was purified on RPC18 column using 5-25% TEAAc-ACN system. Abs. max: 751 nm; Em. Max: 771 nm (in water/1×PBS). Mass calculated: 1019.2 (as free sulfonic acid); Mass found: 1020.1 (M+1); Yield: 70%.

Preparation of 1e:

20 mg of dried compound 1d was reacted with a mixture of HATU (20 mg), Ethyl-6-amino hexanoate hydrochloride (25 mg), and DIPEA (15 uL) in DMF (500 uL) at 37° C. for 45 minutes. After diluting with 1 mL of 25% aqueous acetic acid, it was purified by HPLC on RPC18 column using 10-40% TEAAc-ACN system. Mass calculated: 1160.3 (as free sulfonic acid); Mass found: 1161.2 (M+1). Abs max: 751 nm; Em. Max: 771 nm (in water/1×PBS). Yield: 75%.

Preparation of 1f: Compound 1e was treated with 250 mM lithium hydroxide solution at room temp. The saponification was complete in 1 hr. The resulting acid product was purified by HPLC on RPC18 column using 5-30% TEAAc-ACN system. Abs. max: 751 nm; Em. Max: 771 nm (in water/1× PBS). Mass calculated: 1132.2 (as free sulfonic acid); Mass found: 1133.3 (M+1). Yield: 85%.

Preparation of 1g:

To 5 mg of dried compound 1f was added disuccinimidyl dicarbonate (10 mg) and 250 uL dry DMF was added followed by an addition of 5 uL N-methylmorpholine. The NHSE ester formation was complete in about 2 hrs as revealed by a test reaction with butylamine and analyzing by HPLC-LCMS. The NHSE was isolated by precipitation in ethylacetate, and speed vac drying for 60 min.

The procedure described above for the compounds 1a through 1g are used for the compounds synthesized in schemes 3B through 3S.

General Procedure for the Preparation of Quaternary Salts

The N-(propane-3-sulfonate) quaternary salts of indoles, benzindoles, benzoxazoles and benzthiazoles (compounds 2-5, and 10) were prepared by reacting the heterocycles (5 mmol) with 1,3-propane sultone (7.5 mmol) in 1,2-dichlorobenzene or N-methyl pyrrolidonone as indicated in the scheme and heating at 120° C. with stirring for 8 hrs. The product always formed as solid and was isolated by filtration and washings with suitable organic solvent mixture (hexane followed by ethylacetate or ethylacetate). They were characterized by LCMS.

Similarly the N-Ethyl quaternary salts of the compounds 1-5, and 10 were prepared by reacting the heterocycles (5 mmol) with ethyliodide (15 mmol) in 1,2-dichlorobenzene or N-methyl pyrrolidonone as indicated in the scheme and heating at 120° C. in a pressure tube for 8 hrs with stirring. The product always formed as solid and was isolated by filtration and washings with suitable organic solvent mixture. Hexane followed by ethylacetate was used for reactions involving 1,2-dichloro benzene, and only ethylacetate was used for the reactions involving N-methyl pyrrolidinone. The products were all characterized by LCMS.

The procedure described above for compounds 1a to 1g are followed for the synthesis of compounds depicted in the synthetic schemes: 3B, 3C, 3D, 3E, 3F, 3G, 3H, 3I, and 3J.

Example 2: Synthesis of Asymmetric Dye

Preparation of QS1C:

Scheme 3K-1

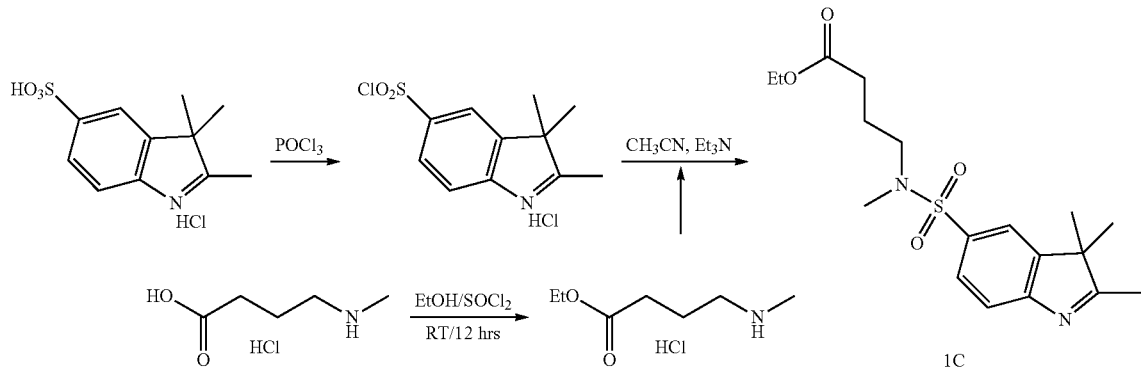

10 mmol of compound 1 (as acid) was heated with 10 mL of POCl$_3$ to reflux for 2 hrs. To the cooled reaction mixture 25 mL n-hexanes were added, and the organic supernatant was safely discarded. The gummy solid was rotovap dried under vacuum for several hours to remove the residual phosphorous oxychloride. The sulfonylchloride was used as such in the next step. Yield: 99%.

50 mmol of 4-(N-methyl)-aminobutyric acid hydrochloride was converted to ethyl ester by dissolving in 100 mL of absolute ethanol, and carefully adding thionyl chloride (55 mmol) at room temp with vigorous stirring. The reaction was allowed to proceed over 12 hrs at room temp. Nitrogen was flushed into the reaction flask and bubbled through the solution for 10 min. Solvents were removed by rotovap, and the resulting white solid was dried under high vacuum for 12 hrs.

The Ethyl (4-(N-methyl))-aminobutyrate hydrochloride as obtained above was dissolved in 100 mL dry acetonitrile and cooled to 5° C. 10 fold excess of triethylamine was added and stirred vigorously. The sulfonyl chloride was dissolved in 30 mL of acetonitrile, and was added slowly to the stirring solution over 10 min during which the solution turned yellow. Reaction was complete in 30 min. and was allowed to warm up to room temp. The white triethylamine hydrochloride was filtered off and washed with cold acetonitrile. The filtrate was concentrated, and the residue was chromatographed on silica gel using 3% ACN-94% CH$_2$Cl$_2$-3% TEA mixture for elution. The product 1C eluted when the eluent used was 5% ACN-92% CH$_2$Cl$_2$-3% TEA. It was characterized by LCMS. Yield: 75%.

Compound 1C was converted to the quaternary salt QS1C by following the general procedure described for the synthesis of quaternary salts, using 1,2-dichlorobenzene as the solvent. Yield: 75%

General Procedure for the Synthesis of Asymmetric Dyes:

In schemes involving the synthesis of asymmetric dyes using two different quaternary salts derived from two different heterocycles, the procedure described for compound 1a was followed except that the bisanil (compound 9), the two quaternary slats each were used in equimolar amounts. Everything else remained essentially the same.

Figure 1B:
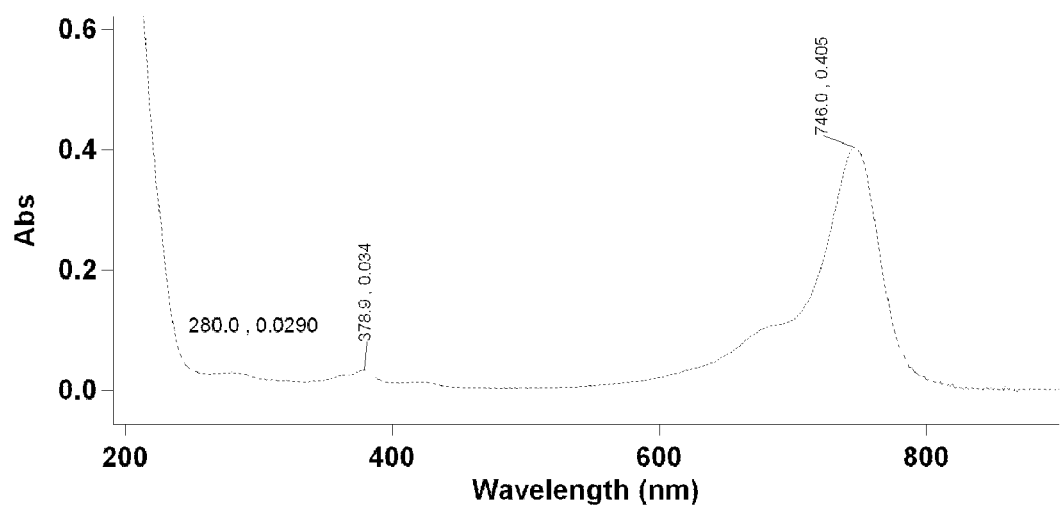

Example 3: Conjugation of Compound 1b with BSA 3 mg of BSA (44.4 nmol) was dissolved in 1.5 mL 0.4 M MES buffer at pH 5.3, and an aqueous solution of 450 nmoles of compound 1b (45 uL at 10 mM) were added followed by 25 mg of EDC. The mixture was left at 37° C. for an overnight (18 hrs). The reaction mixture was diluted with 5 mL water and filtered through Amicon Ultra-4, PLTK Ultacel-PL Membrane filter with 30 kD cutoff by centrifuging at 2000 rpm for 30 min. The product was washed a few times with 1×PBS buffer until the filtrate was colorless. The concentrated product was quantified and the dye/protein ratio was determined by the formula:

$$A_{dye}\varepsilon_p/(A_{278}-c\% A_{dye})\varepsilon_{dye}$$

where, $A_{dye}$ is the absorption of the dye at 750 nm, $\varepsilon_p$ is extinction coefficient of protein (BSA, 43824), $A_{278}$ is the absorption of the protein at 278 nm, c % $A_{dye}$ is the % absorption of the dye at 278 nm with respect to its abs. at $\lambda_{max}$, 750 nm (4%) and $\varepsilon_{dye}$ is the extinction coefficient of the dye (240,000 in 1×PBS). The product was also characterized by MALDI (Tuft's University Core Facility, Boston) and the number of dyes was determined to be 8.7 per BSA. The results of the fluorescence and absorbance determinations for Compound 1b conjugated to BSA are depicted in FIGS. 1A-1B.

Schemes

Scheme 1 for the synthesis of quaternary salts, scheme 2 and 2A for the synthesis of 4,4-disubstituted cyclohexyl bisaldehyde as Schiff's base, and 3B to 3T for the synthesis of dyes of various formulae are shown in the following pages.

Scheme 1. Preparation of Quaternary Salts

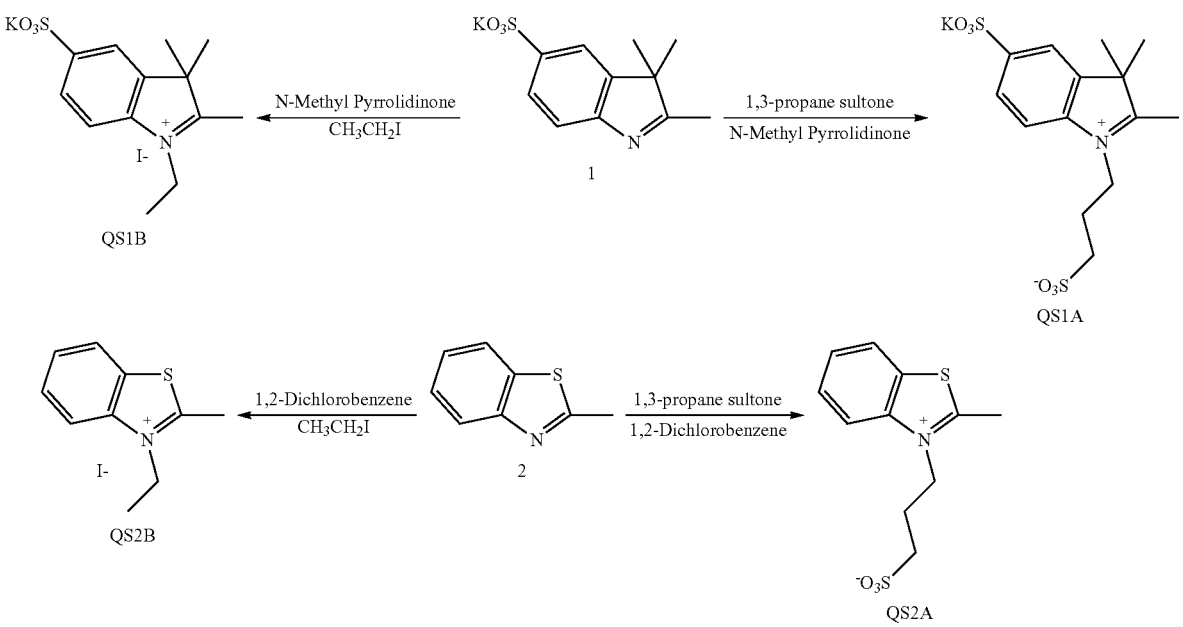

-continued
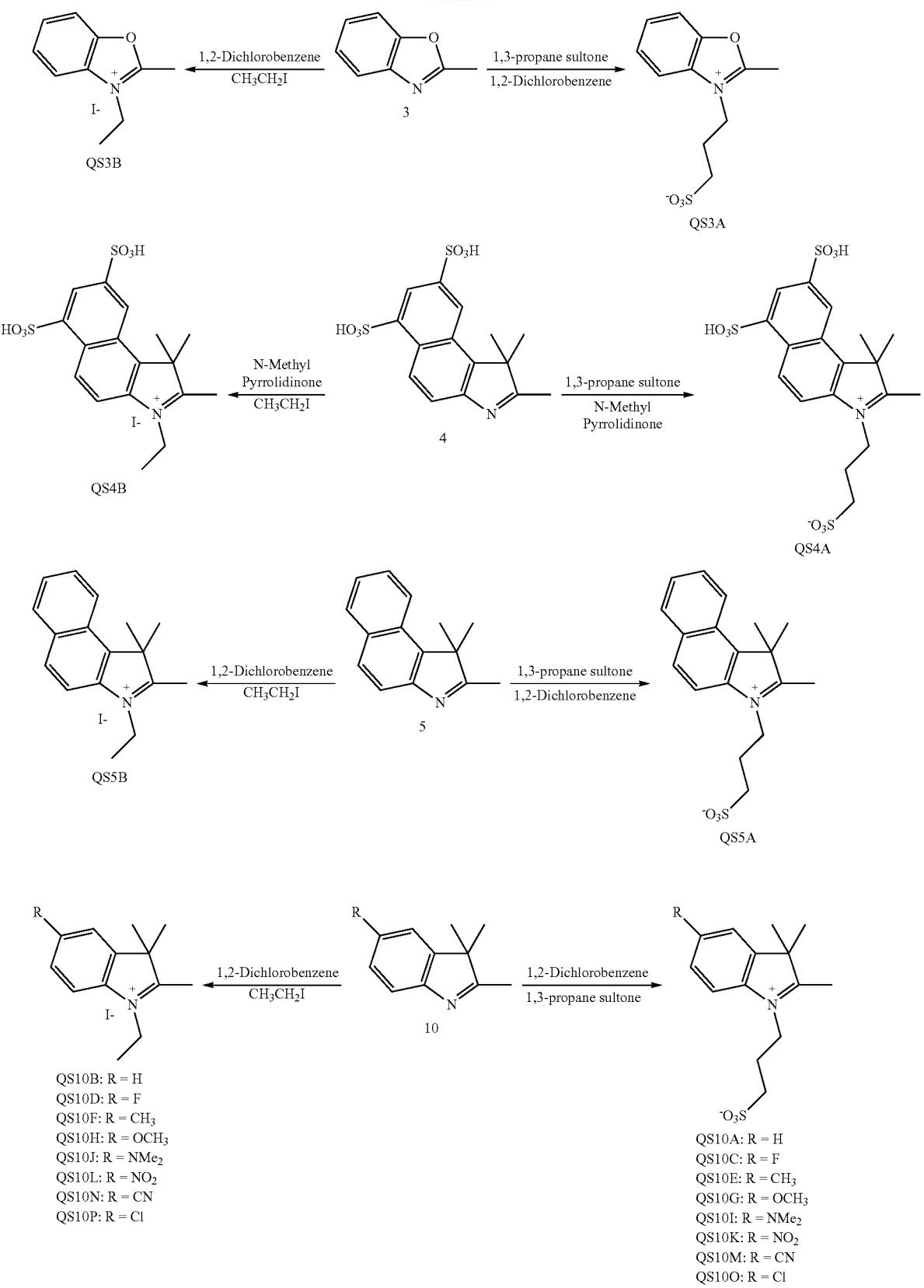

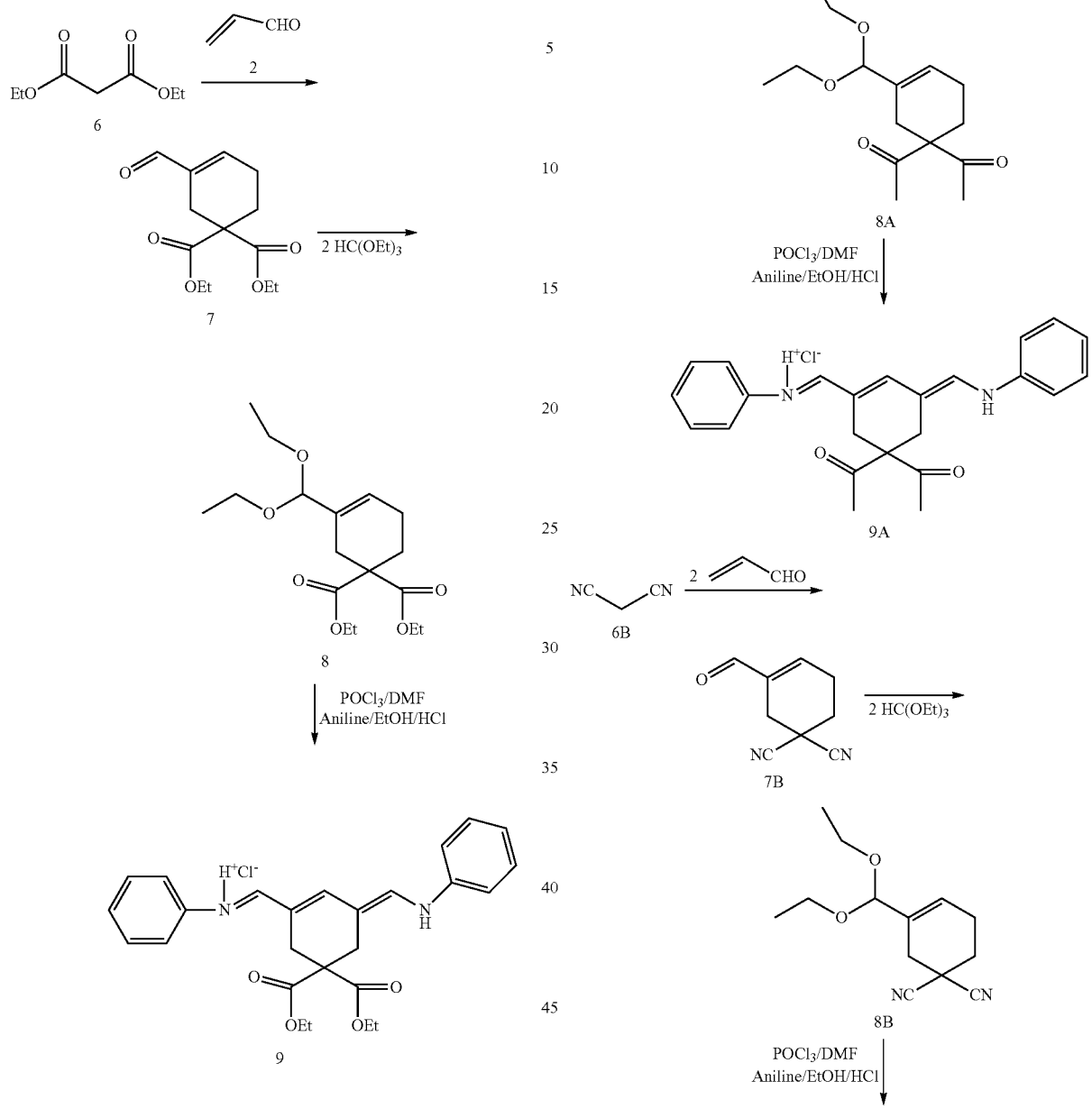
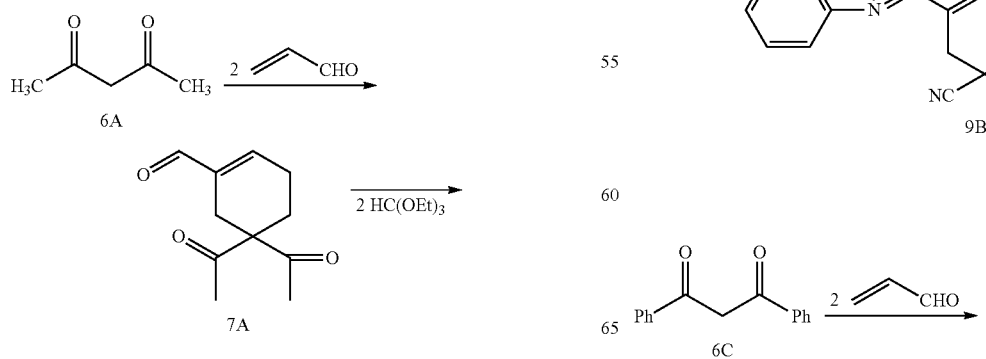

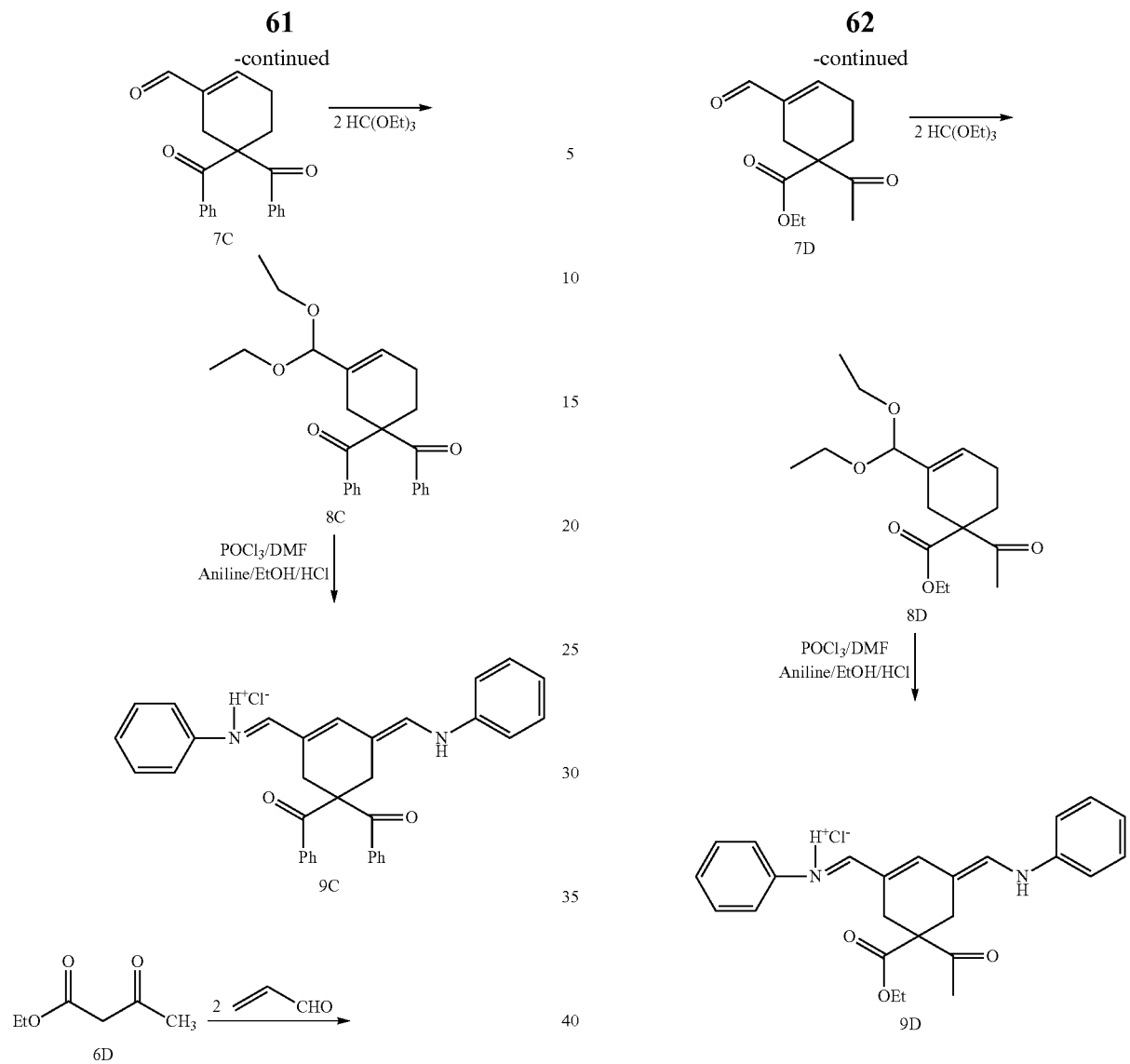
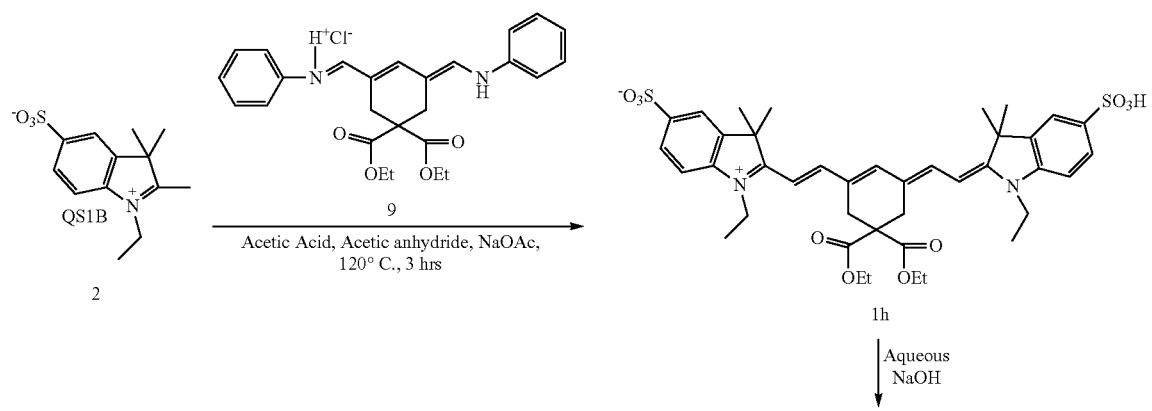
Scheme 3B. Synthesis of Symmetric Indolinium Dye

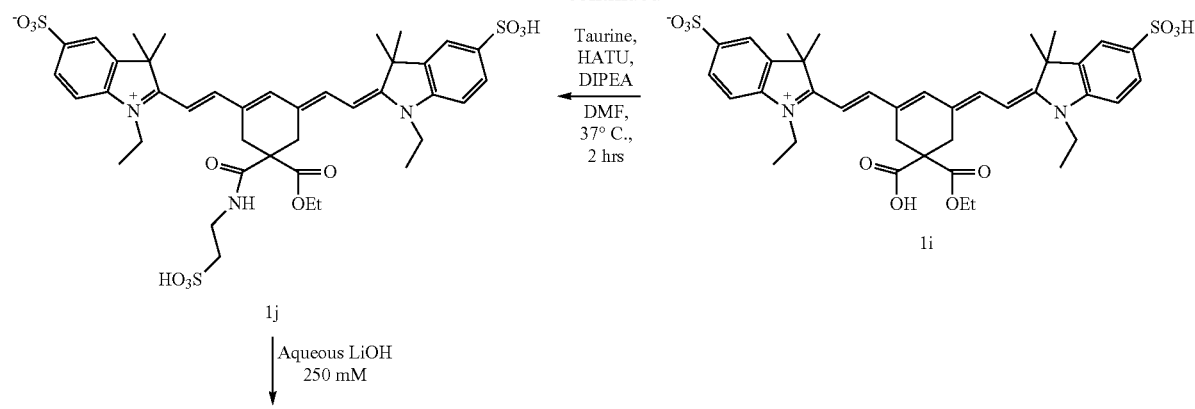
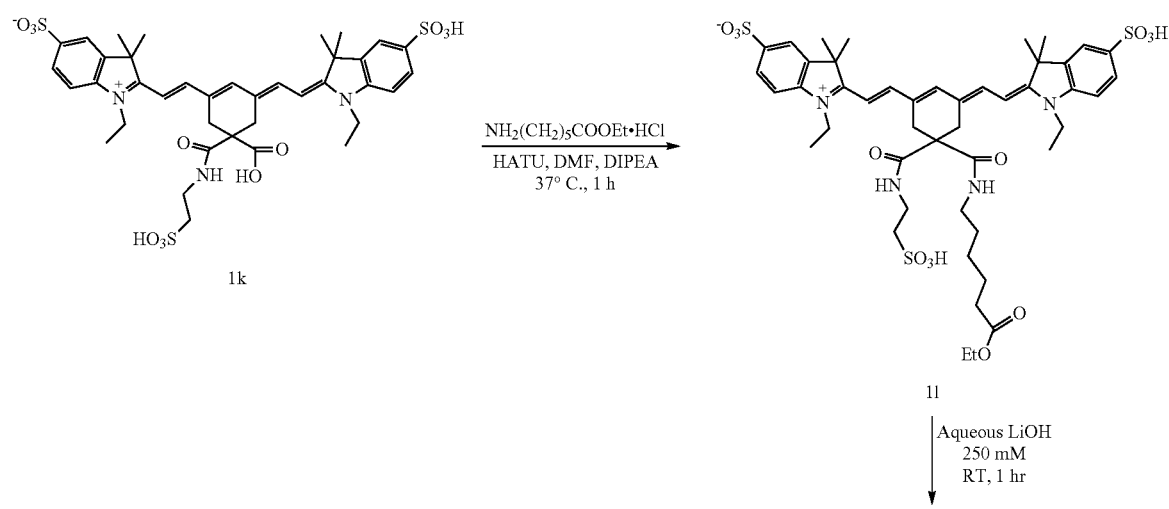
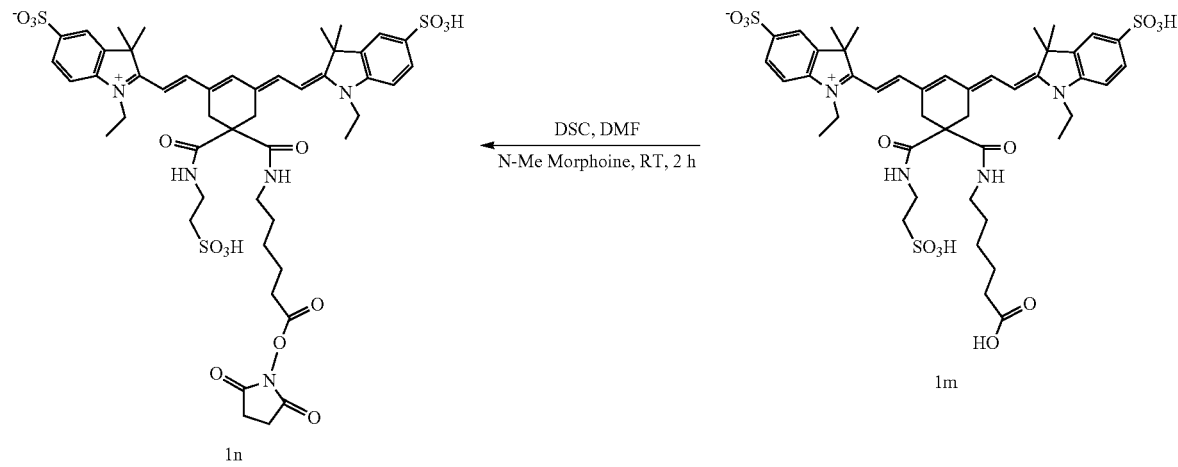

Scheme 3C. Synthesis of Symmetric Benzothiazolium Dye
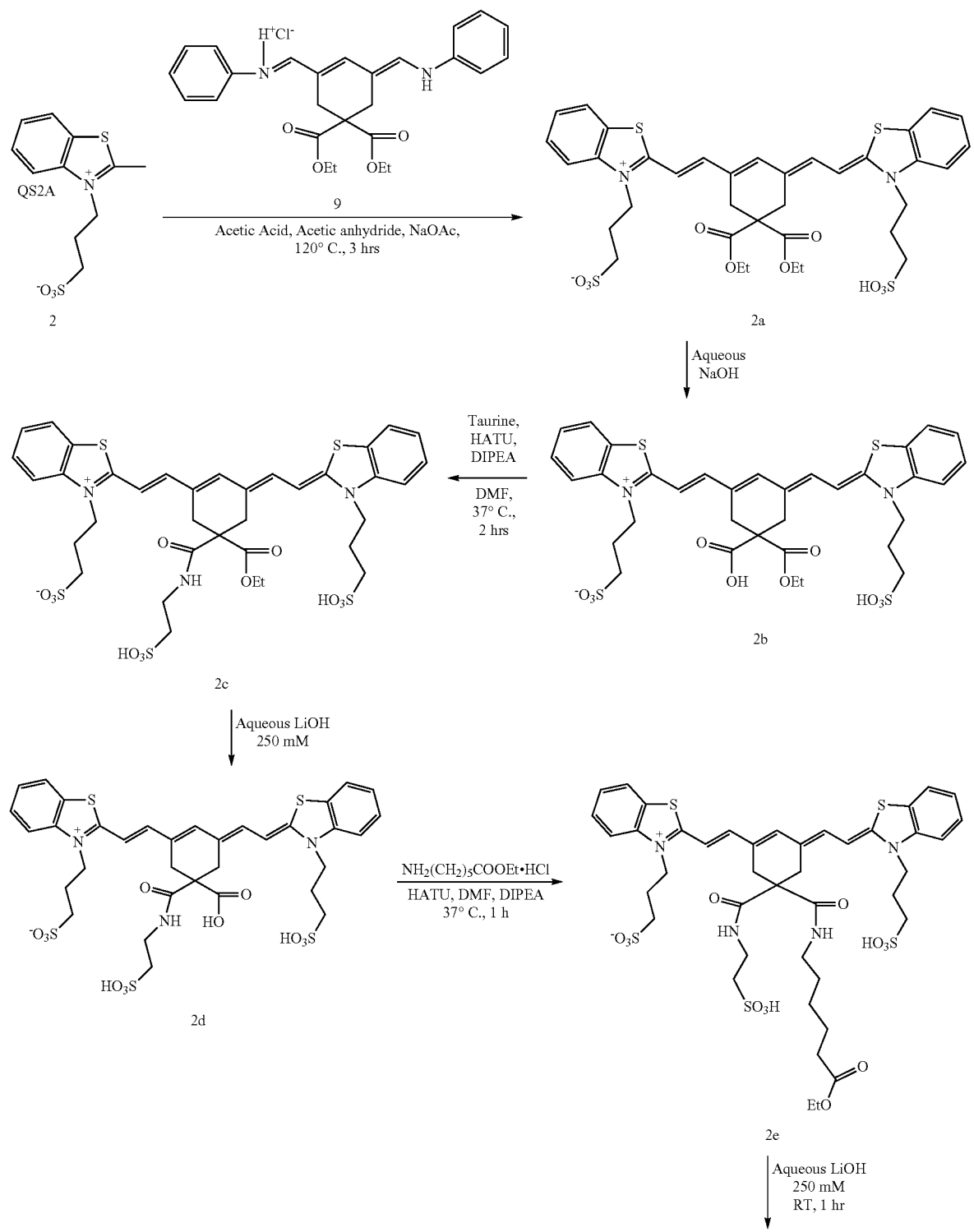

67 68
-continued
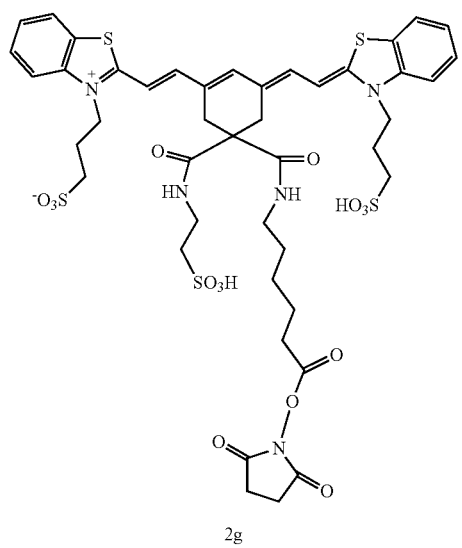
2g
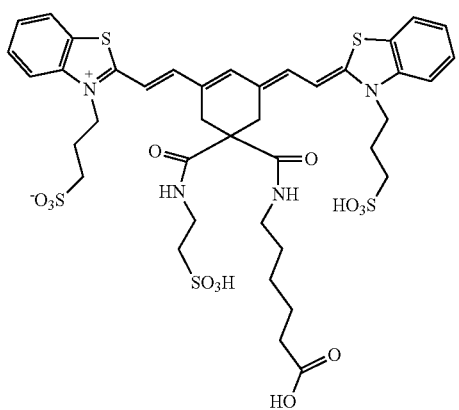
2f
DSC, DMF
N-Me Morphoine, RT, 2 h
Scheme 3D. Synthesis of Symmetric Benzothiazolium Dye
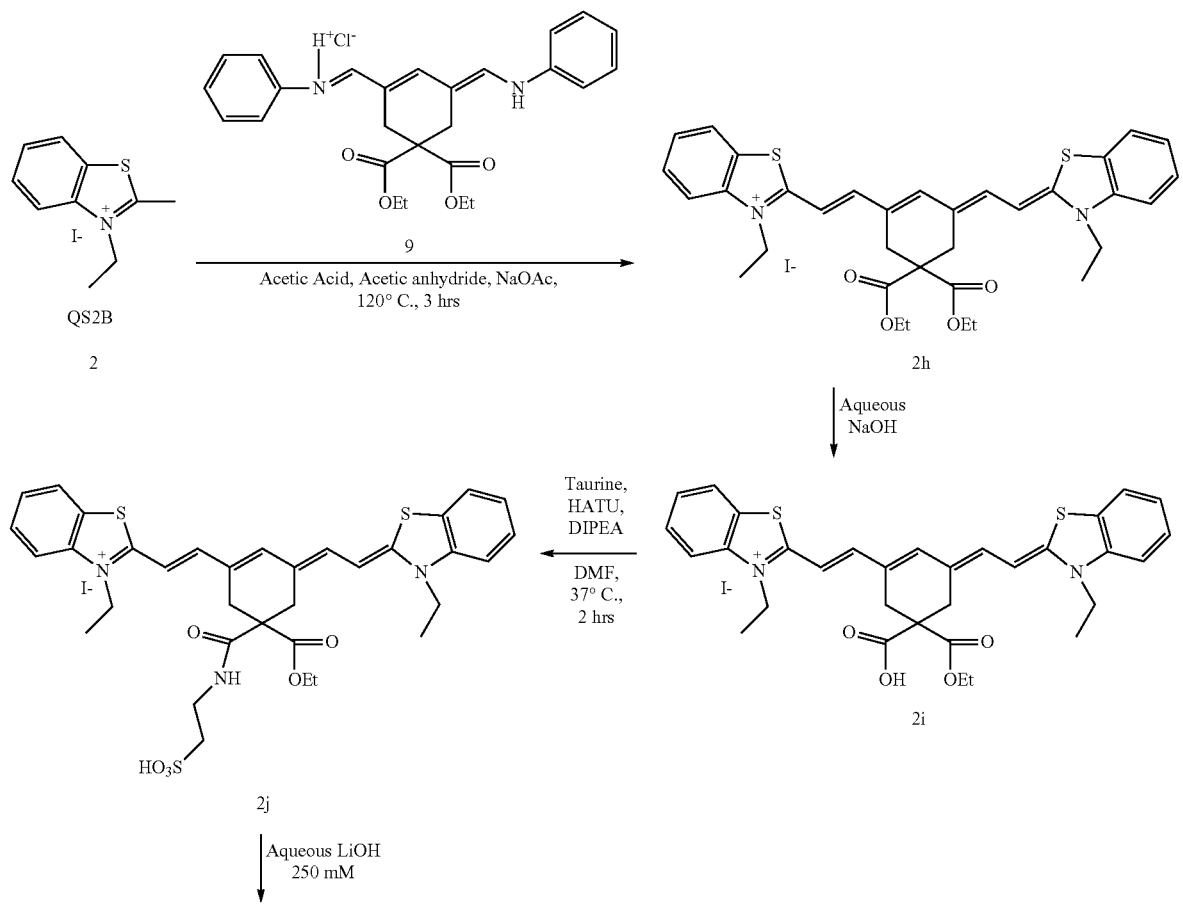

-continued
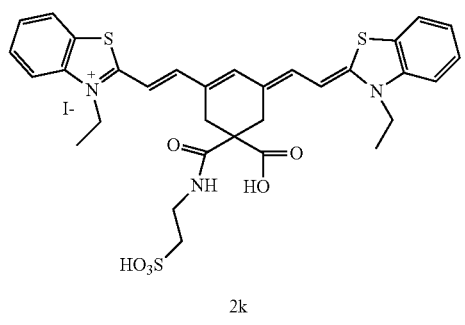
2k
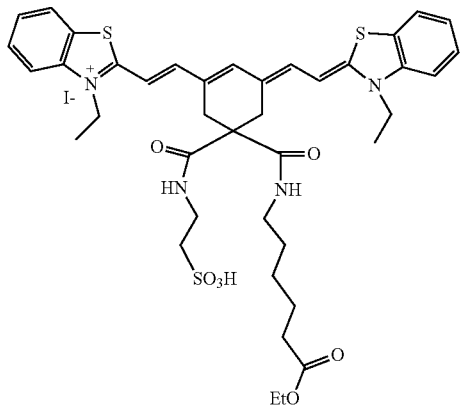
2l
NH$_2$(CH$_2$)$_5$COOEt·HCl
HATU, DMF, DIPEA
37° C., 1 h
Aqueous LiOH
250 mM
RT, 1 hr
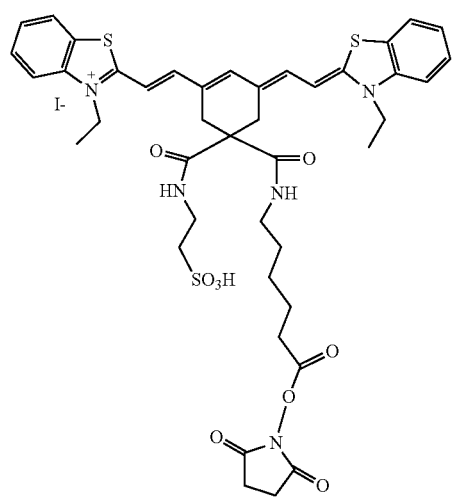
2n
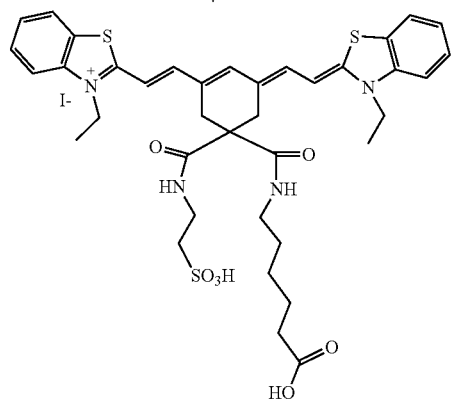
2m
DSC, DMF
N-Me Morphoine, RT, 2 h
Scheme 3E. Synthesis of Symmetric Benzoxazole Dye
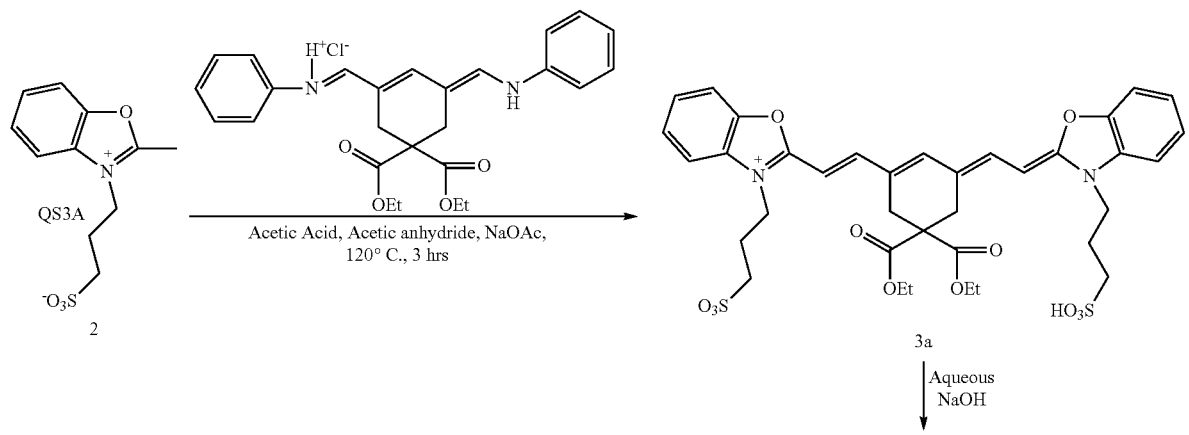
Acetic Acid, Acetic anhydride, NaOAc,
120° C., 3 hrs
Aqueous
NaOH -continued
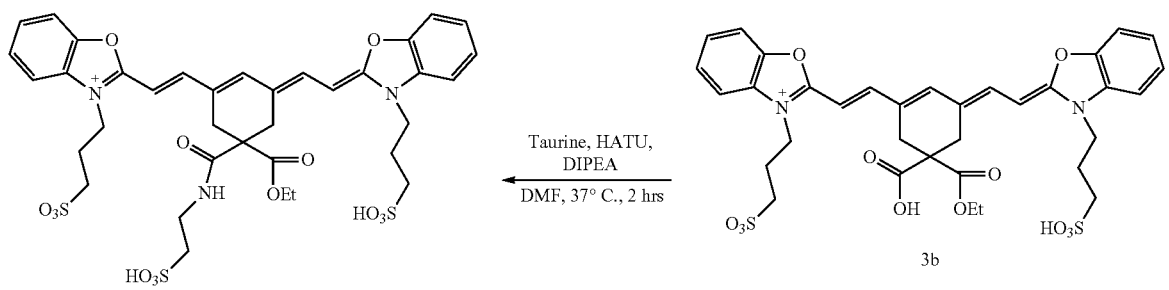
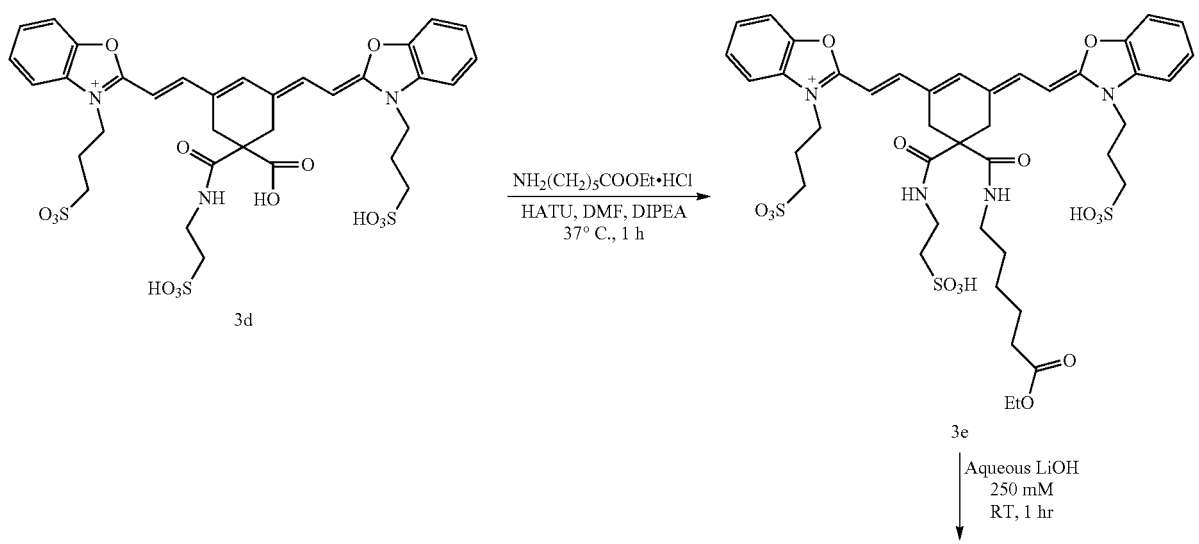
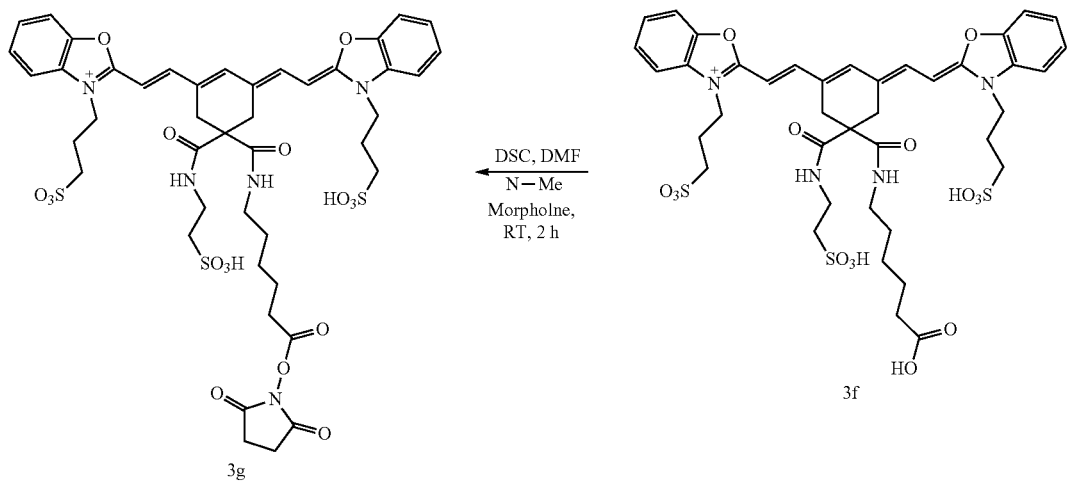

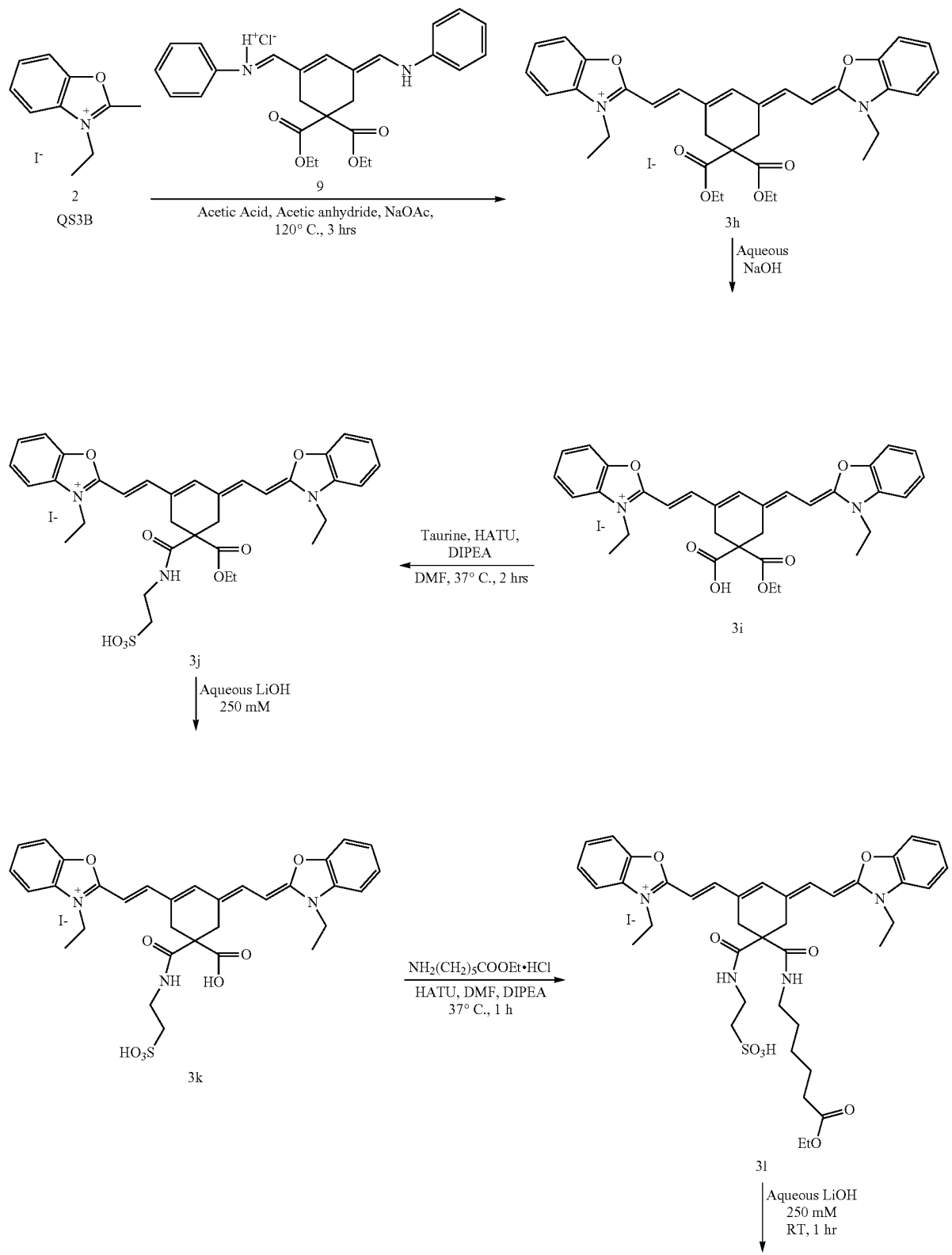
Scheme 3F. Synthesis of Symmetric Benzothiazolium Dye

75
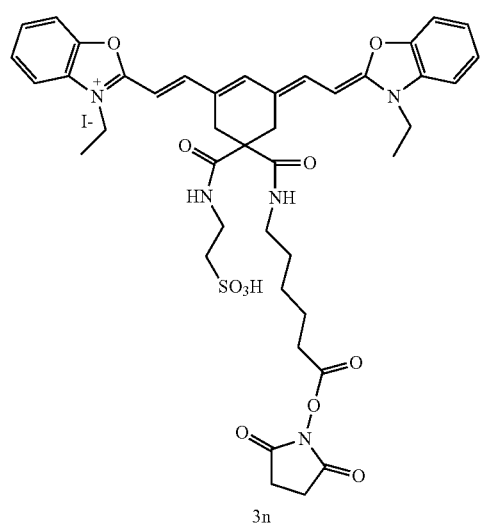
3n
76
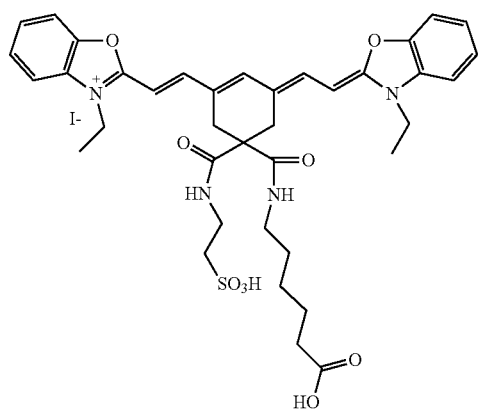
3m
DSC, DMF
N—Me
Morpholne,
RT, 2 h

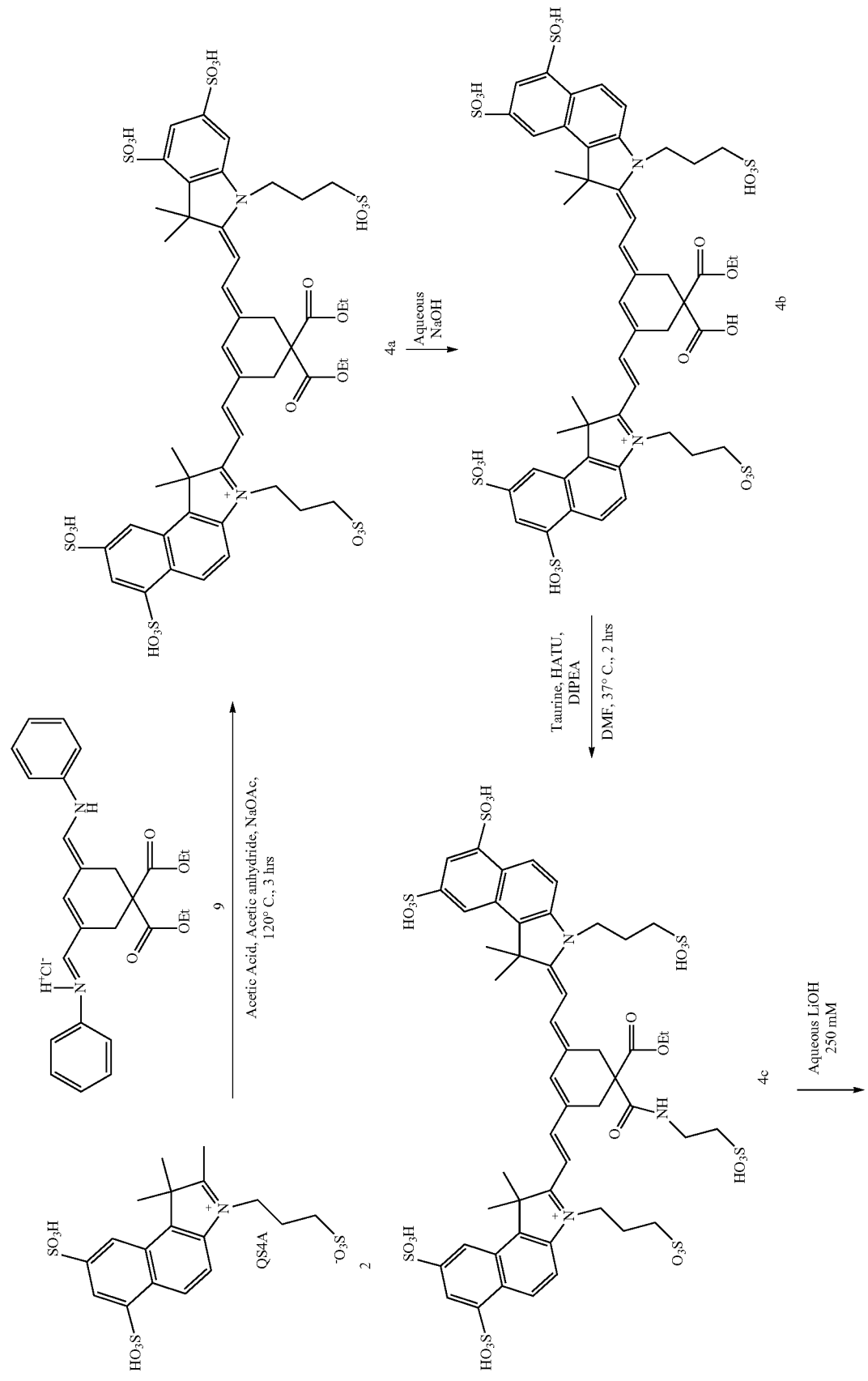

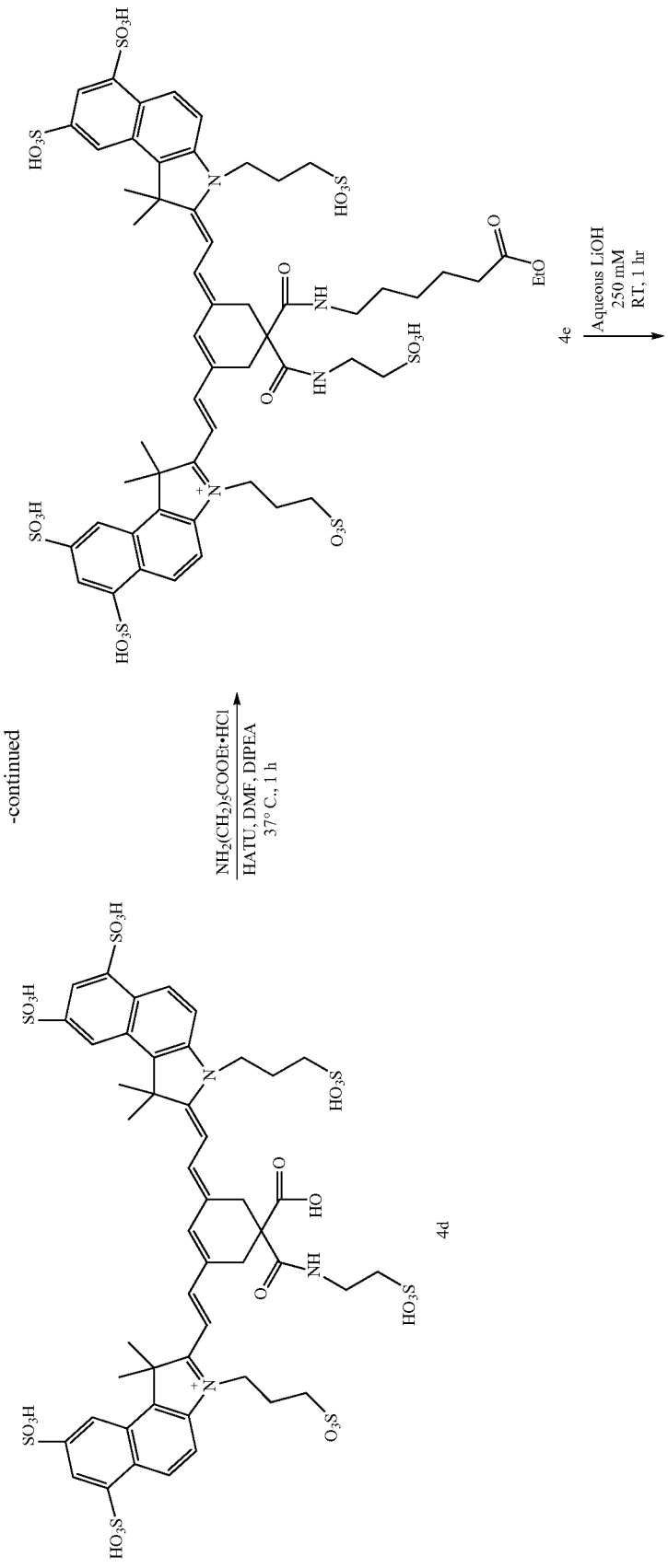

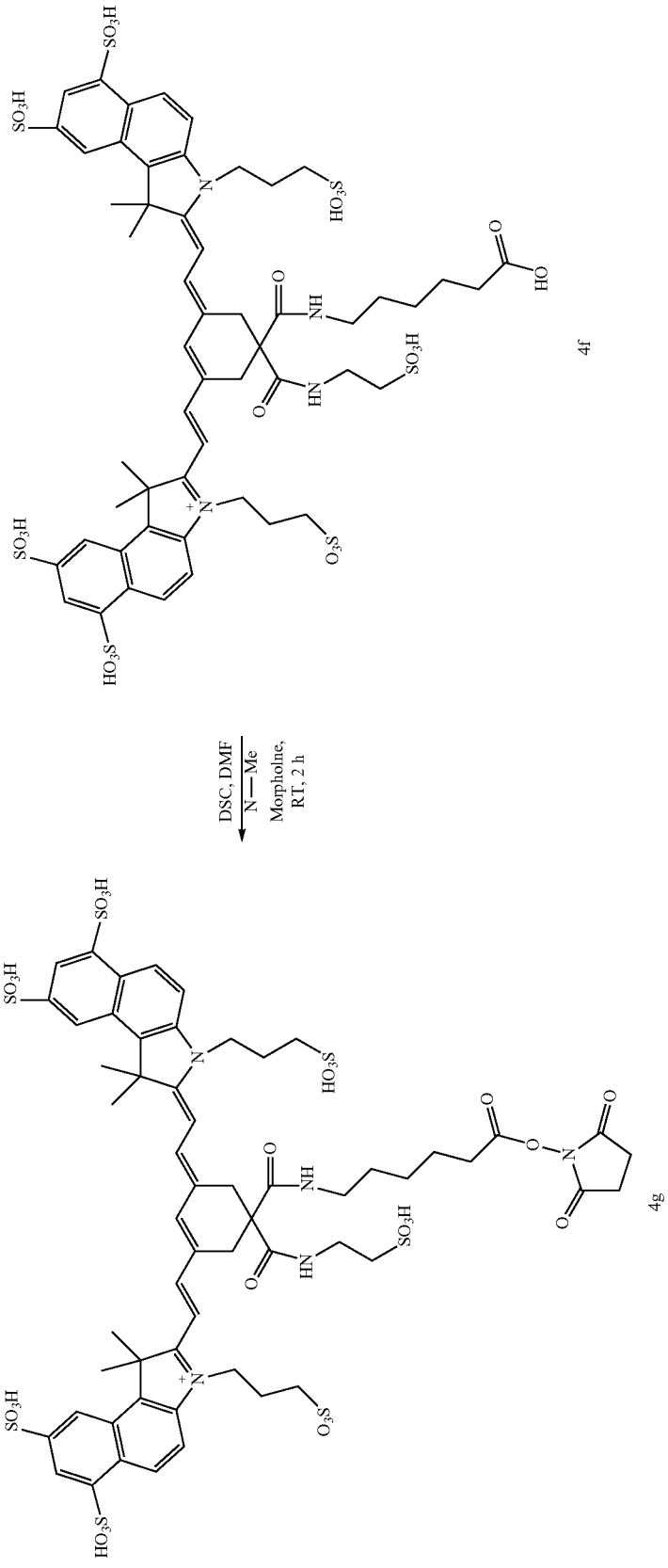

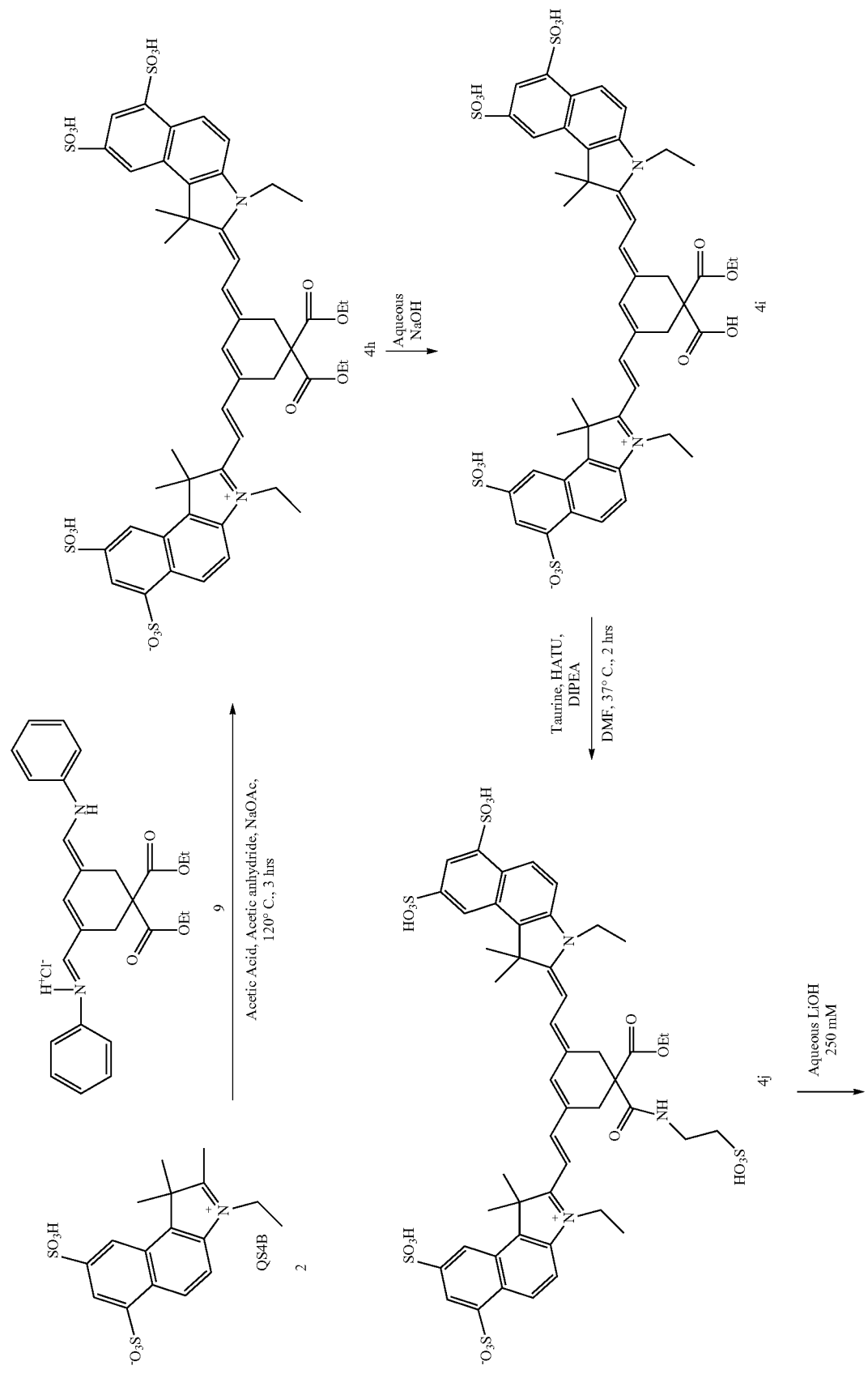

-continued
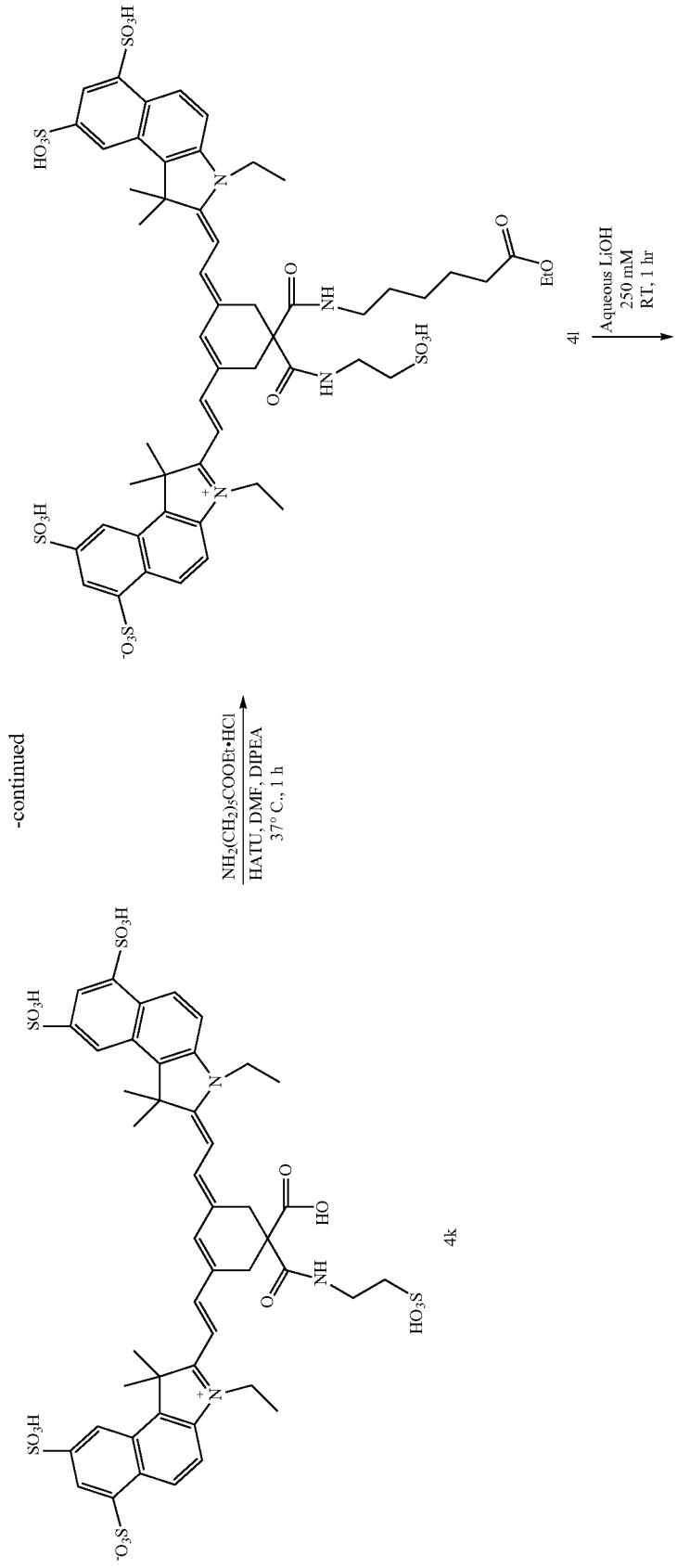

-continued
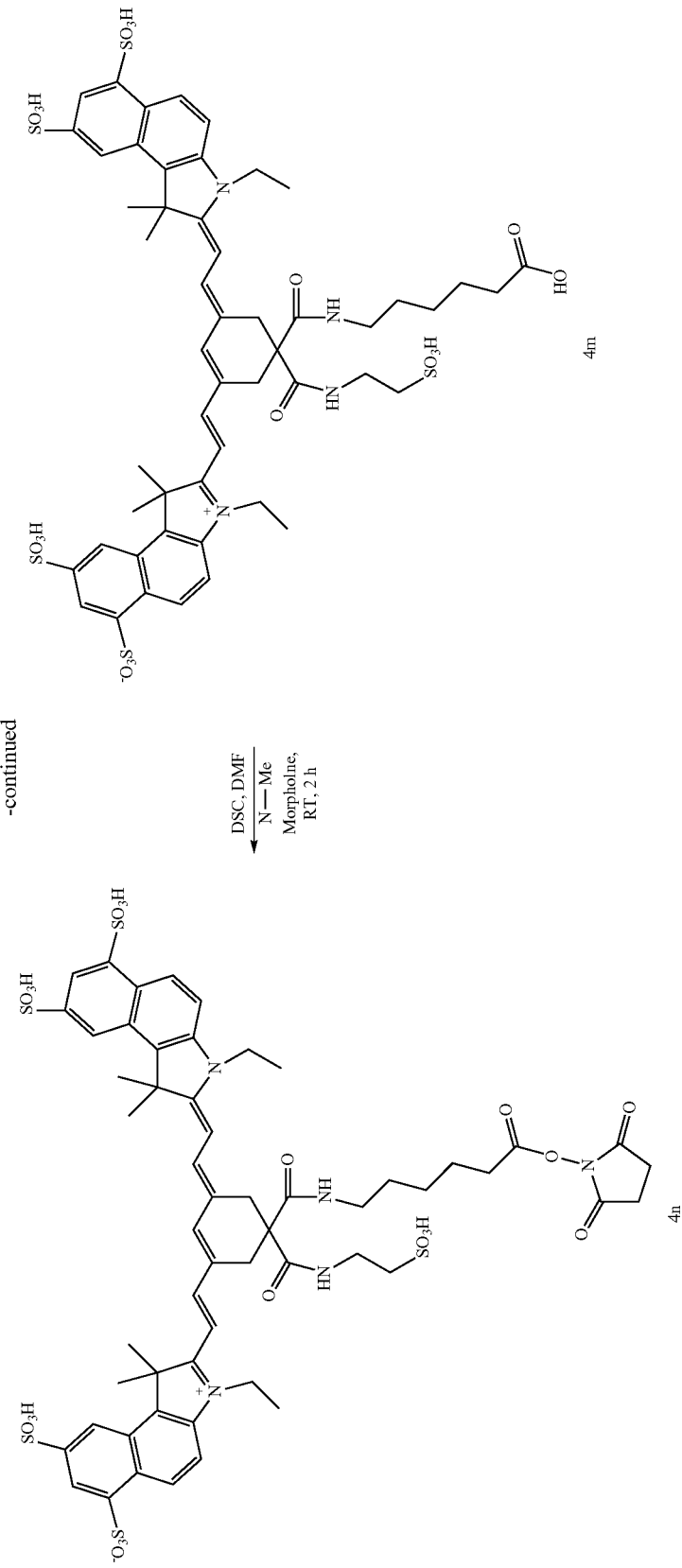

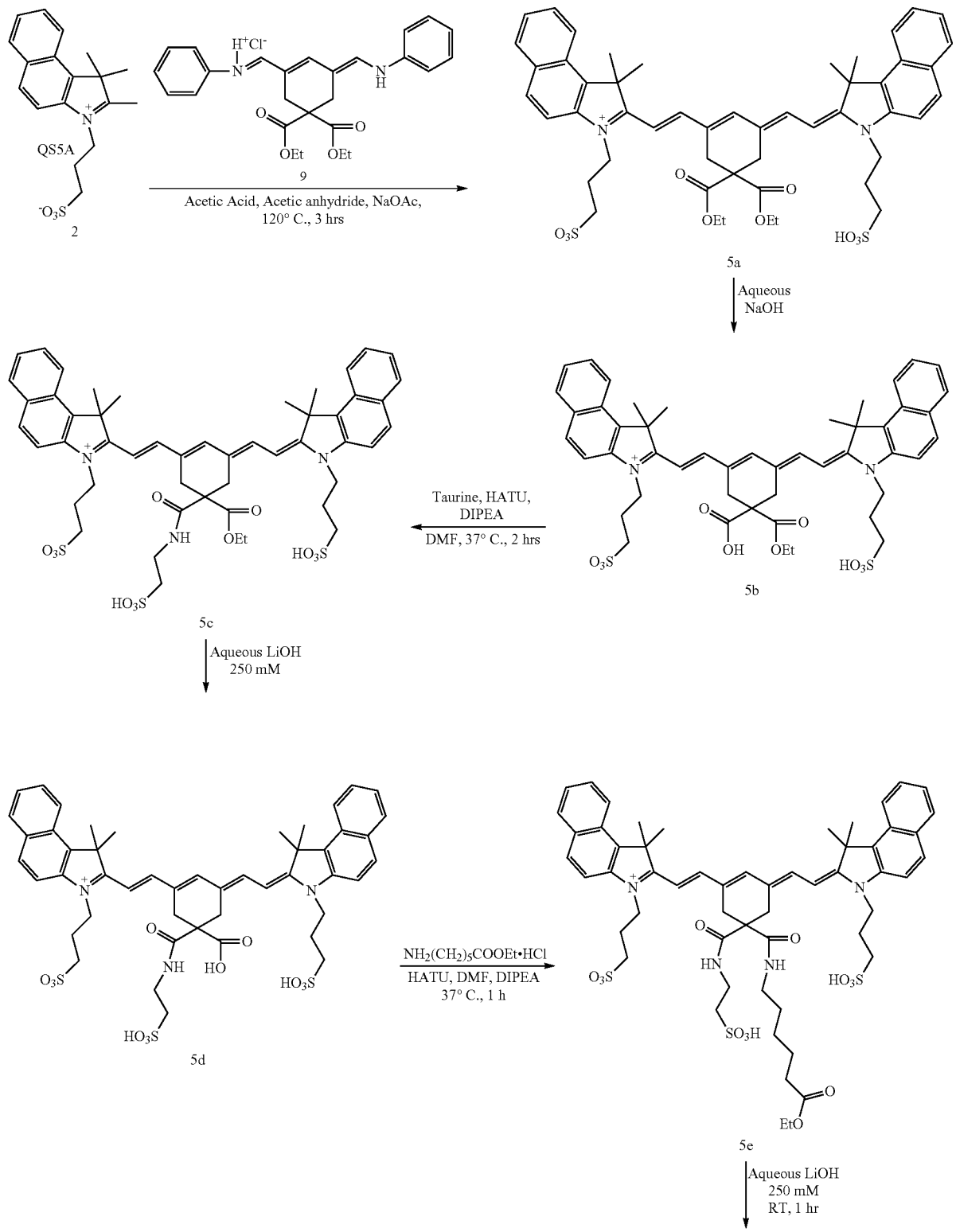
Scheme 3I. Synthesis of Symmetric Benzoxazole Dye 91 92
-continued
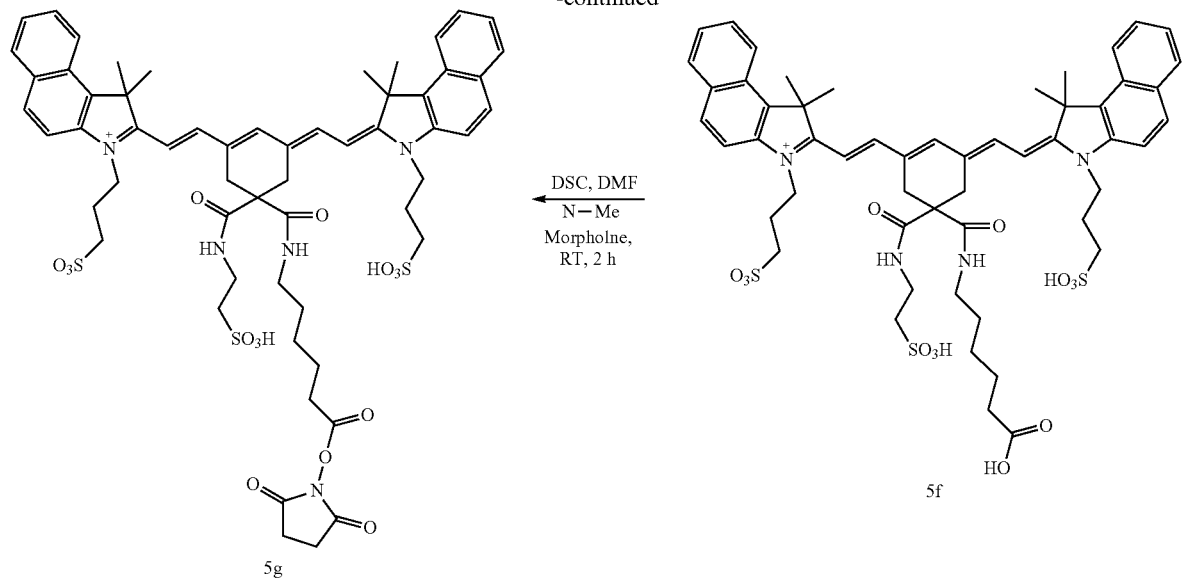
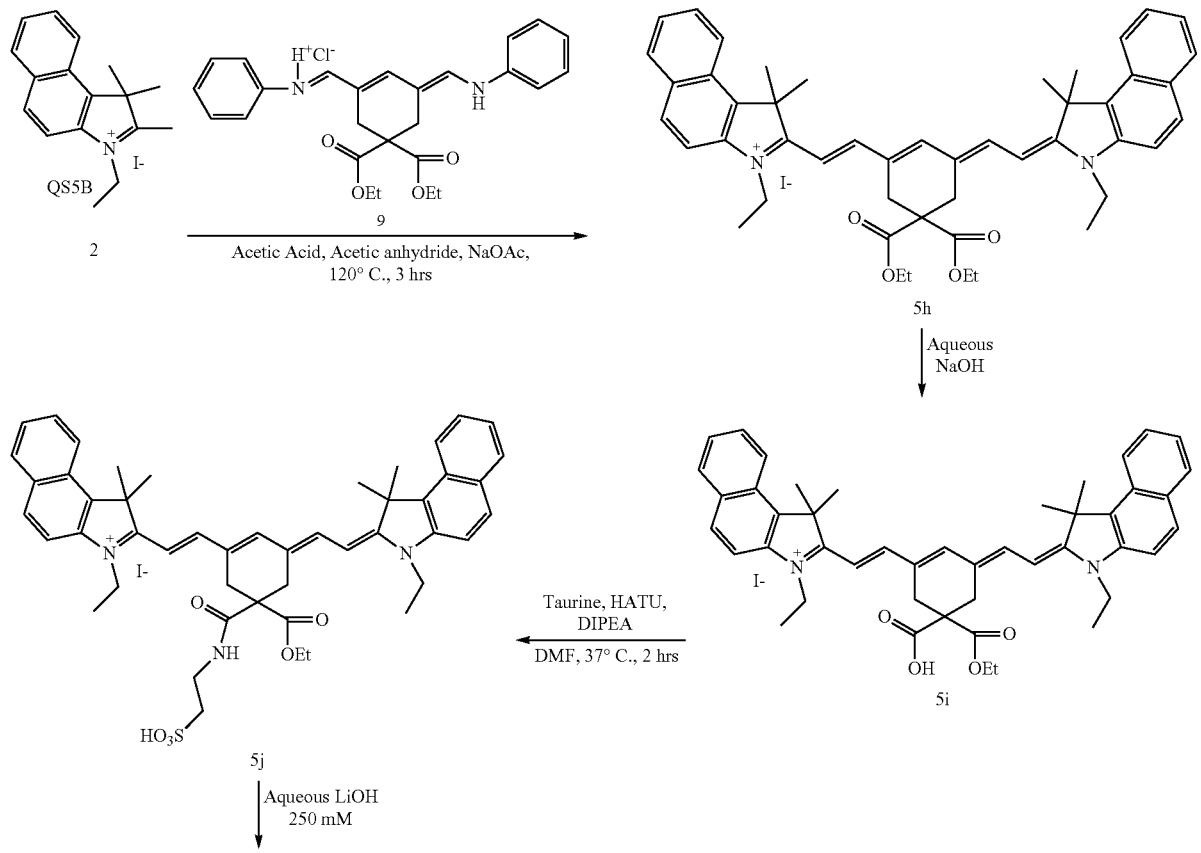
Scheme 3J. Synthesis of Symmetric Benzoxazole Dye

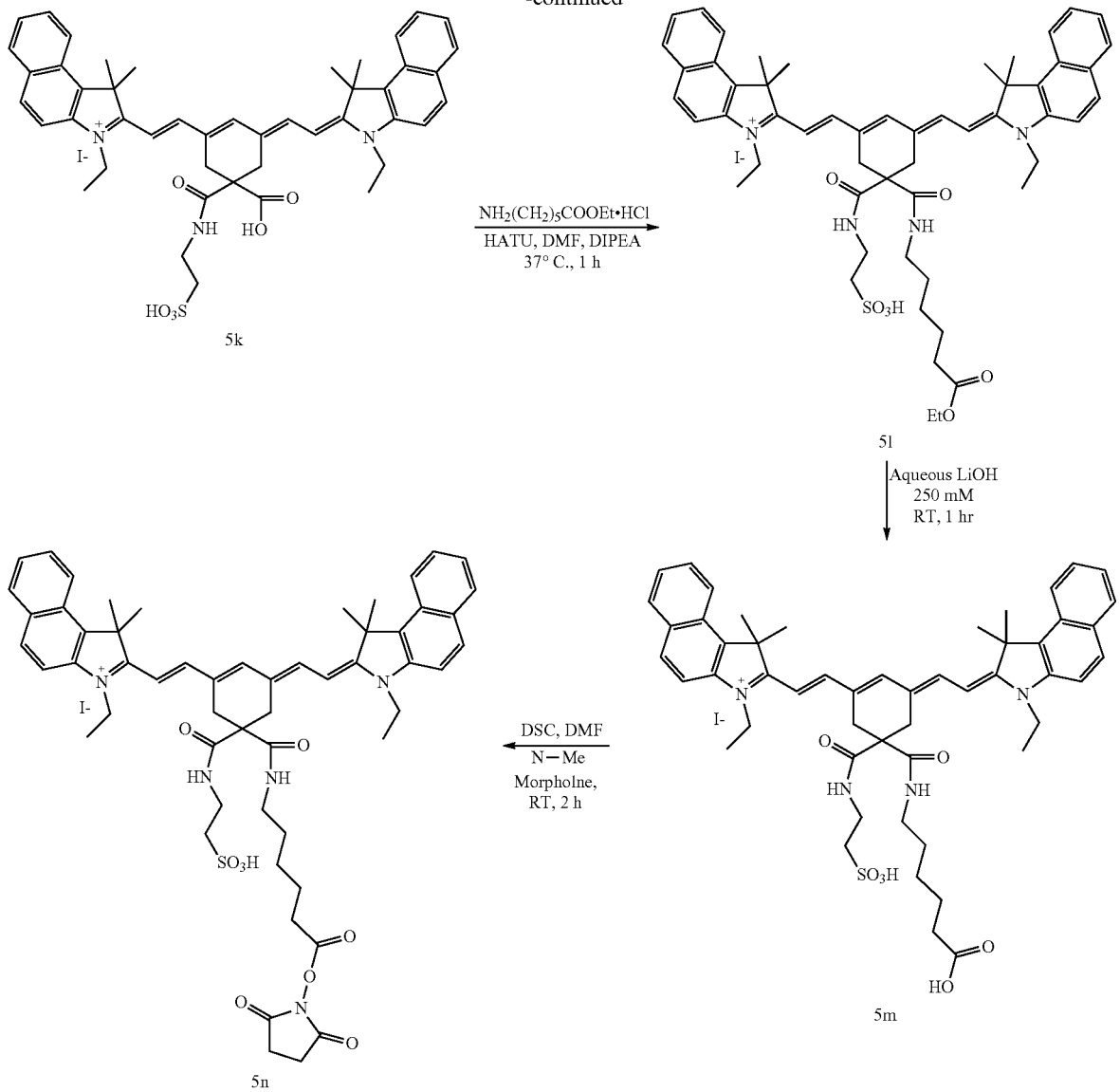
-continued

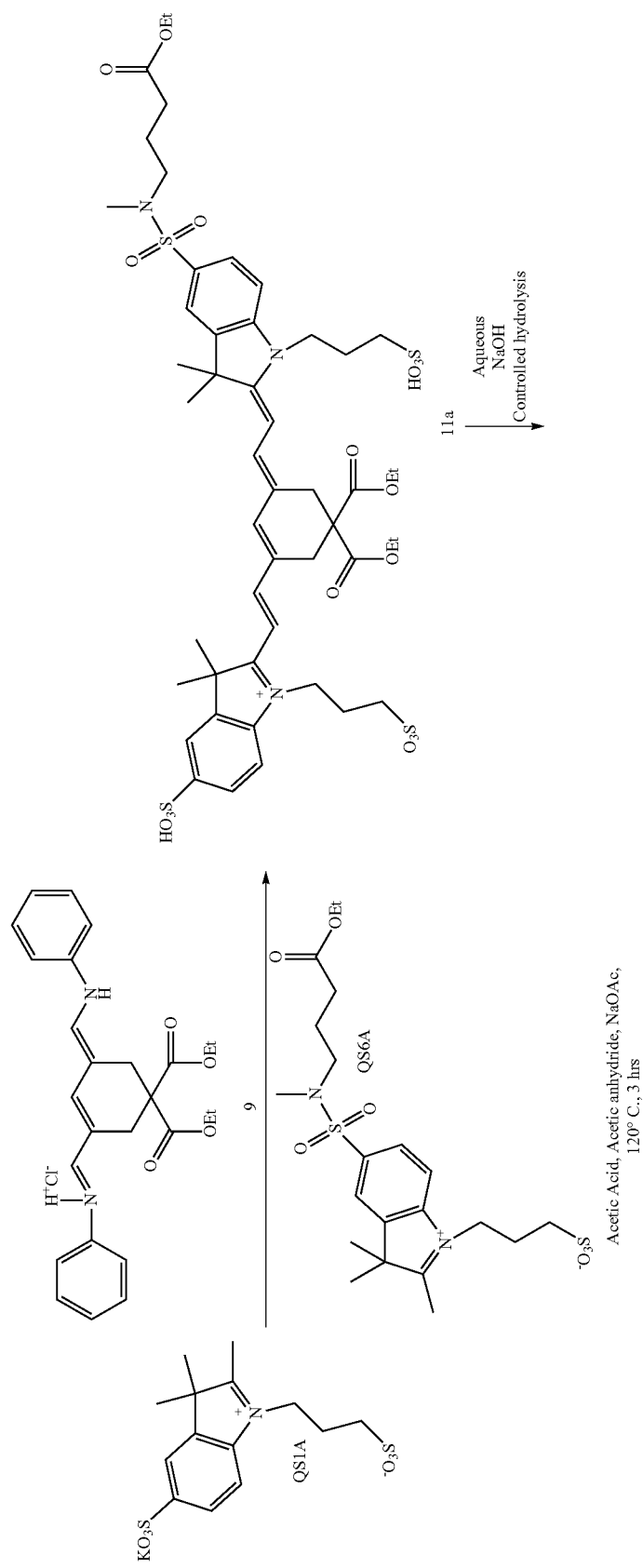

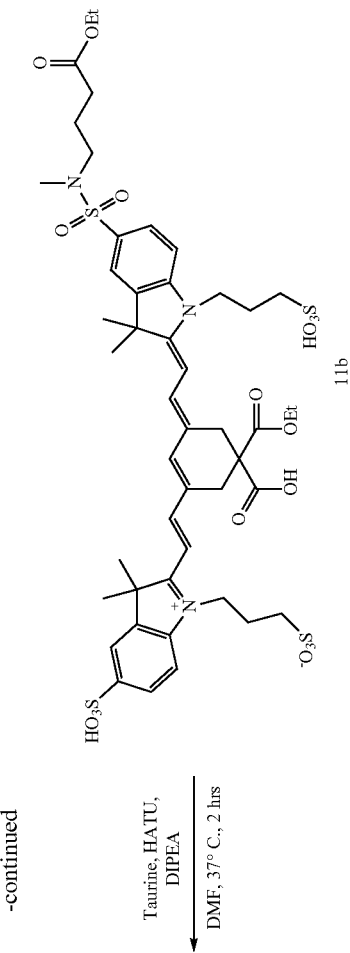
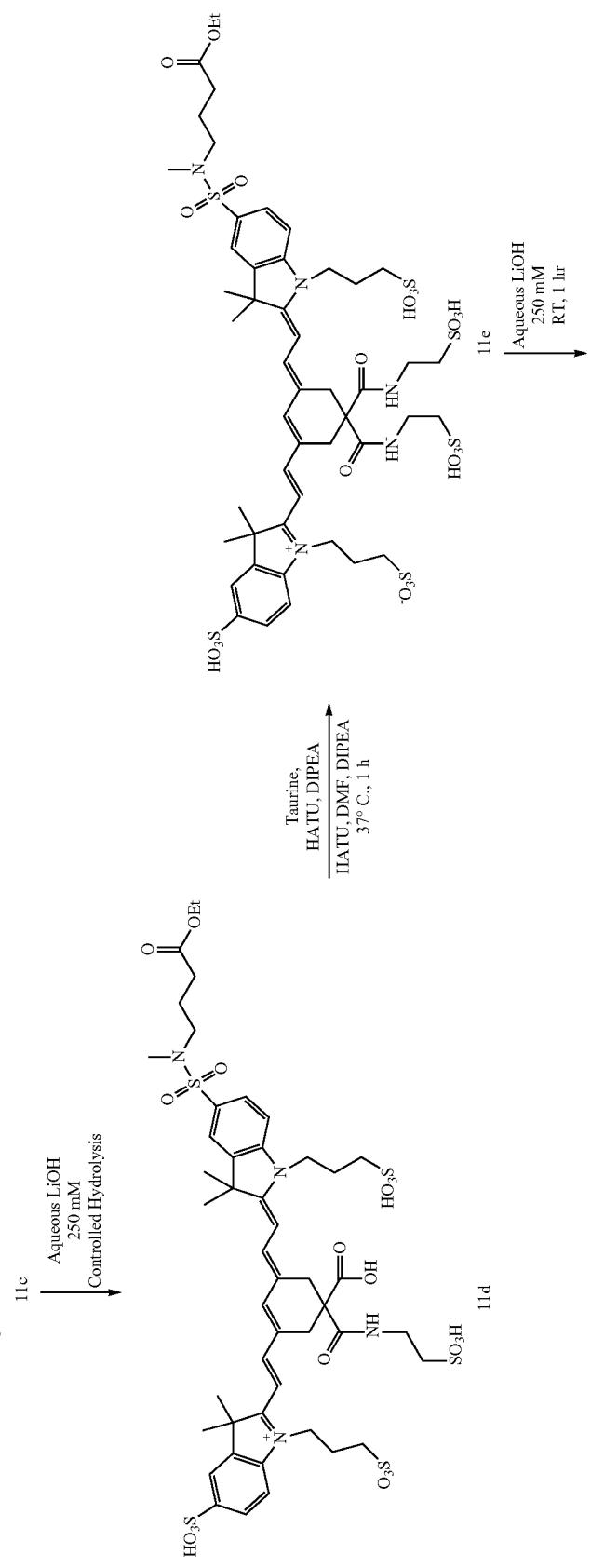

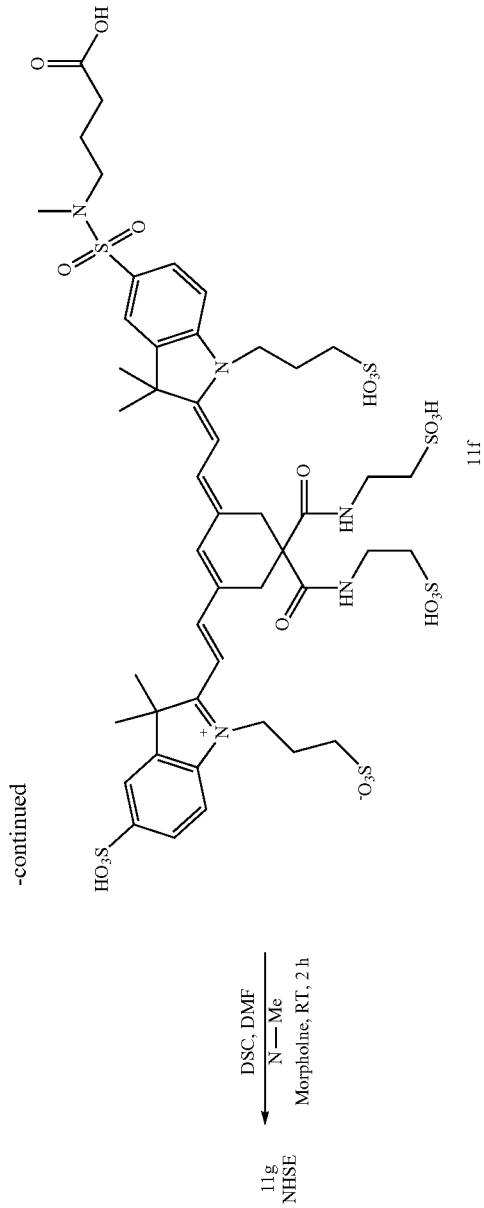

Scheme 3L. Synthesis of Asymmetric Indolinium-Benzothiazole Dye
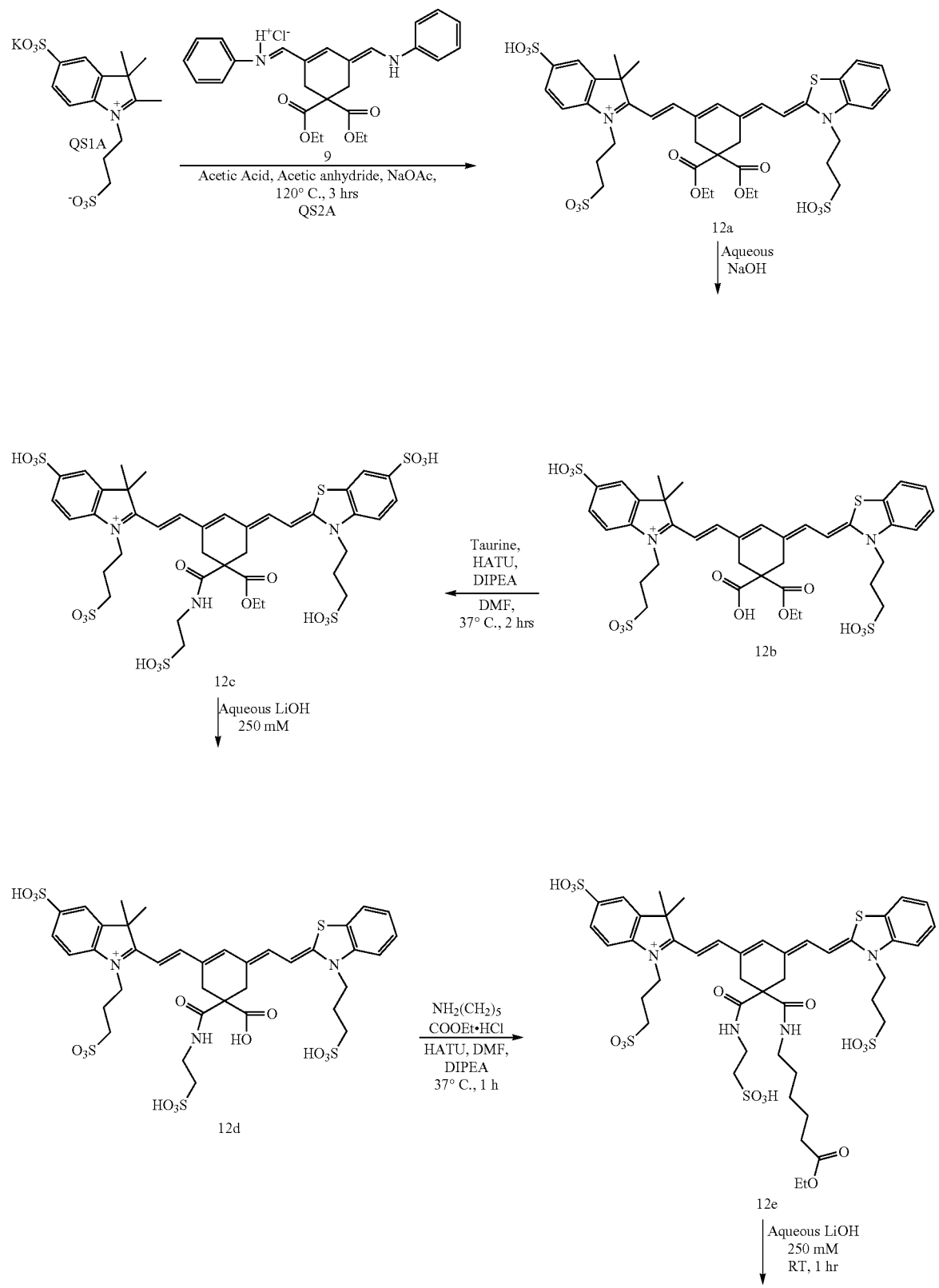

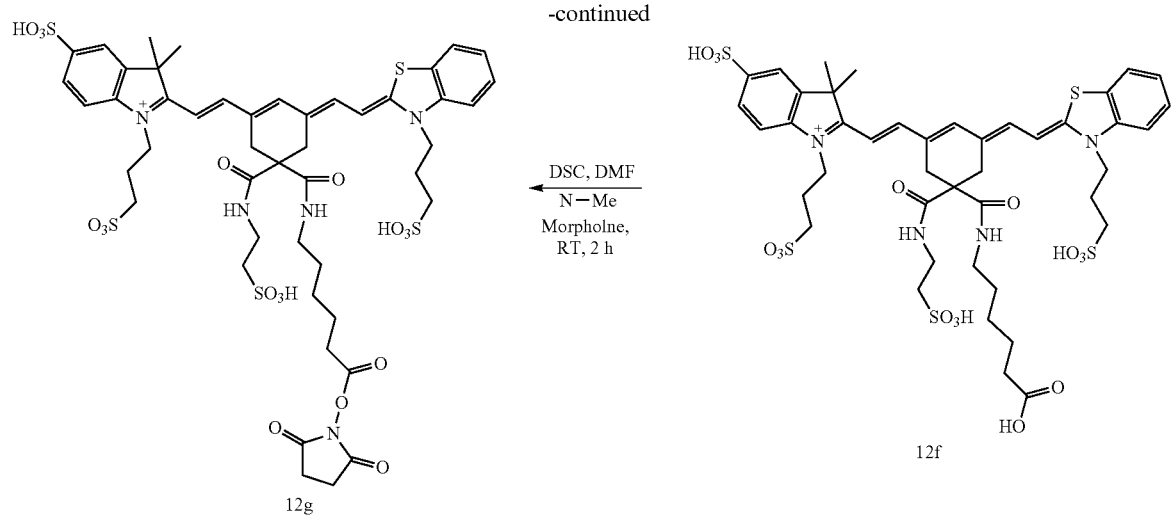
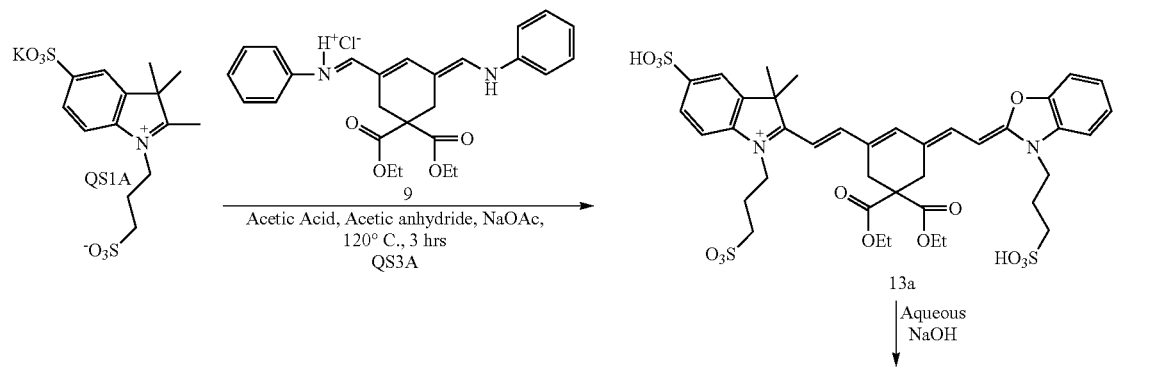
Scheme 3M. Synthesis of Asymmetric Indolinium-Benzothiazole Dye
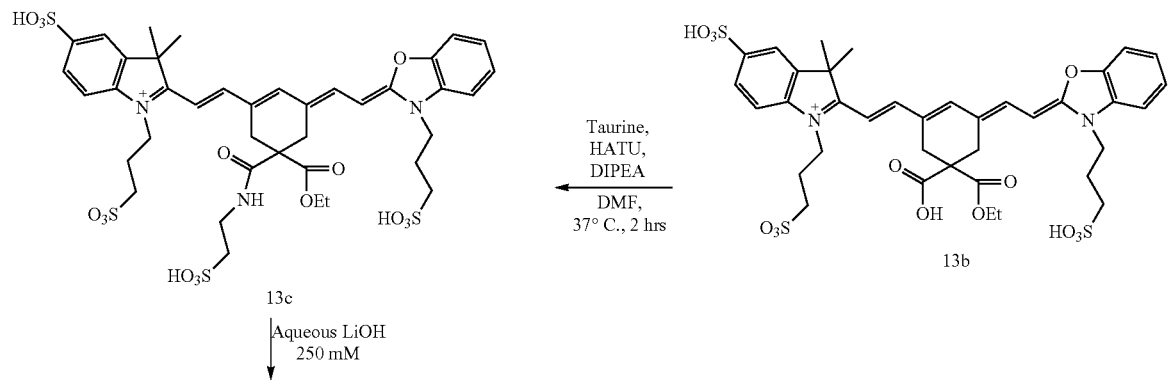

105 106
-continued
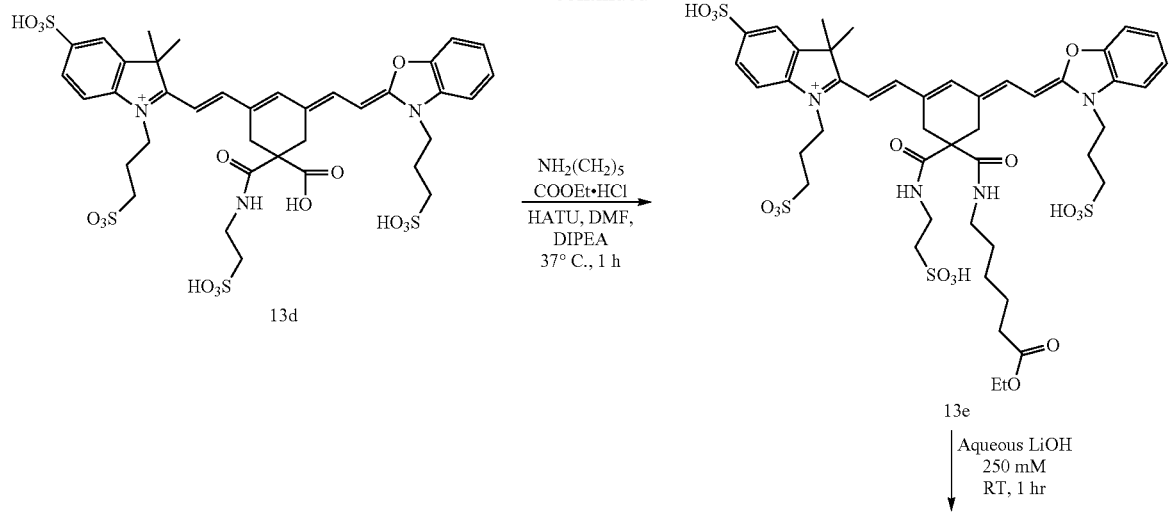
13d → (NH₂(CH₂)₅COOEt·HCl, HATU, DMF, DIPEA, 37° C., 1 h) → 13e
↓ Aqueous LiOH 250 mM RT, 1 hr
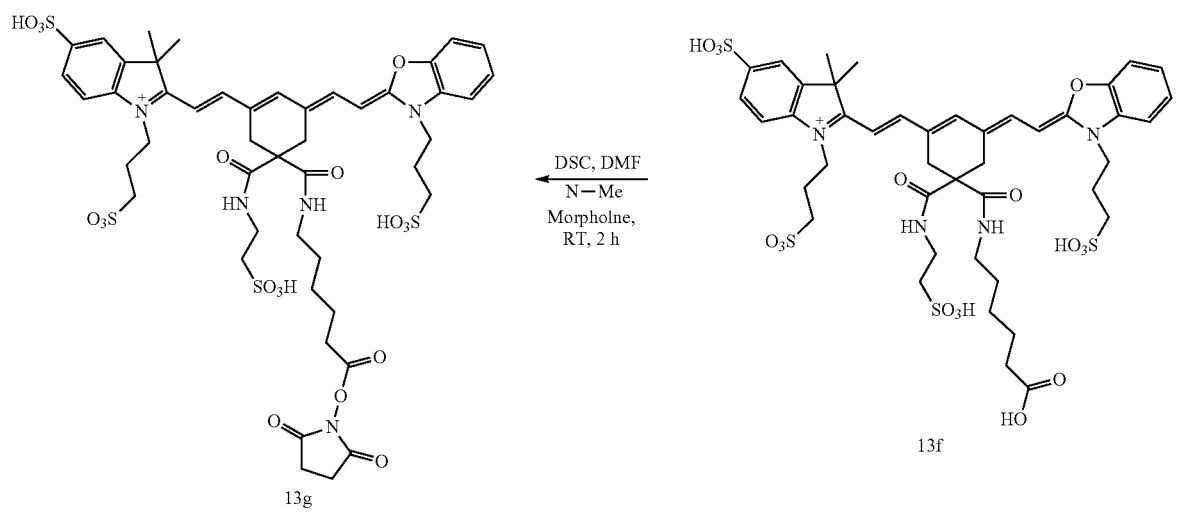
13g ← (DSC, DMF, N-Me Morpholne, RT, 2 h) ← 13f
Scheme 3N. Synthesis of Asymmetric Indolinium-Benzothiazole Dye
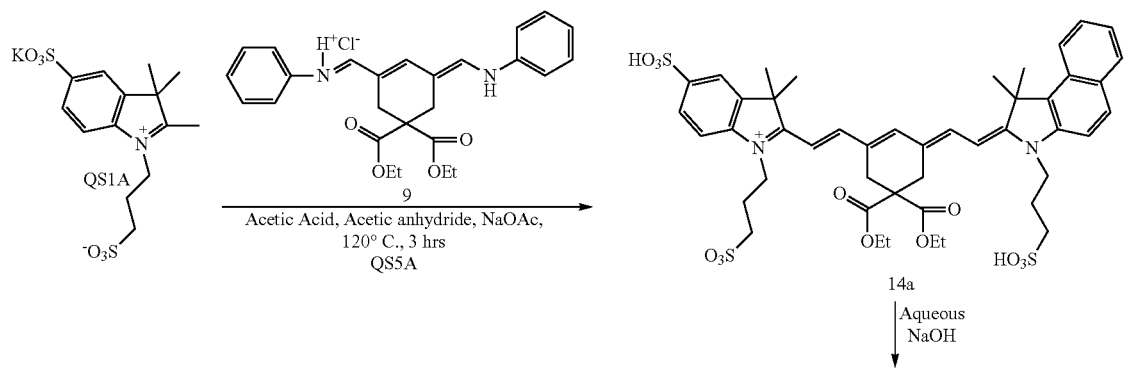
QS5A + 9 → (Acetic Acid, Acetic anhydride, NaOAc, 120° C., 3 hrs) → 14a
↓ Aqueous NaOH 107 108
-continued
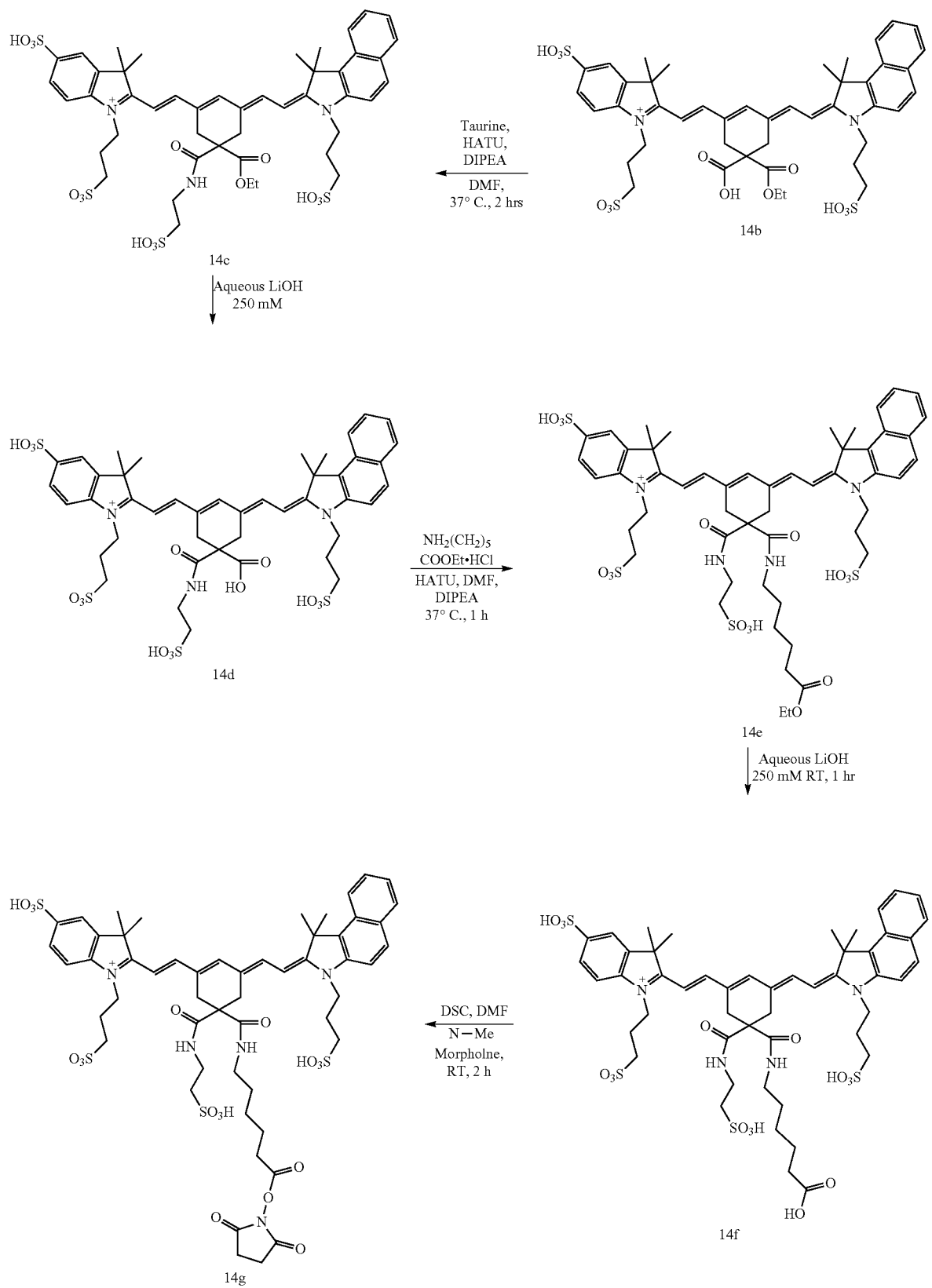

Scheme 3P. Synthesis of Symmetric Indolinium Hydrophobic Dye
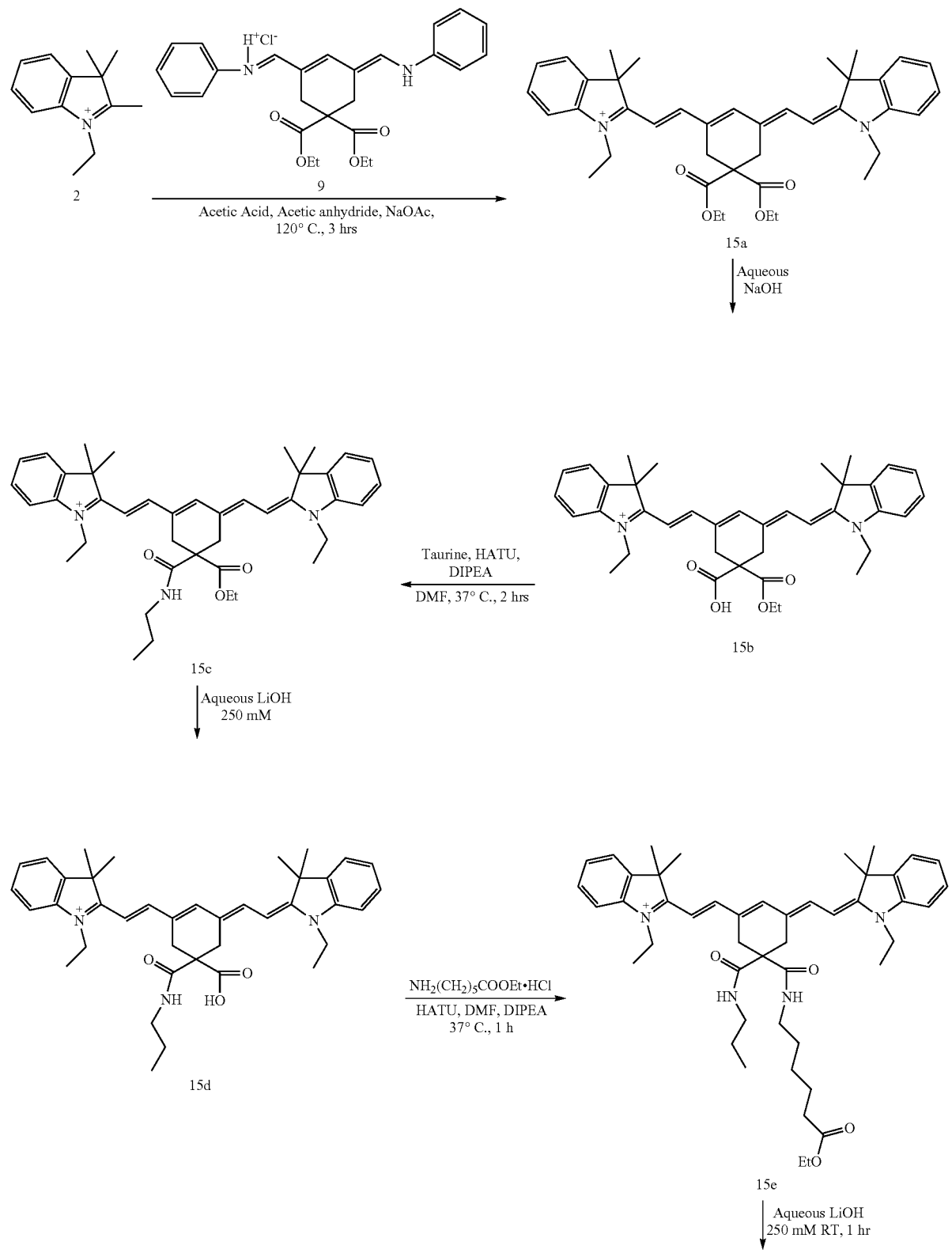

111 112
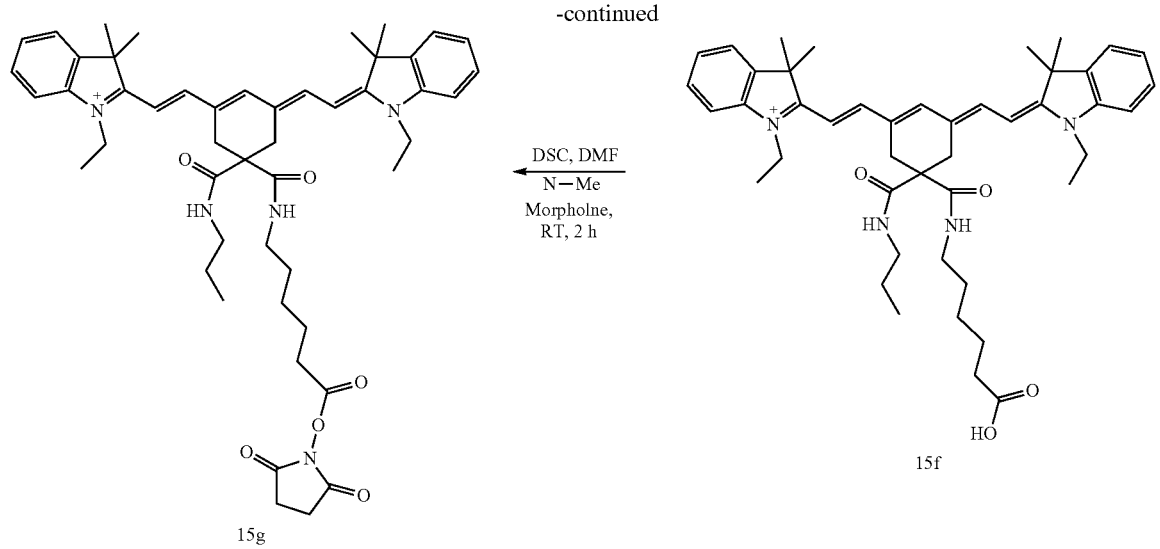
-continued
Scheme 3Q. Synthesis of Symmetric Indolinium Dye
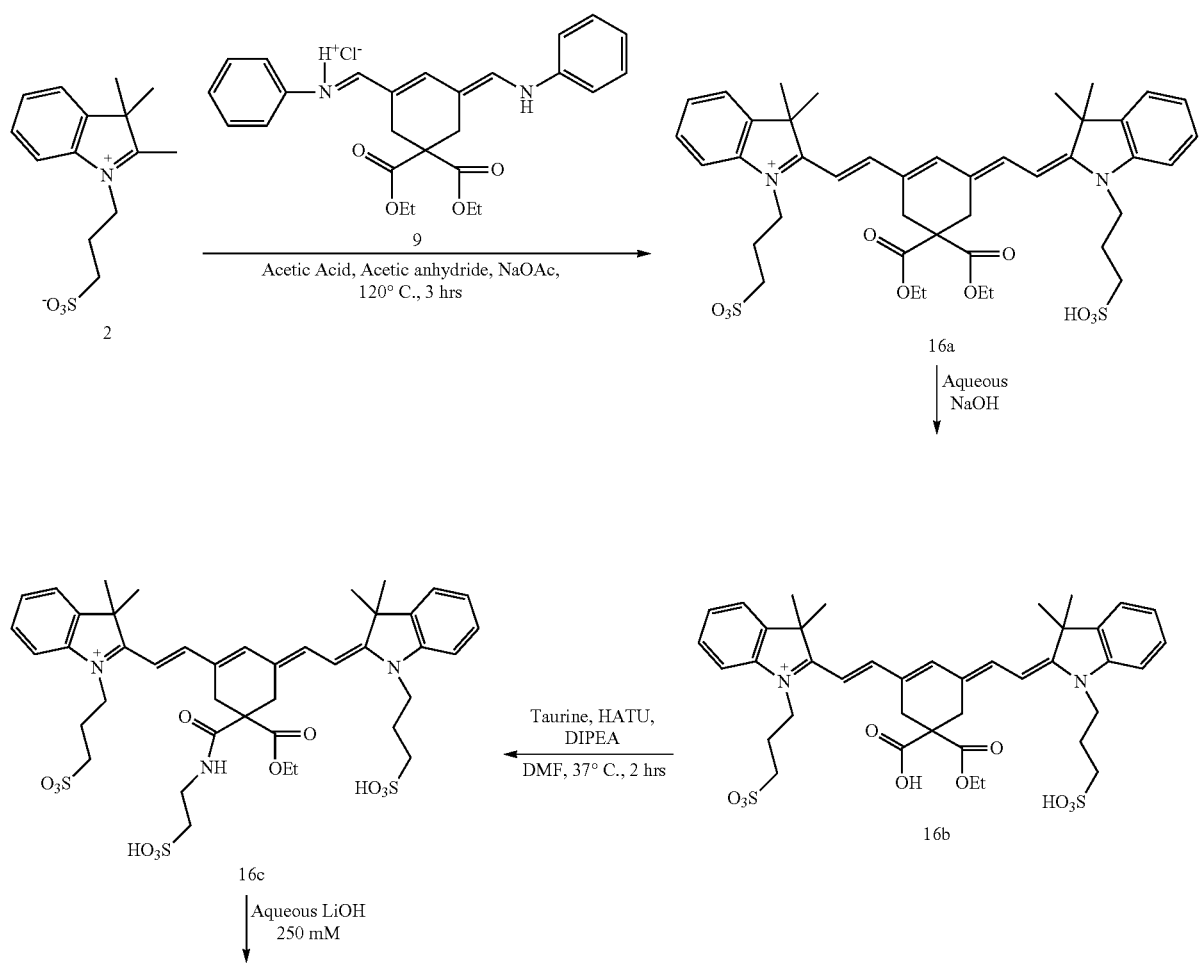

-continued
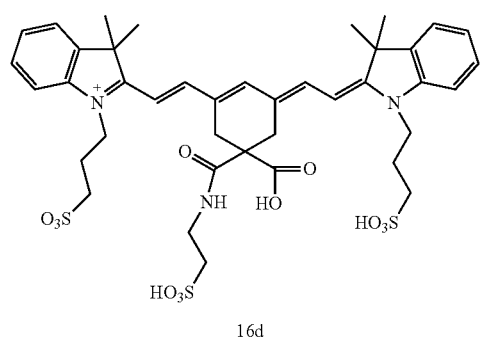
16d
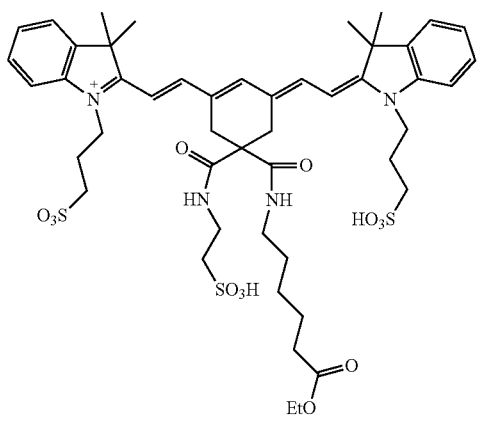
16e
NH₂(CH₂)₅COOEt·HCl
HATU, DMF, DIPEA
37° C., 1 h
Aqueous LiOH
250 mM
RT, 1 hr
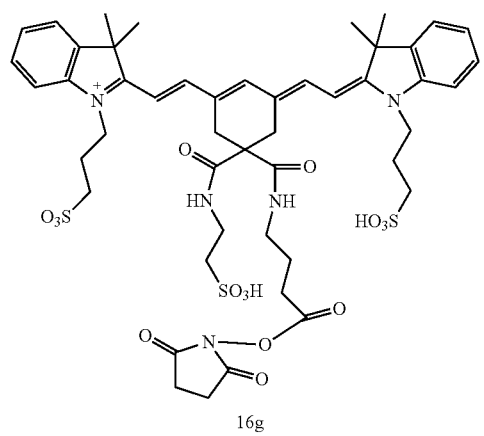
16g
DSC, DMF
N—Me
Morpholne,
RT, 2 h
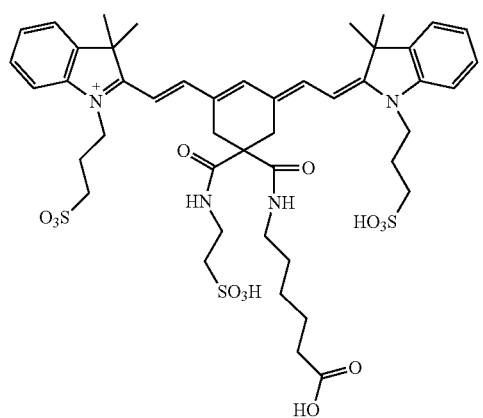
16f
Scheme 3R. Synthesis of Symmetric Indolinium Hydrophobic Dye with two long chain tails
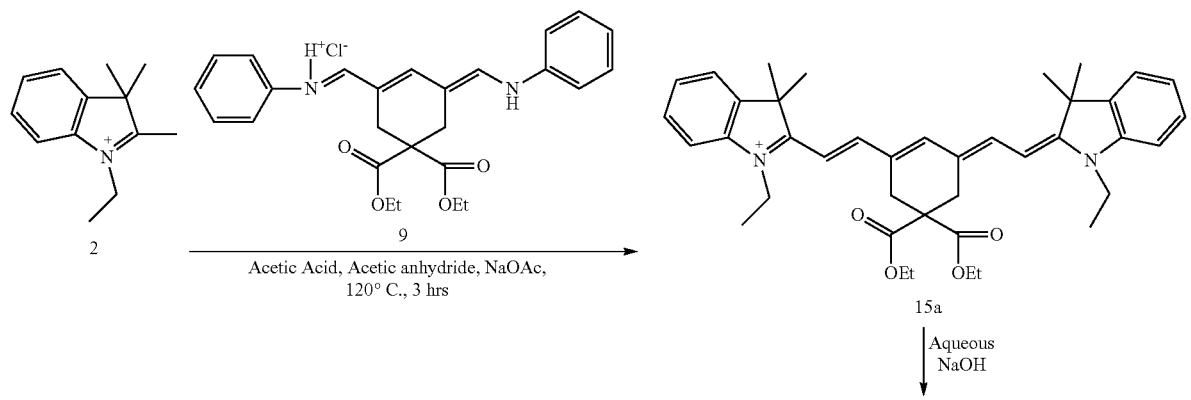
Acetic Acid, Acetic anhydride, NaOAc,
120° C., 3 hrs
15a
Aqueous NaOH

115 116
-continued
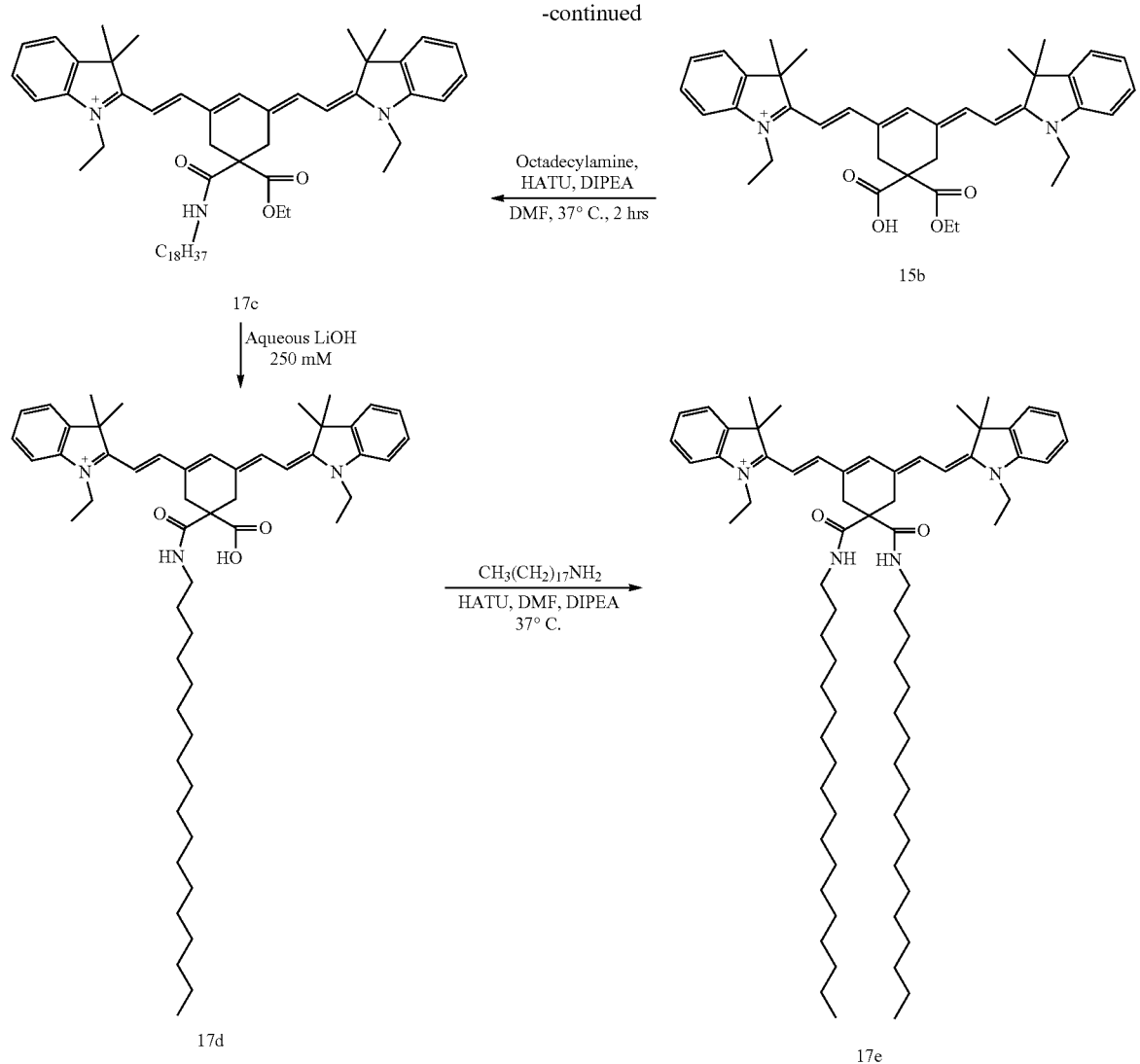
Scheme 3S. Synthesis of Symmetric Indolinium Hydrophilic Maleimide Dye
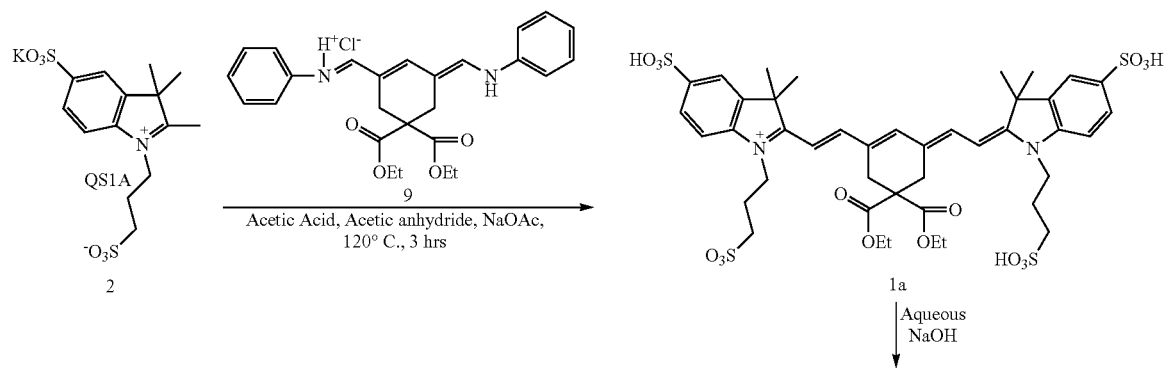

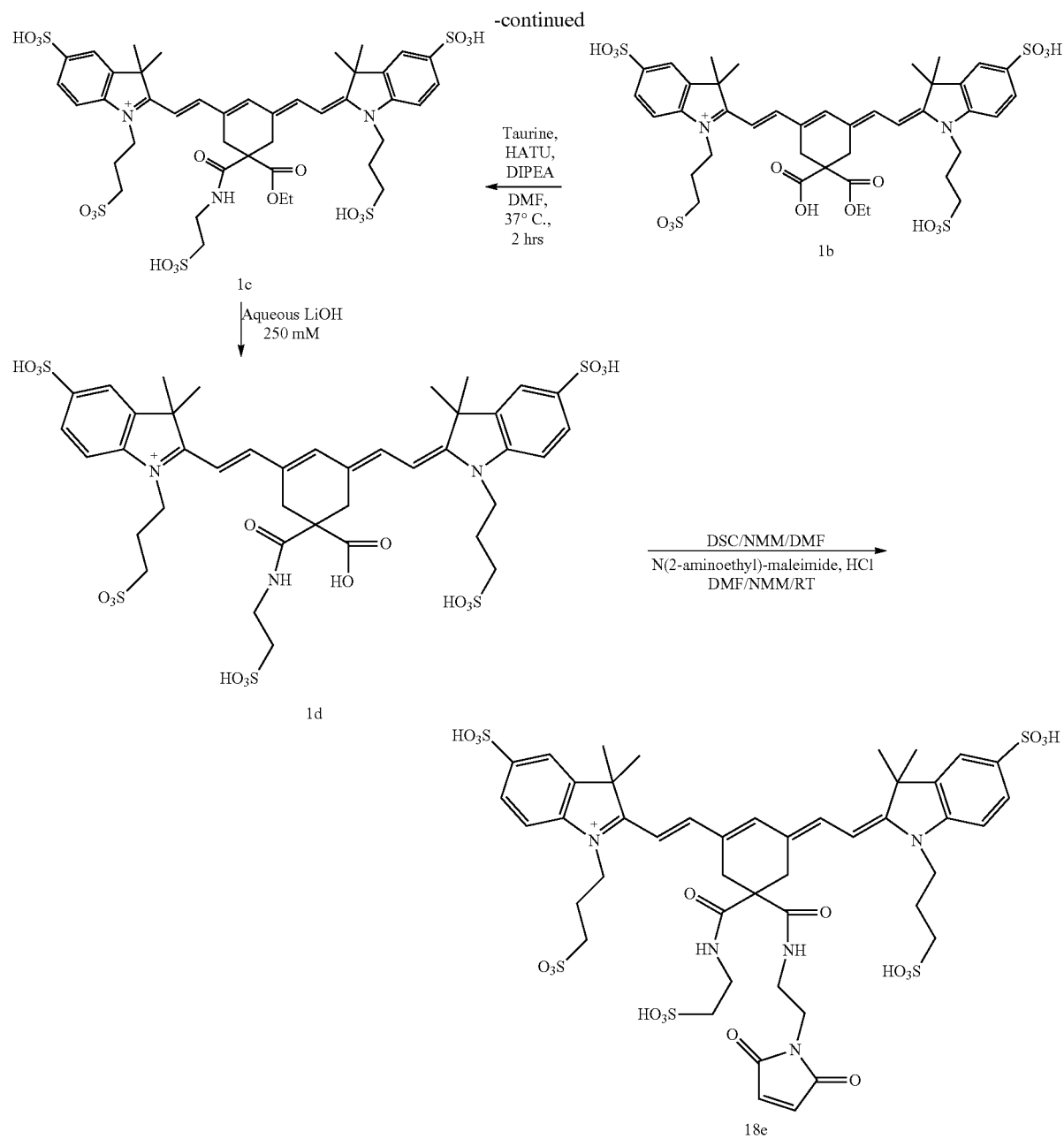

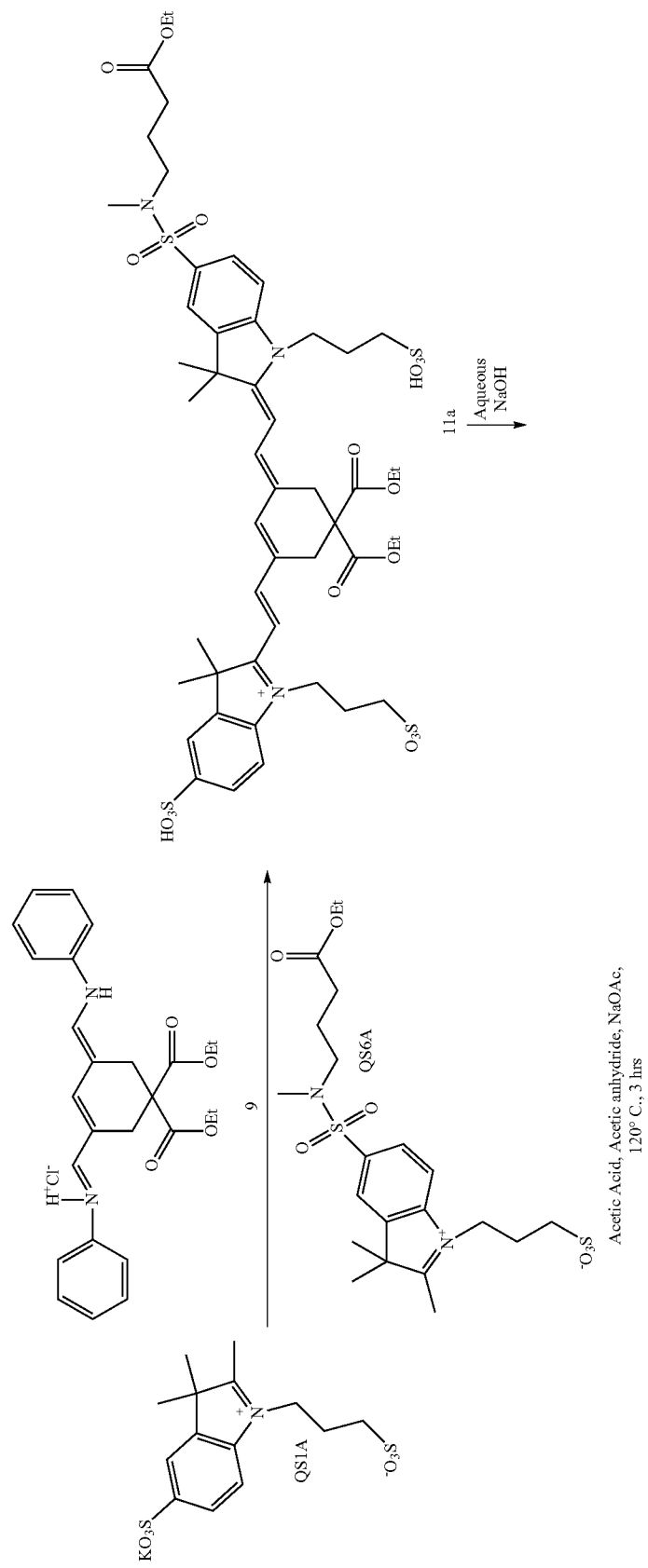
Scheme 3T. Synthesis of Asymmetric Indolinium Dye

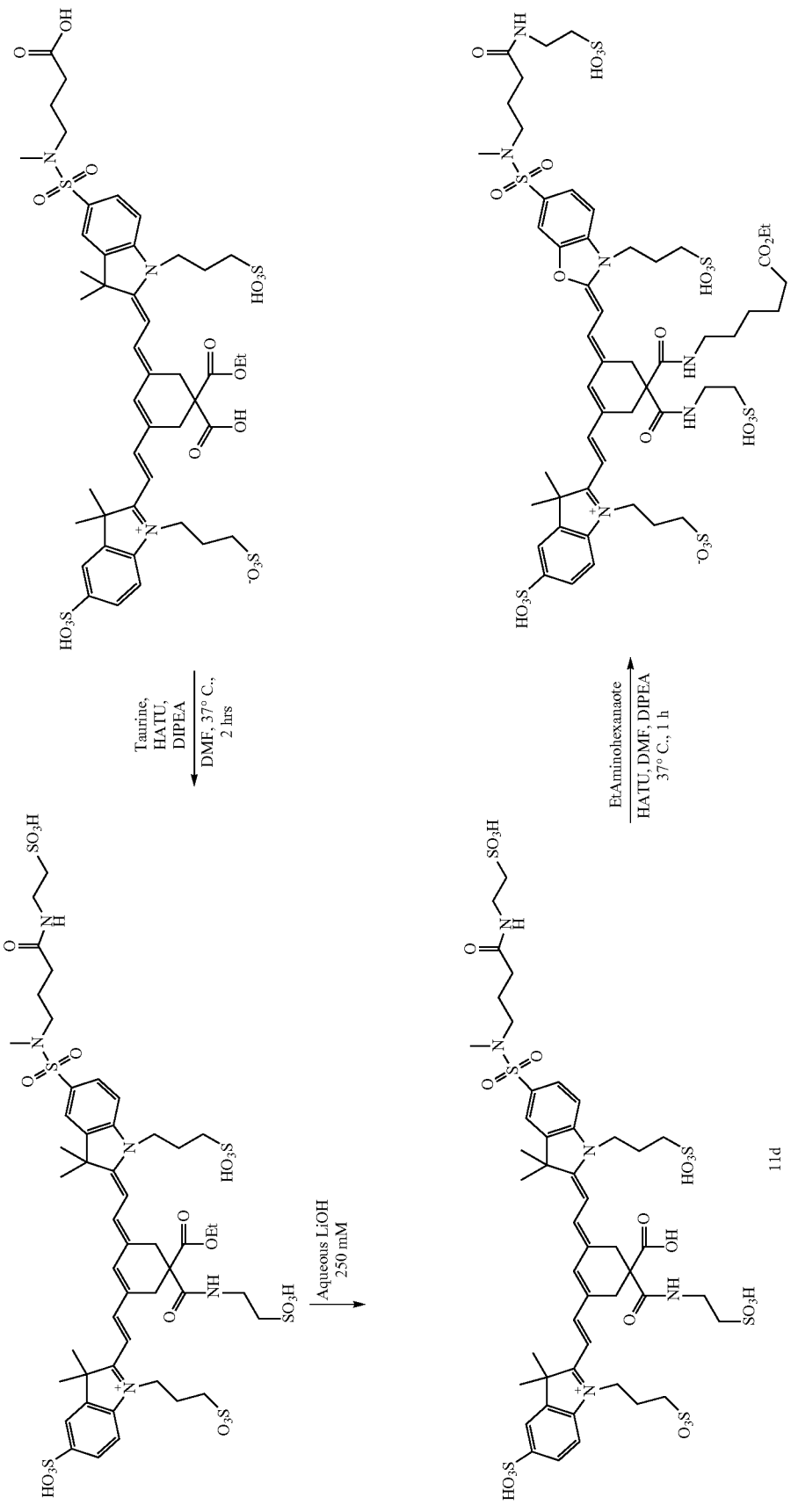

-continued
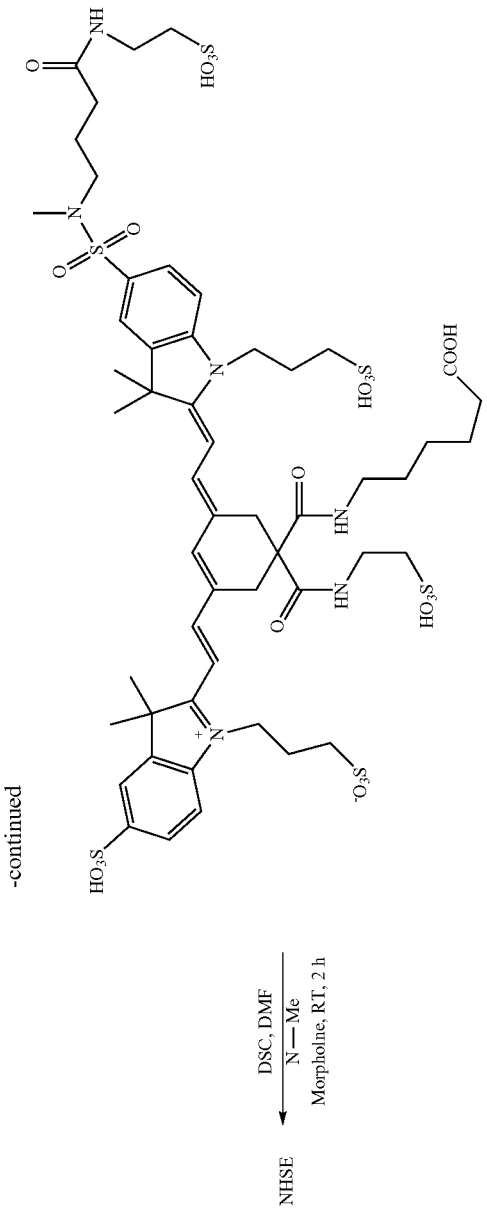
DSC, DMF
N—Me
Morpholne, RT, 2 h
NHSE

Example 4—Synthesis of Compound 4m (Scheme 3H)

A. Preparation of Compound QS4B 2,3,3-Trimethylbenzindole-5,7-disulfonate (compound 4, 3.1 g, 7 mmol) was dissolved in 25 mL of dry DMF resulting in a clear orange solution. Ethyl iodide, 3 mL (5.85 g, 37.5 mmol, Aldrich) was added and the solution was heated to 130° C. in a sealed tube for 16 hours. The reaction mixture, which turned dark purple was cooled and poured into 150 mL of ethyl ether. The mixture was centrifuged and the solvent decanted off. The solid product was further washed in the tube with three 25 mL portions of 2-propanol followed by 25 mL of ether and dried in vacuum. 2.6 g of dark purple solid (85%) was obtained and confirmed by MALDI-TOF-MS. m/e 397.1 [M]+ calculated for $C_{17}H_{19}NO_6S_2^+$, found 397.6.

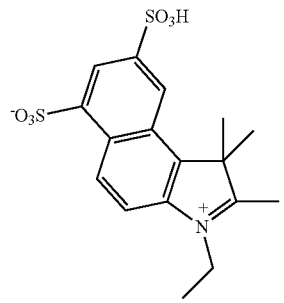

B. Preparation of Compound 4m

Compound 4m was synthesized using compounds QS4B and 9 through 4h-4l by following the same procedure that was described for the synthesis of compound 1f. The overall yield was around 15%. Abs. max: 775 nm (water), 780 nm (MeOH); Em. Max: 795 nm (water), 8053 nm (MeOH).

Example 5—Cell Labeling

Mouse splenocytes are prepared as a single cell suspension, and the T cell subpopulation within the splenocyte preparation are enriched by passage over a column that removes B cells and macrophages (R&D kit, Mouse T-cell enrichment columns, MTCC500). T cells then are centrifuged to generate a cell pellet of $10^7$ cells. The supernatant is removed from the cell pellet, and a solution of 1g at 10 mg/mL (N-hydroxysuccinimide ester of Compound 1f) in 100 µL is added. The cells are incubated at room temperature for 5 minutes, followed by 2 rounds of centrifugation and resuspension in physiological buffer to wash away unbound Compound 1f. Cells are assessed by fluorescence microscopy.

Example 6—Cell Labeling and In Vivo Imaging

Mouse 4T1 breast adenocarcinoma cells are centrifuged to generate a cell pellet of $10^7$ cells. The supernatant is removed from the cell pellet, and a solution of 10 mg/mL N-hydroxysuccinimide ester of Compound 1f in 100 µL is added. Cells are incubated at room temperature for 5 minutes, followed by 2 rounds of centrifugation and resuspension in physiological buffer to wash away unbound Compound 1f. Cells are assessed by fluorescence microscopy.

Cells are injected intravenously into mice at $5 \times 10^5$ cells per mouse, and live mice are imaged by fluorescent molecular tomography immediately after injection and 24 hours after injection. As 4T1 cells primarily metastasize to the lungs, lung fluorescence can be quantified.

Example 7—FMT Imaging with a Compound 1f-Peptide Conjugate

A solution of the N-hydroxysuccinimide ester of Compound 1f is chemically linked to an Arg-Gly-Asp containing peptide under basic conditions to yield a biocompatible fluorescent molecule for in vivo optical imaging.

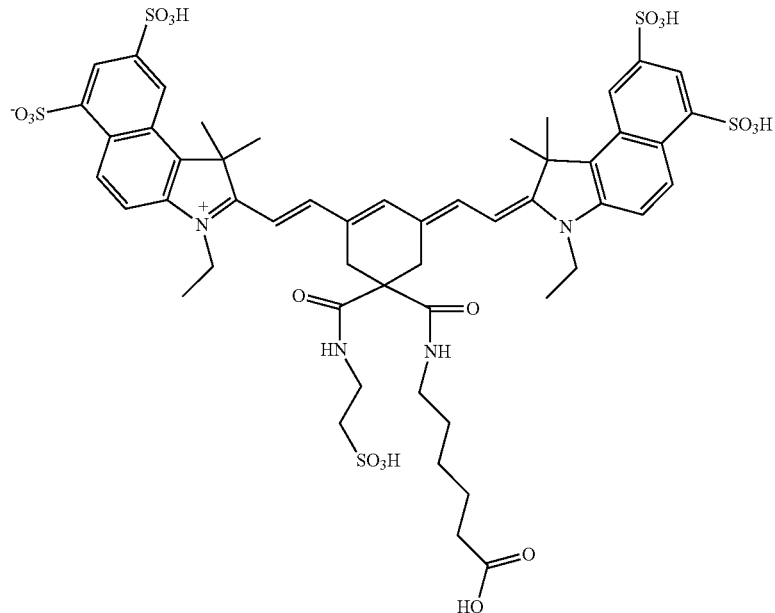

The tumor cell line HT-29 (human colon carcinoma/HTB-38) is obtained from ATCC (Manassas, Va.). HT-29 cells are grown in McCoy's supplemented with 10% FBS at 37° C. in a humidified atmosphere containing 5% $CO_2$. Exponentially growing cells are trypsinized and re-suspended in Hank's Balanced Salt Solution at a concentration of $3 \times 10^7$ cells/mL. Female NU/NU mice 6-8 weeks old (Charles River Laboratory, Wilmington, Mass.) are injected subcutaneously with $3 \times 10^6$ HT-29 cells bilaterally in the first mammary fat pads. One week later, when tumors are approximately 30 $mm^3$, the mice are injected intravenously with the fluorescent molecule (in 150 μL of 1×PBS) and imaged after 24 hours on a fluorescence reflectance system (FRI, Kodak 2000MM) system and a Fluorescence Tomography System (FMT2500) from PerkinElmer, Inc. (Waltham, Mass.).

Example 8—In Vivo Imaging of Bone Growth with Compound 1f

A solution of the N-hydroxysuccinimide ester of Compound 1f is chemically linked to a bisphosphonate containing biomolecule under basic conditions to yield a biocompatible fluorescent molecule for in vivo optical imaging.

Five day-old BALB/c×CF-1 $F_1$ mice are injected subcutaneously with the fluorescent molecule (in 15 μL 1×PBS) and imaged 24 hours later using a fluorescence reflectance imaging (FRI) system (Kodak 2000MM). Areas of bone growth are imaged.

Example 9—Nanoparticle Labeling

A solution of the N-hydroxysuccinimide ester of Compound 1f is chemically linked to amine groups disposed on a polymeric surface of iron oxide nanoparticles to yield a biocompatible fluorescent platform for in vivo fluorescence imaging. Subsequent coupling of polyethyleneglycol to these nanoparticles yields a biocompatible imaging agent suitable for fluorescence imaging and intravital microscopy.

INCORPORATION BY REFERENCE

All publications, patents, and patent applications cited herein are hereby expressly incorporated by reference in their entirety and for all purposes to the same extent as if each was so individually denoted.

EQUIVALENTS

The invention may be embodied in other specific forms without departing form the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. A compound of Formula V:

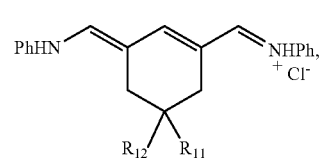

Formula V wherein:
R$_{11}$ and R$_{12}$ are independently: COOH, CONHR, CF$_3$, halogen, CN, O═C-Phenyl, or COCH$_2$R;
R is H; and
Ph is phenyl group, which is optionally substituted with one of: F, Cl, Br, I, OMe, NMe$_2$, NO$_2$, CN, CF$_3$, or alkyl.

2. The compound of claim 1, wherein R$_{11}$ is COOH and R$_{12}$ is COOH.

3. The compound of claim 1, wherein the compound is:

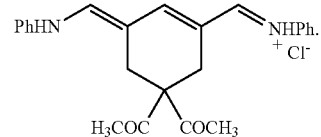

4. The compound of claim 1, wherein the compound is:

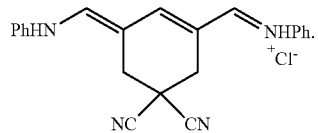

5. The compound of claim 1, wherein the compound is:

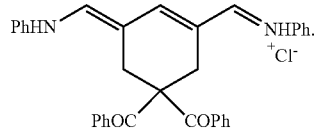

6. The compound of claim 1, wherein the compound is the compound of Formula Va:

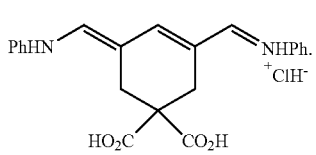

Formula Va

* * * * *